US009931347B2

(12) United States Patent
Cowley et al.

(10) Patent No.: US 9,931,347 B2
(45) Date of Patent: Apr. 3, 2018

(54) PHARMACEUTICAL COMPOUND

(71) Applicant: IOmet Pharma Ltd., Edinburgh, Midlothian (GB)

(72) Inventors: Phillip Martin Cowley, Edinburgh (GB); Alan Wise, Edinburgh (GB); Margaret Huggett, Dundee (GB)

(73) Assignee: IOmet Pharma Ltd., Rahway, NJ (US)

( * ) Notice: Subject to any disclaimer, the term of this patent is extended or adjusted under 35 U.S.C. 154(b) by 0 days.

(21) Appl. No.: 15/100,494

(22) PCT Filed: Dec. 2, 2014

(86) PCT No.: PCT/EP2014/076311
§ 371 (c)(1),
(2) Date: May 31, 2016

(87) PCT Pub. No.: WO2015/082499
PCT Pub. Date: Jun. 11, 2015

(65) Prior Publication Data

US 2016/0367564 A1 Dec. 22, 2016

(30) Foreign Application Priority Data

Dec. 3, 2013 (GB) .................................. 1321316.0
Jun. 24, 2014 (GB) .................................. 1411215.5

(51) Int. Cl.
*A61K 31/551* (2006.01)
*A61K 31/404* (2006.01)
(Continued)

(52) U.S. Cl.
CPC .......... *A61K 31/551* (2013.01); *A61K 31/404* (2013.01); *A61K 31/435* (2013.01);
(Continued)

(58) Field of Classification Search
CPC .. A61K 31/551; A61K 31/404; A61K 31/435; A61K 31/4439; C07D 209/20;
(Continued)

(56) References Cited

U.S. PATENT DOCUMENTS

2005/0245540 A1* 11/2005 Takeshita ............. A61K 31/496 514/254.09
2006/0074073 A1* 4/2006 Steinfeldt ............ A61K 31/282 514/212.06

(Continued)

FOREIGN PATENT DOCUMENTS

EP 0003199 B1 11/1981
EP 0303506 A3 9/1990

(Continued)

OTHER PUBLICATIONS

Muller, A.J., et al., Indoleamine 2,3-dioxygenase in cancer: Targeting pathological immune tolerance with small-molecule inhibitors, Expert Opinion on Therapeutic Targets, 2005, pp. 831-849, vol. 9(4).

(Continued)

*Primary Examiner* — Sahar Javanmard
(74) *Attorney, Agent, or Firm* — Yong Zhao; Catherine D. Fitch

(57) ABSTRACT

Provided is a tryptophan-2,3-dioxygenase (TDO) and/or indoleamine-2,3-dioxygenase (IDO) inhibitor compound for use in medicine, which compound comprises the following formula:

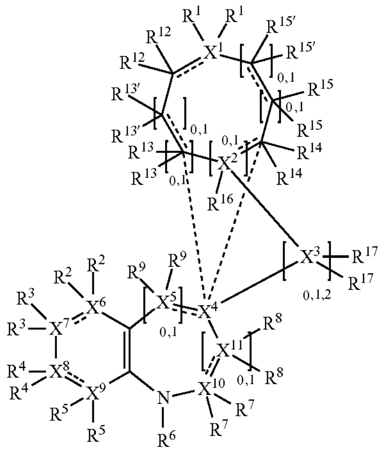

Figure 1:
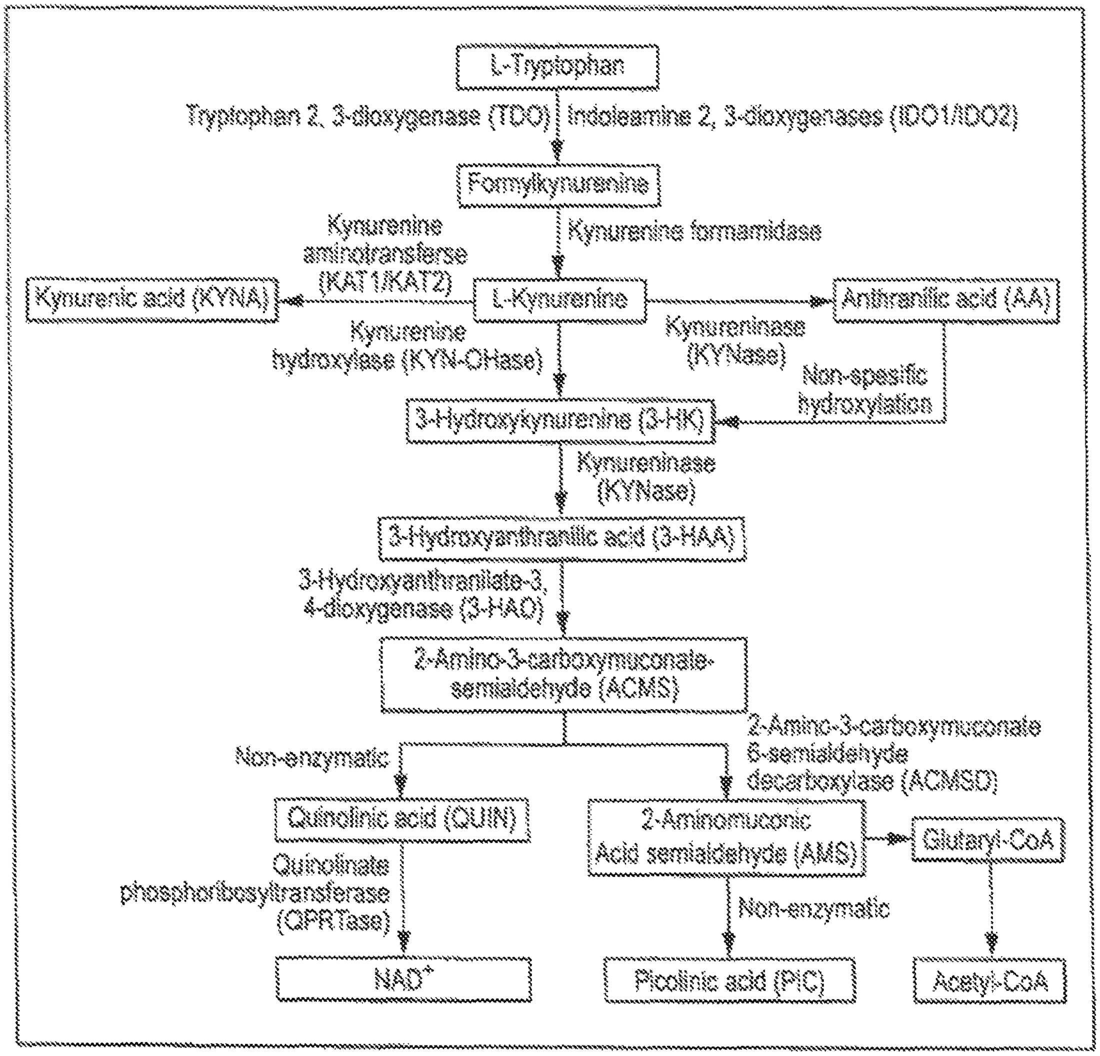

wherein $X^2$, $X^4$, $X^{10}$, and $X^{11}$ may be the same or different and each is independently selected from C and N; $X^1$, $X^3$, $X^5$, $X^6$, $X^7$, $X^8$, and $X^9$ may be the same or different and each is independently selected from C, N and O; each bond having a dotted line may independently be a double bond or a single bond, provided that valencies at each atom are maintained; the dotted lines joining $X^4$ with the carbon atoms either side of $X^2$ are single bonds, and are only present when $X^2$ is absent, $X^3$ is absent and $X^4$ is C, and when these bonds are present the ring carbons on each side of $X^2$ are not directly bonded to each other; each $R^1$ may be present or absent and may be the same or different and is selected from H and a substituted or unsubstituted organic group, provided that the number of $R^1$ groups present is such that the valency of $X^1$ is maintained; each $R^{12}$, $R^{13}$, $R^{13'}$, $R^{14}$, $R^{15}$ and $R^{15'}$ may be present or absent and may be the same or different and each is independently selected from H and a substituted or unsubstituted organic group, provided that the number of such R groups present is such that the valency of the ring carbon atoms is maintained; $R^{16}$ may be present or absent and is selected from H and a substituted or unsubstituted organic group, provided that the number of $R^{16}$ groups present is such that the valency of $X^2$ is maintained; each $R^{17}$ may be present or absent and may be the same or different and is independently selected from H and a substituted or (Continued)

unsubstituted organic group, provided that the number of $R^{17}$ groups present is such that the valency of $X^3$ is maintained; each $R^2$, $R^3$, $R^4$, and $R^5$ may be present or absent and may be the same or different and is selected from H and a substituted or unsubstituted organic group, provided that the number of such R groups present is such that the valencies of $X^6$, $X^7$, $X^8$, and $X^9$ are maintained; each $R^7$, $R^8$ and $R^9$ may be present or absent and may be the same or different and is selected from H and a substituted or unsubstituted organic group, provided that the number of such R groups present is such that the valencies of $X^{10}$, $X^{11}$, and $X^5$ are maintained; and $R^6$ is selected from H and a substituted or unsubstituted organic group, preferably H and a substituted or unsubstituted $C_1$-$C_6$ alkyl group; and wherein any R group may form a ring with any other R group on an adjacent and/or proximal atom.

12 Claims, 2 Drawing Sheets

(51) Int. Cl.

| | |
|---|---|
| ***C07D 401/04*** | (2006.01) |
| ***C07D 403/12*** | (2006.01) |
| ***C07D 401/12*** | (2006.01) |
| ***C07D 403/04*** | (2006.01) |
| ***C07D 405/12*** | (2006.01) |
| ***C07D 413/12*** | (2006.01) |
| ***C07D 471/04*** | (2006.01) |
| ***C07D 487/04*** | (2006.01) |
| ***C07D 209/34*** | (2006.01) |
| ***C07D 209/40*** | (2006.01) |
| ***C07D 513/04*** | (2006.01) |
| ***A61K 31/435*** | (2006.01) |
| ***A61K 31/4439*** | (2006.01) |
| ***A61K 31/444*** | (2006.01) |
| ***A61K 31/454*** | (2006.01) |
| ***A61K 31/4545*** | (2006.01) |
| ***A61K 31/4725*** | (2006.01) |
| ***A61K 31/496*** | (2006.01) |
| ***A61K 31/497*** | (2006.01) |
| ***A61K 31/498*** | (2006.01) |
| ***A61K 31/4985*** | (2006.01) |
| ***A61K 31/506*** | (2006.01) |
| ***A61K 31/5377*** | (2006.01) |
| ***A61K 31/55*** | (2006.01) |
| ***A61K 45/06*** | (2006.01) |
| ***C07D 209/20*** | (2006.01) |
| ***C07D 401/06*** | (2006.01) |
| ***C07D 401/14*** | (2006.01) |
| ***C07D 403/06*** | (2006.01) |
| ***C07D 405/14*** | (2006.01) |
| ***C07D 409/14*** | (2006.01) |
| ***C07D 413/14*** | (2006.01) |
| ***C07D 471/10*** | (2006.01) |

(52) U.S. Cl.
CPC ........ *A61K 31/444* (2013.01); *A61K 31/4439* (2013.01); *A61K 31/454* (2013.01); *A61K 31/4545* (2013.01); *A61K 31/4725* (2013.01); *A61K 31/496* (2013.01); *A61K 31/497* (2013.01); *A61K 31/498* (2013.01); *A61K 31/4985* (2013.01); *A61K 31/506* (2013.01); *A61K 31/5377* (2013.01); *A61K 31/55* (2013.01); *A61K 45/06* (2013.01); *C07D 209/20* (2013.01); *C07D 209/34* (2013.01); *C07D 209/40* (2013.01); *C07D 401/04* (2013.01); *C07D 401/06* (2013.01); *C07D 401/12* (2013.01); *C07D 401/14* (2013.01); *C07D 403/04* (2013.01); *C07D 403/06* (2013.01); *C07D 403/12* (2013.01); *C07D 405/12* (2013.01); *C07D 405/14* (2013.01); *C07D 409/14* (2013.01); *C07D 413/12* (2013.01); *C07D 413/14* (2013.01); *C07D 471/04* (2013.01); *C07D 471/10* (2013.01); *C07D 487/04* (2013.01); *C07D 513/04* (2013.01)

(58) Field of Classification Search
CPC .. C07D 209/34; C07D 209/40; C07D 401/04; C07D 401/06
See application file for complete search history.

(56) References Cited

U.S. PATENT DOCUMENTS

| | | | | |
|---|---|---|---|---|
| 2007/0105907 A1 | 5/2007 | Prendergast et al. | | |
| 2007/0167426 A1 | 7/2007 | Siddiqui et al. | | |
| 2008/0015214 A1* | 1/2008 | Bignan | ................ | C07D 401/04 514/300 |

FOREIGN PATENT DOCUMENTS

| | | | |
|---|---|---|---|
| EP | 1069124 | B1 | 5/2004 |
| WO | 9851301 | A1 | 11/1998 |
| WO | 02060871 | A2 | 8/2002 |
| WO | WO2004093871 | A1 | 11/2004 |

OTHER PUBLICATIONS

Pantouris, G., et al., Antitumour agents as inhibitors of tryptophan 2,3-dioxygenase, Biochemical and Biophysical Research Communications, 2013, pp. 28-31, vol. 433(1).

* cited by examiner

PHARMACEUTICAL COMPOUND

The present invention relates to tryptophan-2,3-dioxygenase (TDO) or indoleamine-2,3-dioxygenase (IDO [IDO1 or IDO2]) inhibitors, and in particular TDO and IDO inhibitors for use in medicine. The inhibitors of the invention may be used in pharmaceutical compositions, and in particular pharmaceutical compositions for treating a cancer, an inflammatory condition, an infectious disease, a central nervous system disease or disorder and other diseases, conditions and disorders. The invention also relates to methods of manufacture of such inhibitors, and methods of treatment using such inhibitors.

Tryptophan Metabolism

The kynurenine pathway (KP) is responsible for >95% of the degradation of the essential amino acid tryptophan. The kynurenine pathway for tryptophan metabolism leads to the production of the essential pyridine nucleotide NAD+ and a number of neuroactive metabolites, including kynurenine (KYN), kynurenic acid (KYNA), the neurotoxic free-radical generator 3-hydroxykynurenine (3-HK), anthranilic acid, 3-HAA, picolinic acid (PIC), and the excitatory N-methyl-D-aspartate (NMDA) receptor agonist and neurotoxin, quinolinic acid (QUIN) (see FIG. 1). The remaining 5% of tryptophan is metabolised by tryptophan hydroxylase to 5-hydroxytryptophan and then further to 5-hydroxytryptamine (serotonin) and melatonin.

Both the depletion of tryptophan and accumulation of immunosuppressive tryptophan catabolites act to supress antigen-specific T-cell and natural killer cell responses and induce the formation of regulatory T cells. Because tryptophan catabolism is induced by inflammatory mediators, notably IFN-γ, it is thought to represent an endogenous mechanism that restricts excessive immune responses, thereby preventing immunopathology. However, there is evidence that in disease states this feedback loop may not be beneficial (reviewed in (Munn and Mellor, 2013).

IDO/TDO

The first step of tryptophan catabolism is catalysed by either TDO or IDO. Both enzymes catalyze the oxidative cleavage of the 2,3 double bond in the indole ring, converting tryptophan to N-formylkynurenine. This is the rate-limiting step in tryptophan catabolism by the kynurenine pathway (Grohmann et al., 2003; Stone and Darlington, 2002). TDO is a homotetramer with each monomer having a molecular mass of 48 kDa, whereas IDO has a molecular mass of 45 kDa and a monomeric structure (Sugimoto et al., 2006; Thackray et al., 2008; Zhang et al., 2007). Despite mediating the same reaction, TDO and IDO are structurally distinct, sharing only 10% homology mainly within the active site (Thackray et al., 2008).

TDO is expressed at high levels in the liver and is responsible for regulating systemic tryptophan levels. TDO is not induced or regulated by signals from the immune system, however TDO expression can be induced by tryptophan or corticosteroids (Miller et al., 2004; Salter and Pogson, 1985). More recently, TDO has been found to be expressed in the brain, where it regulates the production of neuroactive tryptophan metabolites such as kynurenic acid and quinolinic acid (Kanai et al., 2009).

IDO is the predominant tryptophan catabolising enzyme extra hepatically and is found in numerous cells, including macrophages, microglia, neurons and astrocytes (Guillemin et al., 2007; Guillemin et al., 2001; Guillemin et al., 2003; Guillemin et al., 2005). IDO transcription is stringently controlled, responding to specific inflammatory mediators. The mouse and human IDO gene promoters contain multiple sequence elements that confer responsiveness to type I (IFN-α/β) and, more potently, type II (IFN-γ) interferons (Chang et al., 2011; Dai and Gupta, 1990; Hassanain et al., 1993; Mellor et al., 2003). Various cell types, including certain myeloid-lineage cells (monocyte-derived macrophages and DCs), fibroblasts, endothelial cells and some tumour-cell lines, express IDO after exposure to IFN-γ (Burke et al., 1995; Hwu et al., 2000; Mellor et al., 2003; Munn et al., 1999; Varga et al., 1996). However, the control of IDO transcription is complex and cell-type specific. IDO activity is found constitutively at the maternal-fetal interface, expressed by human extravillous trophoblast cells (Kudo and Boyd, 2000). Outside of the placenta, functional IDO expression was reported to be highest in the mouse epididymis, gut (distal ileum and colon), lymph nodes, spleen, thymus and lungs (Takikawa et al., 1986).

Another recent variant enzyme of IDO has been shown to catalyse the same enzymatic step: indoleamine-2,3-dioxygenase 2 (IDO2). However, its physiological relevance remains unclear due to its very low activity, the presence of common polymorphisms that inactivate its enzymatic activity in approximately half of all Caucasians and Asians, and the presence of multiple splice variants (Lob et al., 2008; Meininger et al., 2011; Metz et al., 2007).

IDO-deficient mice are at a gross level phenotypical normal (Mellor et al., 2003), however, they are slightly more prone to induction of autoimmunity and stimulation of the innate immune system. IDO −/− knockout mice also display enhanced inflammatory-mediated colon carcinogenesis and exhibit resistance to inflammation-driven lung and skin cancers (Chang et al., 2011; Yan et al., 2010).

The TDO −/− knockout mouse appears phenotypically normal. However, the TDO knockout mice have a 9-fold increase in the plasma concentration of L-Trp, while IDO −/− knockout mice had WT levels of L-Trp, this suggests that TDO and not IDO regulates systemic Trp. TDO ablation increases Trp in the brain as well as serotonin (5-HT) and is therefore a modulator of anxiety related behaviour (Kanai et al., 2009). TDO also plays a role in the maintenance of brain morphology in adult mice as TDO −/− mice show increased neurogenesis in the hippocampus and subventricular zone during adulthood (Funakoshi et al., 2011).

Immuno-Modulation: Tryptophan Depletion and Kynurenine Accumulation

Immunoregulation by tryptophan metabolism modulates the immune system by depletion of the TDO/IDO substrate (tryptophan) in the microenvironment and the accumulation of products such as kynurenine.

Effector T cells are particularly susceptible to low tryptophan concentrations, therefore, depletion of the essential amino acid tryptophan from the local microenvironment resulting in effector T-cell anergy and apoptosis. The depletion of tryptophan is detected by the general control non-derepressible-2 kinase (GCN2) (Munn et al., 2005). The activation of GCN2 triggers a stress-response program that results in cell-cycle arrest, differentiation, adaptation or apoptosis. T cells lacking GCN2 in mice are not susceptible to IDO-mediated anergy by myeloid cells, including dendritic cells in tumor-draining lymph nodes (Munn et al., 2005).

Tryptophan metabolites such as kynurenine, kynurenic acid, 3-hydroxy-kynurenine, and 3-hydroxy-anthranilic acid suppress T-cell function and are capable of inducing T-cell apoptosis. Recent studies have shown that the aryl hydrocarbon receptor (AHR) is a direct target of kynurenine (Mezrich et al., 2010; Nguyen et al., 2010; Opitz et al., 2011). The AHR is a basic helix-loop-helix Per-Arnt-Sim (PAS) family transcription factor. As kynurenine accumulates in a tumour, KYN binds the AHR, translocates to the nucleus and activates transcription of target genes regulated by dioxin-responsive elements (DREs). In T-helper-cells kynurenine results in the generation of regulatory T cells (Treg).

Pharmacological inhibitors of TDO and/or IDO have utility in a wide range of indications, including Infectious diseases, cancer, neurological conditions and many other diseases.

Infectious Diseases and Inflammation

Infection by bacteria, parasites, or viruses induces a strong IFN-γ-dependent inflammatory response. IDO can dampen protective host immunity, thus indirectly leading to increased pathogen burdens. For example, IDO activity attenuates *Toxoplasma gondii* replication in the lung, and the inflammatory damage is significantly decreased by the administration of the IDO inhibitor 1 MT after infection (Murakami et al., 2012). Also, in mice infected with murine leukaemia virus (MuLV), IDO was found to be highly expressed, and ablation of IDO enhanced control of viral replication and increased survival (Hoshi et al., 2010). In a model of influenza infection, the immunosuppressive effects of IDO could predispose lungs to secondary bacterial infection (van der Sluijs, et al 2006). In Chagas Disease, which is caused by the *Trypanosoma cruzi* parasite, kynurenine is increased in patients and correlates with disease severity (Maranon et al., 2013). Therefore, IDO inhibitors could be used to improve the outcomes of patients with a wide variety of infectious diseases and inflammatory conditions. Given the role of TDO in controlling systemic Trp levels, TDO inhibitors could also be used to improve the outcomes of patients with a wide variety of infectious diseases and inflammatory conditions.

IDO and Immunity to Gut Bacteria

IDO plays a role in regulating mucosal immunity to the intestinal microbiota. IDO has been shown to regulate commensal induced antibody production in the gut; IDO-deficient mice had elevated baseline levels of immunoglobulin A (IgA) and immunoglobulin G (IgG) in the serum and increased IgA in intestinal secretions. Due to elevated antibody production, IDO deficient mice were more resistant to intestinal colonization by the gram-negative enteric bacterial pathogen *Citrobacter rodentium* than WT mice. IDO-deficient mice also displayed enhanced resistance to the colitis caused by infection with *C. rodentium* (Harrington et al., 2008).

Therefore, pharmacological targeting of IDO activity may represent a new approach to manipulating intestinal immunity and controlling the pathology caused by enteric pathogens including colitis (Harrington et al., 2008).

HIV Infection

Patients infected with HIV have chronically reduced levels of plasma tryptophan and increased levels of kynurenine, and increased IDO expression (Fuchs et al., 1990 and Zangerle et al., 2002).

In HIV patients the upregulation of IDO acts to suppress immune responses to HIV antigens contributing to the immune evasion of the virus. HIV triggers high levels of IDO expression when it infects human macrophages in vitro (Grant et al., 2000), and simian immunodeficiency virus (SIV) infection of the brain in vivo induces IDO expression by cells of the macrophage lineage (Burudi et al., 2002).

The pathogenesis of HIV is characterized by CD4+ T cell depletion and chronic T cell activation, leading ultimately to AIDS (Douek et al., 2009). CD4+T helper (TH) cells provide protective immunity and immune regulation through different immune cell functional subsets, including TH1, TH2, T regulatory (Treg), and TH17 cells. Progressive HIV is associated with the loss of TH17 cells and a reciprocal increase in the fraction of the immunosuppressive Treg cells. The loss of TH17/Treg balance is associated with induction of IDO by myeloid antigen-presenting dendritic cells (Favre et al., 2010). In vitro, the loss of TH17/Treg balance is mediated directly by the proximal tryptophan catabolite from IDO metabolism, 3-hydroxyanthranilic acid. Therefore in progressive HIV, induction of IDO contributes to the inversion of the TH17/Treg balance and maintenance of a chronic inflammatory state (Favre et al., 2010). Therefore, IDO inhibitors could have utility in addressing the TH17/Treg balance in HIV.

Sepsis-Induced Hypotension

Systemic inflammation such as sepsis is characterized by arterial hypotension and systemic inflammatory response syndrome (Riedemann et al., 2003). The associated increase in circulating pro-inflammatory cytokines, including interferon-γ (IFN-γ), leads to the unchecked production of effector molecules such as reactive oxygen and nitrogen species that themselves can contribute to pathology (Riedemann et al., 2003).

The metabolism of tryptophan to kynurenine by IDO expressed in endothelial cells contributes to arterial vessel relaxation and the control of blood pressure (Wang et al., 2010). Infection of mice with malarial parasites (*Plasmodium berghei*), and experimental induction of endotoxemia, caused endothelial expression of IDO, resulting in decreased plasma tryptophan, increased kynurenine, and hypotension. Pharmacological inhibition of IDO increased blood pressure in systemically inflamed mice, but not in mice deficient for IDO or interferon-γ, which is required for IDO induction. Arterial relaxation by kynurenine was mediated by activation of the adenylate and soluble guanylate cyclase pathways. (Wang et al., 2010). Therefore, inhibitors of IDO (and TDO, given its role in controlling systemic Trp levels) could have utility in treating sepsis-induced hypotension.

CNS Disorders

In the central nervous system both fates of TRP which act as a precursor to kynurenine and serotonin are pathways of interest and importance. Metabolites produced by the kynurenine pathway have been implicated to play a role in the pathomechanism of neuroinflammatory and neurodegenerative disorder (summarised in FIG. 2). The first stable intermediate from the kynurenine pathway is KYN. Subsequently, several neuroactive intermediates are generated. They include kynurenic acid (KYNA), 3-hydroxykynurenine (3-HK), and quinolinic acid (QUIN). 3-HK and QUIN are neurotoxic by distinct mechanisms; 3-HK is a potent free-radical generator (Hiraku et al., 1995; Ishii et al., 1992; Thevandavakkam et al., 2010), whereas QUIN is an excitotoxic N-methyl-D-aspartate (NMDA) receptor agonist (Schwarcz et al., 1983; Stone and Perkins, 1981). KYNA, on the other hand, has neuroprotective properties as an antagonist of excitatory amino acid receptors and a free-radical scavenger (Carpenedo et al., 2001; Foster et al., 1984; Goda et al., 1999; Vecsei and Beal, 1990). Changes in the concentration levels of kynurenines can shift the balance to pathological conditions. The ability to influence the metabolism towards the neuroprotective branch of the kynurenine pathway, i.e. towards kynurenic acid (KYNA) synthesis, may be one option in preventing neurodegenerative diseases.

In the CNS, the kynurenine pathway is present to varying extents in most cell types, Infiltrating macrophages, activated microglia and neurons have the complete repertoire of kynurenine pathway enzymes. On the other hand, neuroprotective astrocytes and oligodendrocytes lack the enzyme, kynurenine 3-monooxygenase (KMO) and IDO respectively, and are incapable of synthesizing the excitotoxin, quinolinic acid (QUIN) (Guillemin et al., 2000; Lim et al., 2007). TDO is expressed in low quantities in the brain, and is induced by TRP or corticosteroids (Salter and Pogson 1985; Miller et al., 2004).

Given the role of TDO and IDO in the pathogenesis of several CNS disorders as well as the role of TDO in controlling systemic Trp levels, IDO and/or TDO inhibitors could be used to improve the outcomes of patients with a wide variety of CNS diseases and neurodegeneration.

Amyotrophic Lateral Sclerosis

Amyotrophic lateral sclerosis (ALS), or Lou Gehrig's disease, is a progressive and fatal neurodegenerative disease targeting the motor system. ALS results in the selective attacking and destruction of motor neurons in the motor cortex, brainstem and spinal cord.

Although multiple mechanisms are likely to contribute to ALS, the kynurenine pathway activated during neuroinflammation is emerging as a contributing factor. Initial inflammation may inflict a nonlethal injury to motor neurons of individuals with a susceptible genetic constitution, in turn triggering a progressive inflammatory process which activates microglia to produce neurotoxic kynurenine metabolites that further destroy motor neurons.

In the brain and spinal cord of ALS patients large numbers of activated microglia, reactive astrocytes, T cells and infiltrating macrophages have been observed (Graves et al., 2004; Henkel et al., 2004). These cells release inflammatory and neurotoxic mediators, among others IFN-γ, the most potent inducer of IDO (McGeer and McGeer 2002). The neuronal and microglial expression of IDO is increased in ALS motor cortex and spinal cord (Chen et al., 2010). It has been proposed that the release of immune activating agents activates the rate-limiting enzyme of the KP, IDO, which generates metabolites such as the neurotoxin QUIN. Therefore, inhibition of IDO would reduce the synthesis of neurotoxic QUIN, which has been clearly implicated in the pathogenesis of ALS.

Huntington's Disease

Huntington's disease (HD) is a genetic autosomal dominant neurodegenerative disorder caused by expansion of the CAG repeats in the huntingtin (htt) gene. Patients affected by HD display progressive motor dysfunctions characterized by abnormality of voluntary and involuntary movements (choreoathetosis) and psychiatric and cognitive disturbances. In-life monitoring of metabolites within the KYN pathway provide one of the few biomarkers that correlates with the number of CAG repeats and hence the severity of the disorder (Forrest et al., 2010). Post mortem very high levels of QUIN are found located in areas of neurodegeneration, while striatal glutamatergic neurones, on which QUIN acts as an excitotoxin, are a principal class lost in the disease. Importantly, TDO ablation in a *Drosophila* model of Huntington's disease ameliorated neurodegeneration (Campesan et al., 2011).

Alzheimer's Disease

Alzheimer's disease (AD) is an age-related neurodegenerative disorder characterised by neuronal loss and dementia. The histopathology of the disease is manifested by the accumulation of intracellular β-amyloid (Aβ) and subsequent formation of neuritic plaques as well as the presence of neurofibrillary tangles in specific brain regions associated with learning and memory. The pathological mechanisms underlying this disease are still controversial, however, there is growing evidence implicating KP metabolites in the development and progression of AD.

It has been shown that Aβ (1-42) can activate primary cultured microglia and induce IDO expression (Guillemin et al., 2003; Walker et al., 2006). Furthermore, IDO over-expression and increased production of QUIN have been observed in microglia associated with the amyloid plaques in the brain of AD patients (Guillemin et al., 2005). QUIN has been shown to lead to tau hyperphosphorylation in human cortical neurons (Rahman et al., 2009). Thus, over-expression of IDO and over-activation of the KP in microglia are implicated in the pathogenesis of AD.

There is also evidence for TDO involvement in Alzheimer's disease. TDO is upregulated in the brain of patients and AD mice models. Furthermore, TDO co-localizes with quinolinic acid, neurofibrillary tangles-tau and amyloid deposits in the hippocampus of AD patients (Wu et al., 2013). Therefore, the kynurenine pathway is over-activated in AD by both TDO and IDO and may be involved in neurofibrillary tangle formation and associated with senile plaque formation.

Psychiatric Disorders and Pain

Most tryptophan is processed through the kynurenine pathway. A small proportion of tryptophan is processed to 5-HT and hence to melatonin, both of which are also substrates for IDO. It has long been known that amongst other effects acute tryptophan depletion can trigger a depressive episode and produces a profound change in mood even in healthy individuals. These observations link well with the clinical benefits of serotonergic drugs both to enhance mood and stimulate neurogenesis.

The co-morbidity of depressive symptoms, implication of the kynurenine pathway in inflammation and an emerging link between TDO and the glucocorticoid mediated stress response also implicate a role in the treatment of chronic pain (Stone and Darlington 2013).

Schizophrenic patients exhibit elevated KYN levels both in CSF and brain tissue, particularly the frontal cortex. This has been associated with the "hypofrontality" observed in schizophrenia. Indeed rodents treated with neuroleptics show a marked reduction in frontal KYN levels. These changes have been associated with reduced KMO and 3HAO. Evidence includes an association between a KMO polymorphism, elevated CSF KYN and schizophrenia (Holtze etr al., 2012). Taken together there is potential for manipulations in this pathway to be both pro-cognate and neuroleptic.

Pain and depression are frequently comorbid disorders. It has been shown that IDO plays a key role in this comorbidity. Recent studies have shown that IDO activity is linked to (a) decreased serotonin content and depression (Dantzer et al., 2008; Sullivan et al., 1992) and (b) increased kynurenine content and neuroplastic changes through the effect of its derivatives such as quinolinic acid on glutamate receptors (Heyes et al., 1992).

In rats chronic pain induced depressive behaviour and IDO upregulation in the bilateral hippocampus. Upregulation of IDO resulted in the increased kynurenine/tryptophan ratio and decreased serotonin/tryptophan ratio in the bilateral hippocampus. Furthermore, IDO gene knockout or pharmacological inhibition of hippocampal IDO activity attenuated both nociceptive and depressive behaviour (Kim et al., 2012).

Since proinflammatory cytokines have been implicated in the pathophysiology of both pain and depression, the regulation of brain IDO by proinflammatory cytokines serves as a critical mechanistic link in the comorbid relationship between pain and depression through the regulation of tryptophan metabolism.

Multiple Sclerosis

Multiple sclerosis (MS) is an autoimmune disease characterized by inflammatory lesions in the white matter of the nervous system, consisting of a specific immune response to the myelin sheet resulting in inflammation and axonal loss (Trapp et al., 1999; Owens, 2003).

Accumulation of neurotoxic kynurenine metabolites caused by the activation of the immune system is implicated in the pathogenesis of MS. QUIN was found to be selectively elevated in the spinal cords of rats with EAE, an autoimmune animal model of MS (Flanagan et al., 1995). The origin of the increased QUIN in EAE was suggested to be the macrophages. QUIN is an initiator of lipid peroxidation and high local levels of QUIN near myelin may contribute to the demyelination in EAE and possibly MS.

Interferon beta 1b (IFN-β1b) induces KP metabolism in macrophages at concentrations comparable to those found in the sera of IFN-b treated patients, this which may be a limiting factor in its efficacy in the treatment of MS (Guillemin et al., 2001). After IFN-β administration, increased kynurenine levels and kynurenine/tryptophan ratio were found in the plasma of MS patients receiving IFN-b injection compared to healthy subjects indicating an induction of IDO by IFN-β (Amirkhani et al., 2005). IFN-β1b, leads to production of QUIN at concentrations sufficient to disturb the ability of neuronal dendrites to integrate incoming signals and kill oligodendrocytes (Cammer 2001). In IFN-β1b-treated patients concomitant blockade of the KP with an IDO/TDO inhibitor may improve its efficacy of IFN-β1b.

Parkinson's Disease

Parkinson's disease (PD) is a common neurodegenerative disorder characterised by loss of dopaminergic neurons and localized neuroinflammation.

Parkinson's disease is associated with chronic activation of microglia (Gao and Hong, 2008). Microglia activation release neurotoxic substances including reactive oxygen species (ROS) and proinflammatory cytokines such as INF-γ (Block et al., 2007), a potent activator of KP via induction of IDO expression. KP in activated microglia leads to upregulation of 3 HK and QUIN. 3 HK is toxic primarily as a result of conversion to ROS (Okuda et al., 1998). The combined effects of ROS and NMDA receptor-mediated excitotoxicity by QUIN contribute to the dysfunction of neurons and their death (Braidy et al., 2009; Stone and Perkins, 1981). However, picolinic acid (PIC) produced through KP activation in neurons, has the ability to protect neurons against QUIN-induced neurotoxicity, being NMDA agonist (Jhamandas et al., 1990). Microglia can become overactivated, by proinflammatory mediators and stimuli from dying neurons and cause perpetuating cycle of further microglia activation microgliosis. Excessive microgliosis will cause neurotoxicity to neighbouring neurons and resulting in neuronal death, contributing to progression of Parkinson's disease. (Zinger et al 2011): Therefore, PD is associated with an imbalance between the two main branches of the KP within the brain. KYNA synthesis by astrocytes is decreased and concomitantly, QUIN production by microglia is increased.

HIV

HIV patients, particularly those with HIV-linked dementia (Kandanearatchi & Brew 2012), often have significantly elevated KYN levels in CSF. These levels are directly related to the development of neurocognitive decline and often the presence of sever psychotic symptoms (Stone & Darlington 2013).

Cancer

It is clear that tumours can induce tolerance to their own antigens. Tryptophan catabolism in cancer is increasingly being recognized as an important micro-environmental factor that suppresses antitumor immune responses. Depletion of tryptophan and accumulation of immunosuppressive tryptophan catabolites such as kynurenine create an immunosuppressive milieu in tumours and in tumour-draining lymph nodes by inducing T-cell anergy and apoptosis. Such immunosuppression in the tumour microenvironment may help cancers evade the immune response and enhance tumorigenicity (reviewed in Adam et al., 2012).

Recently, both TDO and IDO have been implicated in tumour progression. Individually TDO or IDO have been found to be overexpressed in various cancers, furthermore, several cancers overexpress both TDO and IDO. TDO and IDO mediate immunosuppressive effects through the metabolization of Trp to kynurenine, triggering downstream signalling through GCN2, mTOR and AHR that can affect differentiation and proliferation of T cells. Also, expression of IDO by activated dendritic cells can serve to activate regulatory T cells (Tregs) and inhibit tumor-specific effector CD8+ T cells, thereby constituting a mechanism by which the immune system can restrict excessive lymphocyte reactivity (reviewed in Platten et al., 2012).

IDO

Increased expression of IDO has been shown to be an independent prognostic variable for reduced survival in patients with acute myeloid leukemia (AML), small-cell lung, melanoma, ovarian, colorectal, pancreatic, and endometrial cancers (Okamoto et al., 2005; Ino et al., 2006). Indeed, sera from cancer patients have higher kynurenine/tryptophan ratios than sera from normal volunteers (Liu et al., 2010; Weinlich et al., 2007; Huang et al., 2002). The level of IDO expression was also shown to correlate with the number of tumour infiltrating lymphocytes in colorectal carcinoma patients (Brandacher et al., 2006).

In preclinical models, transfection of immunogenic tumour cells with recombinant IDO prevented their rejection in mice (Uyttenhove et al., 2003). While, ablation of IDO expression led to a decrease in the incidence and growth of 7,12-dimethylbenz(a)anthracene-induced premalignant skin papillomas (Muller et al., 2008). Moreover, IDO inhibition slows tumour growth and restores anti-tumour immunity (Koblish et al., 2010) and IDO inhibition synergises with cytotoxic agents, vaccines and cytokines to induce potent anti-tumour activity (Uyttenhove et al., 2003; Muller et al., 2005; Zeng et al., 2009).

TDO

TDO is predominantly expressed in the liver and is believed to regulate systemic Trp concentrations, however, TDO was found to be frequently activated and constitutively expressed in glioma cells. TDO derived KYN was shown to suppress antitumor immune responses and promote tumor-cell survival and motility through the AhR in an autocrine manner (Opitz et al., 2011). It was also shown that TDO is elevated in human hepatocellular carcinomas and detected sporadically in other cancers. In a preclinical model, TDO expression prevented rejection of tumor grafts by preimmunized mice. Systemic administration of the TDO inhibitor, LM10, restored the ability of mice to reject TDO-expressing tumors (Pilotte et al., 2012).

Therefore inhibitors of TDO or IDO could have wide ranging therapeutic efficacy in the treatment of cancer. Also dual inhibitors blocking both TDO and IDO may demonstrate improved clinical efficacy by targeting both of these key Trp-metabolising enzymes and would also treat a wider patient population: in a series of 104 human tumor lines of various histological types, 20 tumors expressed only TDO, 17 expressing only IDO and 16 expressed both. Therefore, targeting both IDO and TDO would allow reaching 51% of tumors instead of 32% with IDO or 35% with TDO alone (Pilotte et al., 2012). Moreover, given the role of TDO in controlling systemic Trp levels, TDO inhibitors could also be used to improve the outcomes of patients with a wide variety of cancers and neoplastic diseases that do not express TDO.

Inhibition of IDO and/or TDO will dramatically lower kynurenine levels, relieving the brake on the immune system allowing it to attack and eliminate tumours. While there is evidence that a TDO/IDO inhibitor would be useful as a stand-alone agent, inhibitors of this type would be particularly effective when used in combination with other cancer immunotherapies. In fact, upregulation of IDO expression has been identified as a mechanism by which tumours gain resistance to the CTLA-4 blocking antibody ipilimumab. Ipilimumab blocks the co-stimulatory molecule CTLA-4, causing tumour-specific T cells to remain in an activated state. IDO knockout mice treated with anti-CTLA-4 antibody demonstrate a striking delay in B16 melanoma tumor growth and increased overall survival when compared with wild-type mice.

Also, CTLA-4 blockade strongly synergizes with IDO inhibitors to mediate tumour rejection. Similar data was also reported for IDO inhibitors in combination with anti-PD1 and anti-PDL-1 antibodies (Holmgaard et al., 2013).

Agents that will influence an immunosuppressive environment may also be relevant to chimeric antigen receptor T cell therapy (CAR-T) therapies to enhance efficacy and patient responses.

Other Diseases

Although these effects are defensive strategies to cope with infection and inflammation, they may have unintended consequences because kynurenines formed during IDO and TDO-mediated degradation of tryptophan can chemically modify proteins and have been shown to be cytotoxic (Morita et al., 2001; Okuda et al., 1998). In coronary heart disease, inflammation and immune activation are associated with increased blood levels of kynurenine (Wirleitner et al., 2003) possibly via interferon-γ-mediated activation of IDO. In experimental chronic renal failure, activation of IDO leads to increased blood levels of kynurenines (Tankiewicz et al., 2003), and in uremic patients kynurenine-modified proteins are present in urine (Sala et al., 2004). Further, renal IDO expression may be deleterious during inflammation, because it enhances tubular cell injury.

General anaesthesia unfortunately mimics many of these effects inducing stress and inflammatory processes. Post anaesthesia cognitive dysfunction has often been correlated with these sequelae. Recently these deficits have been shown to be correlated with changes in kynurenine pathway markers, but not cytokines, following cardiac surgery and in recovering stroke patients (Stone and Darlington 2013).

Cataracts

A cataract is a clouding of the lens inside the eye that leads to a decrease in vision. Recent studies suggest that kynurenines might chemically alter protein structure in the human lens leading to cataract formation. In the human lens IDO activity is present mainly in the anterior epithelium (Takikawa et al., 1999). Several kynurenines, such as kynurenine (KYN), 3-hydroxykynurenine (3OHKYN), and 3-hydroxykynurenine glucoside (3OHKG) have been detected in the lens; where they were thought to protect the retina by absorbing UV light and therefore are commonly referred to as UV filters. However, several recent studies show that kynurenines are prone to deamination and oxidation to form α,β-unsaturated ketones that chemically react and modify lens proteins (Taylor et al., 2002). Kynurenine mediated modification could contribute to the lens protein modifications during aging and cataractogenesis. They may also reduce the chaperone function of α-crystallin, which is necessary for maintaining lens transparency.

Transgenic mouse lines that overexpress human IDO in the lens developed bilateral cataracts within 3 months of birth. It was demonstrated that IDO-mediated production of kynurenines results in defects in fibre cell differentiation and their apoptosis (Mailankot et al., 2009). Therefore inhibition of IDO may slow the progression of cataract formation.

Female Reproductive Health

Endometriosis

Endometriosis, the presence of endometrium outside the uterine cavity, is a common gynaecological disorder, causing abdominal pain, dyspareunia and infertility. IDO expression was found to be higher in eutopic endometrium from women with endometriosis by microarray analysis (Bumey et al., 2007 and Aghajanova et al., 2011). Furthermore, IDO was shown to enhance the survival and invasiveness of endometrial stromal cells (Mei et al., 2013). Therefore, an IDO/TDO inhibitor could be used as a treatment for endometriosis.

Contraception and Abortion

The process of implantation of an embryo requires mechanisms that prevent allograft rejection; and tolerance to the fetal allograft represents an important mechanism for maintaining a pregnancy. Cells expressing IDO in the foeto-maternal interface protect the allogeneic foetus from lethal rejection by maternal immune responses. Inhibition of IDO by exposure of pregnant mice to 1-methyl-tryptophan induced a T cell-mediated rejection of allogeneic concepti, whereas syngeneic concepti were not affected; this suggests that IDO expression at the foetal-maternal interface is necessary to prevent rejection of the foetal allograft (Munn et al, 1998). Accumulating evidence indicates that IDO production and normal function at the foetal-maternal interface may play a prominent role in pregnancy tolerance (Durr and Kindler, 2013). Therefore, an IDO/TDO inhibitor could be used as a contraceptive or abortive agent.

On the above basis, the inventors have determined that a strong rationale exists for the therapeutic utility of drugs which block the activity of TDO and or IDO, in treating the above-mentioned diseases, conditions and disorders.

US 2007/0167426 discloses compounds for the treatment of inflammatory disorders and microbial diseases. A large variety of compounds are disclosed, some of which are compounds loosely similar to those identified by the inventors as potentially useful in the present context. However, this document indicates that these compounds are inhibitors of matrix metalloproteinases (MMPs), a disintegrin and metalloproteases (ADAMs), aggrecanase or aggrecan degrading metalloprotease (ADMP) and/or tumor necrosis factor alpha converting enzyme (TACE) (and in so doing prevent the release of TNF-α). TDO and IDO inhibition are not considered.

EP 1,069,124 discloses 2-benzimidazoleamine compounds as ORL-1 receptor agonists. A large variety of compounds are again disclosed, some of which are compounds loosely similar to those identified by the inventors as potentially useful in the present context. In common with US 2007/0167426, in this document TDO and IDO inhibition are not considered.

Having regard to the above, it is an aim of the present invention to provide TDO or IDO inhibitors, and in particular TDO and IDO inhibitors for use in medicine. It is a further aim to provide pharmaceutical compositions comprising such inhibitors, and in particular to provide compounds and pharmaceutical compositions for treating a cancer, an inflammatory condition, an infectious disease, a central nervous system disease or disorder and other diseases, conditions and disorders. It is also an aim to provide compounds methods of synthesis of the compounds.

Accordingly, the present invention provides a tryptophan-2,3-dioxygenase (TDO) and/or indoleamine-2,3-dioxygenase (IDO) inhibitor compound for use in medicine, which compound comprises the following formula:

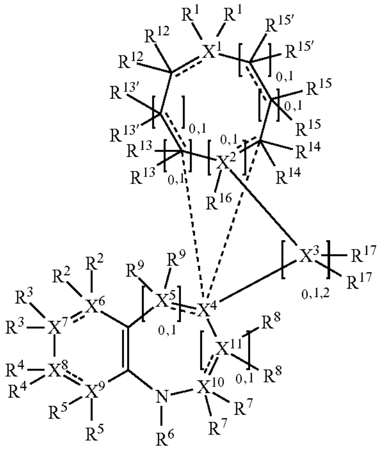

wherein $X^2$, $X^4$, $X^{10}$, and $X^{11}$ may be the same or different and each is independently selected from C and N; $X^1$, $X^3$, $X^5$, $X^6$, $X^7$, $X^8$, and $X^9$ may be the same or different and each is independently selected from C, N and O; each bond having a dotted line may independently be a double bond or a single bond, provided that valencies at each atom are maintained; the dotted lines joining $X^4$ with the carbon atoms either side of $X^2$ are single bonds, and are only present when $X^2$ is absent, $X^3$ is absent and $X^4$ is C, and when these bonds are present the ring carbons on each side of $X^2$ are not directly bonded to each other; each $R^1$ may be present or absent and may be the same or different and is selected from H and a substituted or unsubstituted organic group, provided that the number of $R^1$ groups present is such that the valency of $X^1$ is maintained; each $R^{12}$, $R^{13}$, $R^{13'}$, $R^{14}$, $R^{15}$ and $R^{15'}$ may be present or absent and may be the same or different and each is independently selected from H and a substituted or unsubstituted organic group, provided that the number of such R groups present is such that the valency of the ring carbon atoms is maintained; $R^{16}$ may be present or absent and is selected from H and a substituted or unsubstituted organic group, provided that the number of $R^{16}$ groups present is such that the valency of $X^2$ is maintained; each $R^{17}$ may be present or absent and may be the same or different and is independently selected from H and a substituted or unsubstituted organic group, provided that the number of $R^{17}$ groups present is such that the valency of $X^3$ is maintained; each $R^2$, $R^3$, $R^4$, and $R^5$ may be present or absent and may be the same or different and is selected from H and a substituted or unsubstituted organic group, provided that the number of such R groups present is such that the valencies of $X^6$, $X^7$, $X^8$, and $X^9$ are maintained; each $R^7$, $R^8$ and $R^9$ may be present or absent and may be the same or different and is selected from H and a substituted or unsubstituted organic group, provided that the number of such R groups present is such that the valencies of $X^{10}$, $X^{11}$, and $X^5$ are maintained; and $R^6$ is selected from H and a substituted or unsubstituted organic group, preferably H and a substituted or unsubstituted $C_1$-$C_6$ alkyl group; and wherein any R group may form a ring with any other R group on an adjacent and/or proximal atom.

In the present context the dotted line between two atoms indicates the possible presence of a further bond. In a case where two atoms are already joined by a solid line, but also have a dotted line, then those atoms have at least a single bond, but possibly a double bond in some cases. Thus, in such cases, each atom having a dotted line may independently have a double bond or a single bond, provided that valencies at each atom are maintained. In cases where there is only a dotted line joining two atoms, then these atoms may not be directly bonded at all in some cases, or in other cases may be joined by a single bond.

In the present context the part of the structure present in square brackets may be repeated the number of times given by the numbers next to the square brackets. For example, in the case of $[X(R)]_{0,1,2}$ the X—R group may be absent, present once: —X(R)—; or present twice: —X(R)—X(R)—.

In the context of the present invention, maintaining the valency means ensuring that an atom has its normal (typically most common) valency in organic compounds (i.e. 2 for oxygen, 3 for nitrogen and 4 for carbon). Nitrogen atoms may, in some instances, have 4 bonds, but in such cases they are typically positively charged such that the compound may have a counter-ion. Such compounds are also considered to be part of the invention, and in these cases, due to the positive charge, it will be clear that the nitrogen atom still maintains its normal valency of 3. For the avoidance of doubt, where the number of R groups may vary according to the choice of X group, it may vary as follows.

Each $R^1$ may be the same or different, provided that $R^1$ is absent when $X^1$ is N and is double bonded to a ring carbon and when $X^1$ is O, one $R^1$ is present when $X^1$ is N and is not double bonded to a ring carbon or when $X^1$ is C and is double bonded to a ring carbon, and two $R^1$ are present when $X^1$ is C and is not double bonded to a ring carbon. Preferably $R^1$ (or at least one $R^1$ if there are two such groups) is not H.

Each $R^{12}$, $R^{13}$, $R^{13'}$, $R^{14}$, $R^{15}$ and $R^{15'}$ may be the same or different, provided that when such an R group is attached to a ring carbon having a double bond, only one such R group is present, and when such an R group is attached to a ring carbon having no double bond, two such R groups are present.

When $X^2$ is a ring carbon having a double bond, or is N, $R^{16}$ is absent, and when $X^2$ is attached is a carbon having no double bond $R^{16}$ is present.

Each $R^{17}$ may be the same or different, provided that when $X^3$ is O, $R^{17}$ is absent, when $X^3$ is N, only one $R^{17}$ is present, and when $X^3$ is C, two $R^{17}$ are present. In some cases there may be two $X^3$ atoms. In this case each $X^3$ is may be singly bonded or doubly bonded to the other, and may be C or N and the number of $R^{17}$ groups present will be in accordance with the valencies of each $X^3$, as above.

Each $R^2$, $R^3$, $R^4$, and $R^5$ may be the same or different, provided that when such an R group is attached to a ring nitrogen having a double bond or to a ring oxygen the R group is absent, when such an R group is attached to a ring carbon having a double bond or to a ring nitrogen having no double bond only one such R group is present, and when such an R group is attached to a ring carbon having no double bond two such R groups are present.

Each $R^7$, $R^8$ and $R^9$ may be the same or different, provided that when such an R group is attached to a ring nitrogen having a double bond the R group is absent, when such an R group is attached to a ring carbon having a double bond or to an N having no double bond only one such R group is present, and when such an R group is attached to a ring carbon having no double bond two such R groups are present. In the case of $R^9$ it is absent when its ring atom is an O.

Any R group may form a ring with any other R group on an adjacent and/or proximal atom. Thus, the following substituents may together form a ring: $R^1$ and $R^{15'}$, $R^1$ and $R^{15}$, $R^1$ and $R^{14}$, $R^1$ and $R^{12}$ and $R^{13'}$, $R^{12}$ and $R^{13}$, $R^{12}$ and $R^{16}$, $R^{13'}$ and $R^{13}$, and $R^{16}$, $R^{14}$ and $R^{16}$, $R^{14}$ and $R^{15}$, $R^{14}$ and $R^{15'}$, $R^{15}$ and $R^{15'}$, $R^2$ and $R^3$, $R^2$ and $R^9$, $R^3$ and $R^4$, $R^4$ and $R^5$, $R^5$ and $R^6$, $R^6$ and $R^7$, and/or $R^7$ and $R^8$. In the context of the present invention, an adjacent and/or proximal atom may mean another atom directly bonded to an atom (adjacent), or may be two atoms with only a single atom in between (proximal), or may mean two atoms close enough sterically to be capable of forming a ring (proximal). Accordingly the definition includes $R^2$ and $R^9$. Preferably R groups attached to the same atom do not together form a ring, although this is not excluded. Preferably $R^6$ does not form a ring with another R group, and typically $R^6$ is a substituted or unsubstituted lower ($C_1$-$C_6$) alkyl group, more typically unsubstituted and most typically H or Me.

In any compound where there are two R groups attached to the same atom, the invention includes compounds in which two R groups together form a group which is double bonded to that atom. Accordingly, two R groups attached to the same atom may together form a =O group, or a $=C(R')_2$ group (wherein each R' group is the same or different and is H or an organic group, preferably H or a straight or branched $C_1$-$C_6$ alkyl group). This is more typical in cases where the R groups are attached to a C atom, such that together they form a C=O group or a $C=C(R')_2$ group. $R^7$, $R^{12}$, $R^{15}$, $R^{15'}$ and $R^{17}$ may thus typically be =O groups, as may $R^2$, $R^3$, $R^4$, $R^5$, $R^8$, $R^9$, $R^{13}$, $R^{13'}$ and $R^{14}$.

In the context of the present invention, a compound is considered to be a TDO inhibitor if its presence is capable of preventing, reducing or slowing the conversion of tryptophan into N-formylkynurenine by TDO as compared to the same conversion in its absence. Similarly, in the context of the present invention, a compound is considered to be an IDO inhibitor if its presence is capable of preventing, reducing or slowing the conversion of tryptophan into N-formylkynurenine by IDO as compared to the same conversion in its absence. The compounds of the invention may be selective TDO inhibitors, or selective IDO inhibitors, or may be inhibitors of both IDO and TDO.

In typical embodiments, the invention provides a compound as defined above comprising one or other of the following formulae:

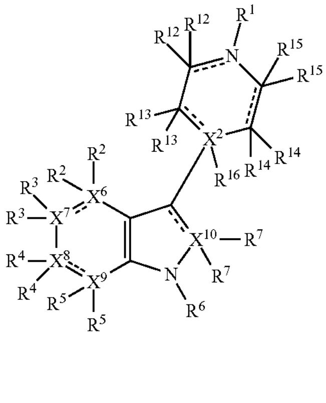

-continued

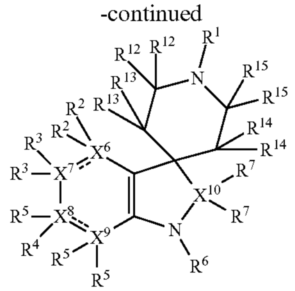

where each of the variables has the same meaning as above. Thus, in typical embodiments the compound may take the form of substituted indole compounds where the substituent is a nitrogen-containing heterocyclic ring, or a nitrogen-containing spiro compound. In more typical embodiments, the nitrogen-containing spiro compound comprises the following formula:

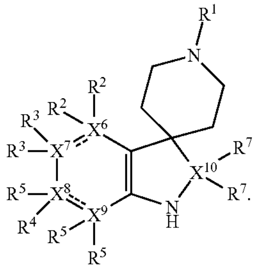

In typical embodiments of the invention, the bonds between $X^6$ and $X^7$, and/or between $X^8$ and $X^9$ are double bonds. Where one such X has a double bond it is selected from C and N (and not O). It is especially advantageous that both such bonds are double bonds. Thus, more typically the present invention provides a compound, which compound comprises the following formula:

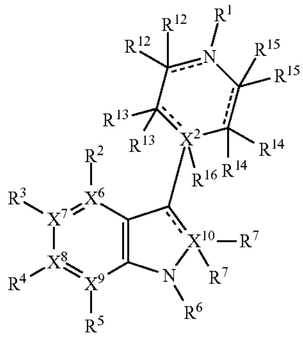

wherein $X^2$ $X^6$, $X^7$, $X^8$, $X^9$ and $X^{10}$ may be the same or different and each is independently selected from C and N; each bond having a dotted line may independently be a double bond or a single bond, provided that the valencies at each atom are maintained; $R^1$ may be present or absent and is selected from H and a substituted or unsubstituted organic group, provided that the number of $R^1$ groups present is such that the valency of $X^1$ is maintained; each $R^{12}$, $R^{13}$, $R^{14}$, and $R^{15}$ may be present or absent and may be the same or different and each is independently selected from H and a substituted or unsubstituted organic group, provided that the number of such R groups present is such that the valency of the ring carbon atoms is maintained; $R^{16}$ may be present or absent and is selected from H and a substituted or unsubstituted organic group, provided that the number of $R^{16}$ groups present is such that the valency of $X^2$ is maintained; each $R^2$, $R^3$, $R^4$, and $R^5$ may be present or absent and may be the same or different and is selected from H and a substituted or unsubstituted organic group, provided that the number of such R groups present is such that the valencies of $X^6$, $X^7$, $X^8$, and $X^9$ are maintained; $R^6$ is selected from H and a substituted or unsubstituted organic group, preferably H and a substituted or unsubstituted $C_1$-$C_6$ alkyl group; and each $R^7$ may be present or absent and may be the same or different and each is independently selected from H and a substituted or unsubstituted organic group, provided that the number of $R^7$ groups present is such that the valency of $X^{10}$ is maintained.

In the context of the present invention, maintaining the valency means ensuring that an atom has its normal (typically most common) valency in organic compounds (i.e. 3 for nitrogen and 4 for carbon). Nitrogen atoms may, in some instances, have 4 bonds, but in such cases they are typically positively charged such that the compound may have a counter-ion. Such are also be part of the invention, and in these cases, due to the positive charge, it will be clear that the nitrogen atom still maintains its normal valency of 3. For the avoidance of doubt, where the number of R groups may vary according to the choice of X group, it may vary as follows.

$R^1$ is present when the N to which it is attached is not double bonded to a ring carbon and is absent when the N to which it is attached is double bonded to a ring carbon.

Each $R^{12}$, $R^{13}$, $R^{14}$, and $R^{15}$ may be the same or different, provided that when such an R group is attached to a ring carbon having a double bond, only one such R group is present, and when such an R group is attached to a ring carbon having no double bond, two such R groups are present.

$R^{16}$ may be present or absent, provided that when $X^2$ is a ring carbon having a double bond, or is N, $R^{16}$ is absent, and when $X^2$ is a carbon having no double bond $R^{16}$ is present.

Each of $R^2$, $R^3$, $R^4$, and $R^5$ independently may be present or absent, provided that $R^2$ is present when $X^6$ is a C and is absent when $X^6$ is an N; $R^3$ is present when $X^7$ is a C and is absent when $X^7$ is an N; $R^4$ is present when $X^8$ is a C and is absent when $X^8$ is an N; and $R^5$ is present when $X^9$ is a C and is absent when $X^9$ is an N.

Each $R^7$ may be the same or different, provided that when $X^{10}$ is a ring nitrogen having a double bond $R^7$ is absent, when $X^{10}$ is a ring carbon having a double bond or is an N without a double bond only one $R^7$ group is present, and when $X^{10}$ is a ring carbon having no double bond two $R^7$ groups are present.

In all of the embodiments of this invention (both above and below herein), the substituents (each of the R groups) are not especially limited, provided that they do not prevent the TDO or IDO inhibitory function from occurring. In all of the embodiments mentioned in connection with this invention, both above and in the following, the substituents are selected from H and an organic group. Thus, both above and in the following, the terms 'substituent' and 'organic group' are not especially limited and may be any functional group or any atom, especially any functional group or atom common in organic chemistry. Thus, 'substituent' and 'organic group' may have any of the following meanings.

The organic group may comprise any one or more atoms from any of groups IIIA, IVA, VA, VIA or VIIA of the Periodic Table, such as a B, Si, N, P, O, or S atom (e.g. OH, OR, $NH_2$, NHR, $NR_2$, SH, SR, $SO_2R$, $SO_3H$, $PO_4H_2$) or a halogen atom (e.g. F, Cl, Br or I) where R is a linear or branched lower hydrocarbon (1-6 C atoms) or a linear or branched higher hydrocarbon (7 C atoms or more, e.g. 7-40 C atoms).

The organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, pyrrolidine, piperidine, morpholine, thiophene, benzothiophene, furan, benzofuran, pyrrole, indole, imidazole, thiazole, diazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The lower hydrocarbon group may be a methyl, ethyl, propyl, butyl, pentyl or hexyl group or regioisomers of these, such as isopropyl, isobutyl, tert-butyl, etc. The number of atoms in the ring of the cyclic group is not especially limited, but preferably the ring of the cyclic group comprises from 3-10 atoms, such as 3, 4, 5, 6, 7, 8, 9 or 10 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, sulphonyl groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

The invention will now be explained in more detail, by way of example only, with reference to the following Figures.

FIG. 1 shows a schematic diagram of tryptophan catabolism along the KP (from "The Kynurenine Pathway in Brain Tumour Pathogenesis", Adam et al., 2012, Cancer Res 72:5649-57).

Figure 2:
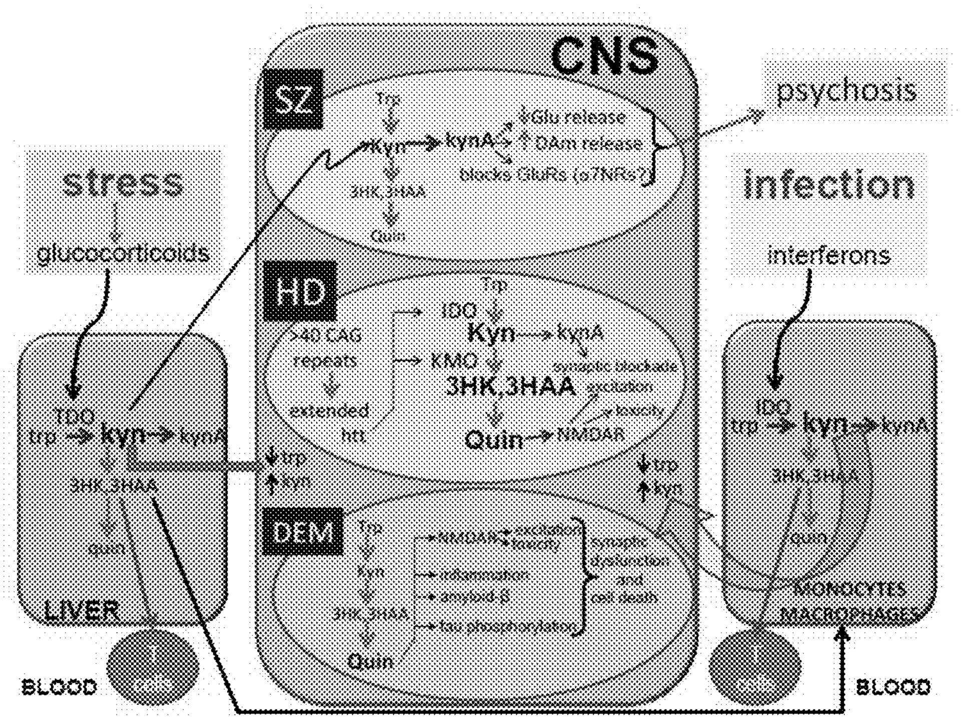

FIG. 2 shows a schematic summary of the involvement of kynurenine in CNS disorders (from "The kynurenine pathway as a therapeutic target in cognitive and neurodegenerative disorders", Stone and Darlington. Br. J. Pharmacol. 2013 169(6):1211-27.

The invention will now be described in more detail. Firstly a number of typical general structures of the compounds of the invention will be described.

As has been described, the invention relates to a tryptophan-2,3-dioxygenase (TDO) and/or indoleamine-2,3-dioxygenase (IDO) inhibitor compound for use in medicine, which compound comprises the following formula:

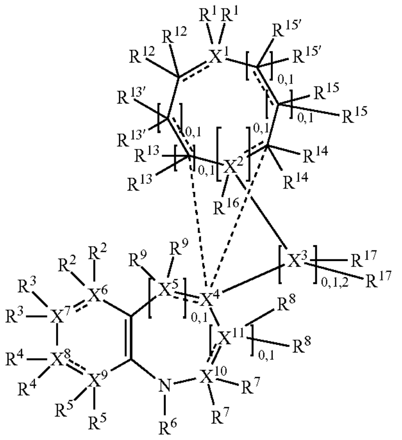

wherein $X^2$, $X^4$, $X^{10}$, and $X^{11}$ may be the same or different and each is independently selected from C and N; $X^1$, $X^3$, $X^5$, $X^6$, $X^7$, $X^8$, and $X^9$ may be the same or different and each is independently selected from C, N and O; each bond having a dotted line may independently be a double bond or a single bond, provided that valencies at each atom are maintained; the dotted lines joining $X^4$ with the carbon atoms either side of $X^2$ are single bonds, and are only present when $X^2$ is absent, $X^3$ is absent and $X^4$ is C, and when these bonds are present the ring carbons on each side of $X^2$ are not directly bonded to each other; each $R^1$ may be present or absent and may be the same or different and is selected from H and a substituted or unsubstituted organic group, provided that the number of $R^1$ groups present is such that the valency of $X^1$ is maintained; each $R^{12}$, $R^{13}$, $R^{13'}$, $R^{14}$, $R^{15}$ and $R^{15'}$ may be present or absent and may be the same or different and each is independently selected from H and a substituted or unsubstituted organic group, provided that the number of such R groups present is such that the valency of the ring carbon atoms is maintained; $R^{16}$ may be present or absent and is selected from H and a substituted or unsubstituted organic group, provided that the number of $R^{16}$ groups present is such that the valency of $X^2$ is maintained; each $R^{17}$ may be present or absent and may be the same or different and is independently selected from H and a substituted or unsubstituted organic group, provided that the number of $R^{17}$ groups present is such that the valency of $X^3$ is maintained; each $R^2$, $R^3$, $R^4$, and $R^5$ may be present or absent and may be the same or different and is selected from H and a substituted or unsubstituted organic group, provided that the number of such R groups present is such that the valencies of $X^6$, $X^7$, $X^8$, and $X^9$ are maintained; each $R^7$, $R^8$ and $R^9$ may be present or absent and may be the same or different and is selected from H and a substituted or unsubstituted organic group, provided that the number of such R groups present is such that the valencies of $X^{10}$, $X^{11}$, and $X^5$ are maintained; and $R^6$ is selected from H and a substituted or unsubstituted organic group, preferably H and a substituted or unsubstituted $C_1$-$C_6$ alkyl group; and wherein any R group may form a ring with any other R group on an adjacent and/or proximal atom.

The tryptophan-2,3-dioxygenase (TDO) and/or indoleamine-2,3-dioxygenase (IDO) inhibitor compound for use in medicine, may also comprise the following formula:

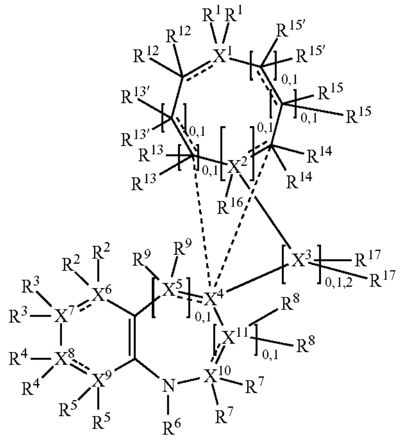

wherein the X and R groups are as defined anywhere herein.

All tautomeric forms of the ring system (including the tautomeric forms of the 6-membered ring and the tautomeric forms of the ring that may be 5-membered, 6-membered or 7-membered) are included.

As has been mentioned, this definition includes compounds in which, where there are two R groups attached to the same atom, they may together form a group which is double bonded to that atom, such as a carbonyl group (═O) or an alkene group (═C(R')$_2$) (wherein each R' group is the same or different and is H or an organic group, preferably H or a straight or branched $C_1$-$C_6$ alkyl group). Accordingly, in some embodiments $R^7$ may be a ═O group.

Thus, $X^1$ may be part of a 4-, 5-, 6-, 7-, or 8-membered ring, if desired, depending upon how many other atoms are present in the ring. $X^1$ may be in any position relative to $X^2$, as long as at least one carbon atom in the ring lies between $X^1$ and $X^2$. In more typical embodiments, $X^1$ is an N atom and is part of a six-membered ring in the 'para' position, or in the 4-position, relative to $X^2$.

It also follows that $X^4$, $X^5$, $X^{10}$ and $X^{11}$ form a ring together with an N and two C atoms, and at least $X^4$ and $X^{10}$ are present, such that the ring has 5 or more atoms. This ring has at least one unsaturated bond between the two adjacent C atoms bridging the ring system, but may also have 2 or 3 unsaturated bonds, depending upon the bonding between the X atoms. The ring may additionally have 6 or 7 atoms depending upon the presence or absence of $X^5$ and $X^{11}$. $X^4$, $X^{10}$ and $X^{11}$ are selected from C and N and $X^5$ is selected from C, N and O, and typically all of $X^4$, $X^5$, $X^{10}$ and $X^{11}$ are C, three of $X^4$, $X^5$, $X^{10}$ and $X^{11}$ are C, two of $X^4$, $X^5$, $X^{10}$ and $X^{11}$ are C, one of $X^4$, $X^5$, $X^{10}$ and $X^{11}$, is C or all of $X^4$, $X^5$, $X^{10}$ and $X^{11}$ are N. In typical embodiments when $X^5$ and $X^{11}$ are absent, $X^4$ and $X^{10}$ are C, $X^4$ is C and $X^{10}$ is N, $X^4$ is N and $X^{10}$ is C, or $X^4$ and $X^{10}$ are N. In all of these embodiments, it may also be the case that (when present) $X^5$ is O.

It further follows that $X^6$, $X^7$, $X^8$ and $X^9$ form a ring together with two C atoms, and all are present such that the ring is a 6-membered ring. This ring has at least one unsaturated bond between the two adjacent C atoms bridging the ring system, but may also have 2 or 3 unsaturated bonds, depending upon the bonding between the X atoms. $X^6$, $X^7$, $X^8$ and $X^9$ are selected from C, N and O. When one of these X atoms is O it is typical that none of the others is O. Typically all of $X^6$, $X^7$, $X^8$ and $X^9$ are C, three of $X^6$, $X^7$, $X^8$ and $X^9$ are C, two of $X^6$, $X^7$, $X^8$ and $X^9$ are C, one of $X^6$, $X^7$, $X^8$ and $X^9$, is C or all of $X^6$, $X^7$, $X^8$ and $X^9$ are N.

In typical embodiments, $X^2$ is present, and may be C or N, but in other typical embodiments $X^2$ is absent. In such embodiments, $X^3$ is also absent, and in those cases, $X^4$ is bonded to the carbon ring atoms that would have been either side of $X^2$, forming a 'spiro' compound having $X^4$ at the 'spiro' centre. In these cases $X^4$ is C. In other typical embodiments $X^3$ is absent such that $X^4$ is directly bonded to $X^2$.

In typical embodiments, $X^5$, and $X^{10}$ are absent, and/or $X^4$ and $X^{10}$ are part of a 5-membered ring.

In typical embodiments both above and below herein, $X^4$ is a C atom.

In typical embodiments both above and below herein, $X^{10}$ is a C atom.

Thus, in view of the typical embodiments already described, in more typical embodiments the invention relates to a compound as defined above, which compound comprises one or other of the following formulae:

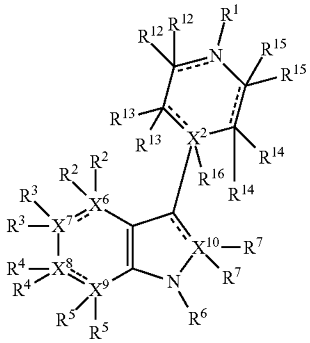

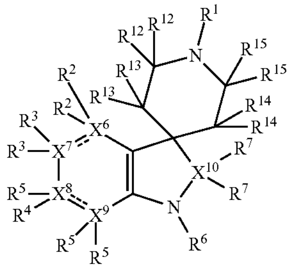

and in the case of the spiro compounds, preferably:

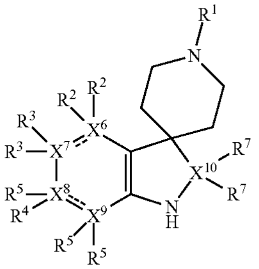

wherein, in each case, the substituents R and X are as defined in any of the above embodiments.

Furthermore, in view of the typical embodiments already described, in more typical embodiments the invention relates to a compound, which compound comprises the following formula:

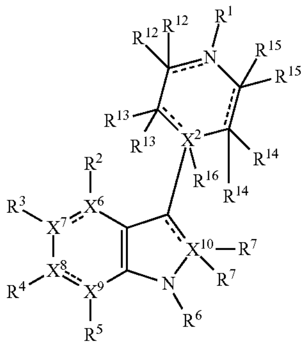

wherein $X^2$ $X^6$, $X^7$, $X^8$, $X^9$ and $X^{10}$ may be the same or different and each is independently selected from C and N; each bond having a dotted line may independently be a double bond or a single bond, provided that the valencies at each atom are maintained; $R^1$ may be present or absent and is selected from H and a substituted or unsubstituted organic group, provided that the number of $R^1$ groups present is such that the valency of the N atom attached to $R^1$ is maintained; each $R^{12}$, $R^{13}$, $R^{14}$, and $R^{15}$ may be present or absent and may be the same or different and each is independently selected from H and a substituted or unsubstituted organic group, provided that the number of such R groups present is such that the valency of the ring carbon atoms is maintained; $R^{16}$ may be present or absent and is selected from H and a substituted or unsubstituted organic group, provided that the number of $R^{16}$ groups present is such that the valency of $X^2$ is maintained; each $R^2$, $R^3$, $R^4$, and $R^5$ may be present or absent and may be the same or different and is selected from H and a substituted or unsubstituted organic group, provided that the number of such R groups present is such that the valencies of $X^6$, $X^7$, $X^8$, and $X^9$ are maintained; $R^6$ is selected from H and a substituted or unsubstituted organic group, preferably H and a substituted or unsubstituted $C_1$-$C_6$ alkyl group; and each $R^7$ may be present or absent and may be the same or different and each is independently selected from H and a substituted or unsubstituted organic group, provided that the number of $R^7$ groups present is such that the valency of $X^{10}$ is maintained; and wherein any R group may form a ring with any other R group on an adjacent and/or proximal atom. As already mentioned, where there are two R groups attached to the same atom, they may together form a group which is double bonded to that atom, such as a carbonyl group (=O) or an alkene group (=C(R')$_2$) (wherein each R' group is the same or different and is H or an organic group, preferably H or a straight or branched $C_1$-$C_6$ alkyl group). Accordingly, in some embodiments $R^7$ may be a =O group.

The X groups and R groups in all of the compounds and structures herein will now be described in more detail.

As has been mentioned, the number of R substituents on an X or a ring atom will depend on its valency. Thus, it will be apparent in all of the embodiments of the invention, both above and below, that when X or a ring atom has three ring bonds (either 3 single bonds or a single bond and a double bond), it will have no substituents if it is N and 1 substituent (H or an organic group as defined herein) if it is C, and when X or a ring atom has two ring bonds (2 single bonds), it will have 1 substituent (H or an organic group as defined herein) if it is N and 2 substituents if it is C (each independently chosen from H or an organic group as defined herein). Of course, if X is O there will not be any substituents.

As has been mentioned, in all of the embodiments of this invention (both above and below herein), the substituent is not especially limited, provided that it does not prevent the TDO or IDO inhibitory function from occurring. However, in typical embodiments, the substituents may be selected independently as follows.

$R^1$, $R^{12}$, $R^{13}$, $R^{13'}$, $R^{14}$, $R^{15}$, $R^{15'}$, $R^{16}$, $R^{17}$, $R^2$, $R^3$, $R^4$, $R^5$, $R^6$, $R^7$, $R^8$, and $R^9$ (and R') are typically each independently selected from H and a group selected from the following groups:

a halogen (such as F, Cl, Br and I);

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);

a substituted or unsubstituted linear or branched $C_1$-$C_6$ halogenated alkyl group (such as —$CH_2F$, —$CH_2Cl$, —$CH_2Br$, —$CH_2I$, —$CF_3$, —$CCl_3$—$CBr_3$, —$CI_3$, —$CH_2CF_3$, —$CH_2CCl_3$, —$CH_2CBr_3$, and —$CH_2CI_3$);

an —$NH_2$ group or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

an amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$I_2$-Ph, —NH-2,(3,4,5 or 6)$Me_2$-Ph, —NH-2,(3,4,5 or 6)$Et_2$-Ph, —NH-2,(3,4,5, or 6)$Pr_2$-Ph, —NH-2,(3,4,5 or 6)$Bu_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group or a substituted or unsubstituted linear or branched $C_1$-$C_6$ alcohol group (such as —$CH_2OH$, —$CH_2CH_2OH$, —$CH_2CH_2CH_2OH$, —$CH_2CH_2CH_2CH_2OH$, —$CH_2CH_2CH_2CH_2CH_2CH_2OH$, and —$CH_2CH_2CH_2CH_2CH_2CH_2OH$);

a substituted or unsubstituted linear or branched $C_1$-$C_6$ carboxylic acid group (such as —COOH, —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2$Ph, —(CO)$CH_2OH$, —(CO)$CH_2OCH_3$, —(CO)$CH_2NH_2$, —(CO)$CH_2$NHMe, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)$NHCH_2CH_2OH$, —(CO)$NHCH_2CH_2$OMe, —(CO)$NHCH_2CH_2NH_2$, —(CO)$NHCH_2CH_2$NHMe, and —(CO)$NHCH_2CH_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe);

a substituted or unsubstituted linear or branched $C_1$-$C_6$ amide group (such as —CO—$NH_2$, —CO—NMeH, —CO—$NMe_2$, —CO-NEtH, —CO-NEtMe, —CO-$NEt_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —$OCH_2Cl$, —$OCHCl_2$, —$OCCl_3$, —O-Ph, —O—$CH_2$-Ph, —O—$CH_2$-(2,3 or 4)-F-Ph, —O—$CH_2$-(2,3 or 4)-Cl-Ph, —$CH_2$OMe, —$CH_2$OEt, —$CH_2$OPr, —$CH_2$OBu, —$CH_2CH_2$OMe, —$CH_2CH_2CH_2CH_2$OMe, —$CH_2CH_2CH_2$C OMe, and —$CH_2CH_2CH_2CH_2CH_2$OMe);

a substituted or unsubstituted linear or branched amino-alkoxy group (such as —$OCH_2NH_2$, —$OCH_2$NHMe, —$OCH_2NMe_2$, —$OCH_2$NHEt, —$OCH_2NEt_2$, —$OCH_2CH_2NH_2$, —$OCH_2$C $H_2$NHMe, —$OCH_2CH_2NMe_2$, —$OCH_2CH_2$NHEt, and —$OCH_2CH_2NEt_2$;

a substituted or unsubstituted sulphonyl group (such as —$SO_2$Me, —$SO_2$Et, —$SO_2$Pr, —$SO_2$iPr, —$SO_2$Ph, —$SO_2$-(2,3 or 4)-F-Ph, —$SO_2$— cyclopropyl, —$SO_2CH_2CH_2OCH_3$), —$SO_2NH_2$, —$SO_2$NHMe, —$SO_2NMe_2$, —$SO_2$NHEt, —$SO_2NEt_2$, —$SO_2$-pyrrolidine-N-yl, —$SO_2$-morpholine-N-yl, —$SO_2NHCH_2$OMe, and —$SO_2NHCH_2CH_2$OMe;

a substituted or unsubstituted aminosulphonyl group (such as —$NHSO_2$Me, —$NHSO_2$Et, —$NHSO_2$Pr, —$NHSO_2$iPr, —$NHSO_2$Ph, —$NHSO_2$-(2,3 or 4)-F-Ph, —$NHSO_2$-cyclopropyl, —$NHSO_2CH_2CH_2OCH_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-$(NO_2)$-Ph-, 3-$(NO_2)$-Ph-, 4-$(NO_2)$-Ph-, 2-$(NH_2)$-Ph-, 3-$(NH_2)$-Ph-, 4-$(NH_2)$-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-);

a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl); or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl); and where there are two R groups attached to the same atom, they may together form a group which is double bonded to that atom, (such as a carbonyl group (═O) or an alkene group (═C(R')$_2$) (wherein each R' group is the same or different and is H or an organic group, preferably H or a straight or branched $C_1$-$C_6$ alkyl group)).

In some embodiments of the invention (both above and in the following), $R^1$ typically comprises a group having one of the following structures:

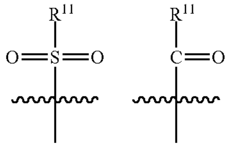

wherein $R^{11}$ is a group selected from H and:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);

a substituted or unsubstituted linear or branched $C_1$-$C_6$ halogenated alkyl group (such as —$CH_2F$, —$CH_2Cl$, —$CH_2Br$, —$CH_2I$, —$CF_3$, —$CCl_3$ —$CBr_3$, —$CI_3$, —$CH_2CF_3$, —$CH_2CCl_3$, —$CH_2CBr_3$, and —$CH_2CI_3$);

an —$NH_2$ group or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$F_2$-Ph, —NH-2,(3,4,5 or 6)$Me_2$-Ph, —NH-2,(3,4,5 or 6)$Et_2$-Ph, —NH-2,(3,4,5, or 6)$Pr_2$-Ph, —NH-2,(3,4,5 or 6)$Bu_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group or a substituted or unsubstituted linear or branched $C_1$-$C_6$ alcohol group (such as —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, and —$CH_2CH_2CH_2CH_2CH_2CH_2OH$);

a substituted or unsubstituted linear or branched $C_1$-$C_6$ carboxylic acid group (such as —COOH, —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2$Ph, —(CO)$CH_2OH$, —(CO)$CH_2OCH_3$, —(CO)$CH_2NH_2$, —(CO)$CH_2$NHMe, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)NH$CH_2CH_2OH$, —(CO)NH$CH_2CH_2$OMe, —(CO)NH$CH_2CH_2NH_2$, —(CO)NH$CH_2CH_2$NHMe, and —(CO)NH$CH_2CH_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe);

a substituted or unsubstituted linear or branched $C_1$-$C_6$ amide group (such as —CO—$NH_2$, —CO—NMeH, —CO—$NMe_2$, —CO-NEtH, —CO-NEtMe, —CO-$NEt_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO- Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —$OCH_2Cl$, —$OCHCl_2$, —$OCCl_3$, —O-Ph, —O—$CH_2$-Ph, —O—$CH_2$-(2,3 or 4)-F-Ph, —O—$CH_2$-(2,3 or 4)-Cl-Ph, —$CH_2OMe$, —$CH_2OEt$, —$CH_2OPr$, —$CH_2OBu$, —$CH_2CH_2OMe$, —$CH_2CH_2CH_2OMe$, —$CH_2CH_2CH_2CH_2OMe$, and —$CH_2CH_2CH_2CH_2CH_2OMe$);

a substituted or unsubstituted linear or branched amino-alkoxy group (such as —$OCH_2NH_2$, —$OCH_2NHMe$, —$OCH_2NMe_2$, —$OCH_2NHEt$, —$OCH_2NEt_2$, —$OCH_2CH_2NH_2$, —$OCH_2C$ $H_2NHMe$, —$OCH_2CH_2NMe_2$, —$OCH_2CH_2NHEt$, and —$OCH_2CH_2NEt_2$;

a substituted or unsubstituted sulphonyl group (such as —$SO_2Me$, —$SO_2Et$, —$SO_2Pr$, —$SO_2iPr$, —$SO_2Ph$, —$SO_2$-(2,3 or 4)-F-Ph, —$SO_2$— cyclopropyl, —$SO_2CH_2CH_2OCH_3$), —$SO_2NH_2$, —$SO_2NHMe$, —$SO_2NMe_2$, —$SO_2NHEt$, —$SO_2NEt_2$, —$SO_2$-pyrrolidine-N-yl, —$SO_2$-morpholine-N-yl, —$SO_2NHCH_2OMe$, and —$SO_2NHCH_2CH_2OMe$;

a substituted or unsubstituted aminosulphonyl group (such as —$NHSO_2Me$, —$NHSO_2Et$, —$NHSO_2Pr$, —$NHSO_2iPr$, —$NHSO_2Ph$, —$NHSO_2$-(2,3 or 4)-F-Ph, —$NHSO_2$-cyclopropyl, —$NHSO_2CH_2CH_2OCH_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or S)—$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-$(NO_2)$-Ph-, 3-$(NO_2)$-Ph-, 4-$(NO_2)$-Ph-, 2-(NH)-Ph-, 3-$(NH_2)$-Ph-, 4-$(NH_2)$-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3O$-Ph-, 3-$CF_3O$-Ph-, and 4-$CF_3O$-Ph-); and a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, -2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein, if present $R^{13'}$, $R^{15'}$, $R^{17}$, R, and $R^9$ are each H;

and/or preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present $R^{13}$, $R^{14}$, $R^{16}$, $R^2$, $R^5$, $R^6$, and $R^7$ are each H, and one or both of $R^{12}$ and/or one or both of $R^{15}$ and/or one or both of $R^{15'}$ are selected from a $C_1$-$C_3$ alkyl group optionally substituted with an —OH group or an —$NH_2$ group;

and/or preferably wherein, if present one of $R^3$ and $R^4$ is H while the other is selected from —H, —F, —Cl, -Me, —$CF_3$, -MeO and —CN.

In other embodiments of the invention (both above and in the following), $R^1$ typically comprises a group selected from H and the following:

a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-$(NO_2)$-Ph-, 3-$(NO_2)$-Ph-, 4-$(NO_2)$-Ph-, 2-$(NH_2)$-Ph-, 3-$(NH_2)$-Ph-, 4-$(NH_2)$-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3O$-Ph-, 3-$CF_3O$-Ph-, and 4-$CF_3O$-Ph-); and a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein, if present $R^{13'}$, $R^{5'}$, $R^{17}$, $R^8$, and $R^9$ are each H;

and/or preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^{13}$, $R^{14}$, $R^{16}$, $R^2$, $R^5$, $R^6$, and $R^7$ are each H, and one or both of $R^{12}$ and/or one or both of $R^{15}$ and/or one or both of $R^{15'}$ are selected from a $C_1$-$C_3$ alkyl group optionally substituted with an —OH group or an —$NH_2$ group;

and/or preferably wherein, if present one of $R^3$ and $R^4$ is H while the other is selected from —H, —F, —Cl, -Me, —$CF_3$, -MeO and —CN.

In this latter embodiment, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein, if present $R^{13'}$, $R^{15'}$, $R^{17}$, $R^8$, and $R^9$ are each H;

and/or preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^{13}$, $R^{14}$, $R^{16}$, $R^2$, $R^5$, $R^6$, and $R^7$ are each H, and one or both of $R^{12}$ and/or one or both of $R^{15}$ and/or one or both of $R^{15'}$ are selected from a $C_1$-$C_3$ alkyl group optionally substituted with an —OH group or an —$NH_2$ group;

and/or preferably wherein, if present one of $R^3$ and $R^4$ is H while the other is selected from —H, —F, —Cl, -Me, —$CF_3$, -MeO and —CN.

In typical embodiments of the invention, $R^6$ is selected from H and the following groups:

- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ halogenated alkyl group (such as —$CH_2F$, —$CF_3$, and —$CH_2CF_3$);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_2$-$C_6$ alcohol group (such as —$CH_2CH_2OH$, —$CH_2CH_2CH_2H$, —$CH_2CH_2CH_2CH_2OH$, —$CH_2CH_2CH_2CH_2CH_2OH$, and —$CH_2CH_2CH_2CH_2CH_2CH_2OH$); and
- a substituted or unsubstituted linear or branched $C_2$-$C_6$ carboxylic acid group (such as —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$).

In further typical embodiments, it is preferable that, where present, $R^{12}$, $R^{13}$, $R^{13'}$, $R^{14}$, $R^{15}$, $R^{15'}$, $R^{16}$, $R^{17}$, $R^2$, $R^5$, $R^6$, $R^7$, $R^8$ and $R^9$ are all H, (or alternatively wherein, if present $R^{13}$, $R^{13'}$, $R^{14}$, $R^{16}$, $R^{17}$, $R^2$, $R^5$, $R^6$, $R^7$, $R^8$ and $R^9$ are each H, and one or both of $R^{12}$ and/or one or both of $R^{15}$ and/or one or both of $R^{15'}$ are selected from a $C_1$-$C_3$ alkyl group optionally substituted with an —OH group or an —$NH_2$ group) and that, where present, either $R^3$ and $R^4$ are both H or one of $R^3$ and $R^4$ is not H. When $R^3$ is not H, $R^4$ is preferably H and $R^3$ is typically selected from —F, —Cl, -Me, —$CF_3$, —OMe, and —CN. When $R^4$ is not H, $R^3$ is preferably H and $R^4$ is typically selected from —F, —Cl, -Me, —$CF_3$, —OMe, and —CN. In these embodiments the X attached to $R^{16}$ is preferably a carbon atom such that it is part of a piperidinyl group. In typical embodiments that X atom is double bonded to another atom in the piperidinyl group, but the remaining ring atoms in the piperidinyl group are single bonded to each other. Alternatively all the ring atoms in the piperidinyl group are single bonded to each other. In these embodiments it is typical that $R^1$ is selected from a sulphonyl group and a carbonyl group, and a heterocyclic group. When $R^1$ is a sulphonyl group, it typically has a formula as set out below:

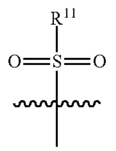

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups (such as 2-thiophenyl and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a carbonyl group, it typically has a formula as set out below:

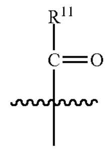

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a substituted or unsubstituted heterocyclic group, it is particularly typical that $R^1$ is a saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein, if present $R^{13'}$, $R^{15'}$, $R^{17}$, $R^8$, and $R^9$ are each H;

and/or preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^{13}$, $R^{14}$, $R^{16}$, $R^2$, $R^5$, $R^6$, and $R^7$ are each H, and one or both of $R^2$ and/or one or both of $R^{15}$ and/or one or both of $R^{15'}$ are selected from a $C_1$-$C_3$ alkyl group optionally substituted with an —OH group or an —$NH_2$ group;

and/or preferably wherein, if present one of $R^3$ and $R^4$ is H while the other is selected from —H, —F, —Cl, -Me, —$CF_3$, -MeO and —CN.

In some embodiments of the invention, it is advantageous that the five membered ring of the bicyclic system comprises a double bond. Thus, in certain embodiments, the compound comprises the following formula:

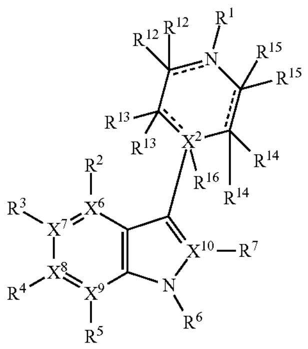

where the groups may be any of the specific or general groups as defined above or below herein. In this embodiment, it is typical that, where present, $R^{12}$, $R^{13}$, $R^{14}$, $R^{15}$, $R^{16}$, $R^2$, $R^5$, $R^6$, and $R^7$ are all H, (or alternatively wherein, if present $R^{13}$, $R^{14}$, $R^{16}$, $R^2$, $R^5$, $R^6$ and $R^7$ are each H, and one or both of $R^{12}$ and/or one or both of $R^{15}$ are selected from a $C_1$-$C_3$ alkyl group optionally substituted with an —OH group or an —$NH_2$ group) and that either $R^3$ and $R^4$ are both H or one of $R^3$ and $R^4$ is not H. When $R^3$ is not H, $R^4$ is preferably H and $R^3$ is typically selected from —F, —Cl, -Me, —$CF_3$, —OMe, and —CN. When $R^4$ is not H, $R^3$ is preferably H and $R^4$ is typically selected from —H, —F, —Cl, -Me, —$CF_3$, —OMe, and —CN. In these embodiments the X attached to $R^{16}$ is preferably a carbon atom such that it is part of a piperidinyl group. In typical embodiments that X atom is double bonded to another atom in the piperidinyl group, but the remaining ring atoms in the piperidinyl group are single bonded to each other. Alternatively all the ring atoms in the piperidinyl group are single bonded to each other. In these embodiments it is typical that $R^1$ is selected from a sulphonyl group and a carbonyl group and a heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

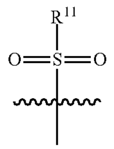

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2$OMe, —$CH_2$OEt, —$CH_2CH_2$OMe, —$CH_2CH_2$OEt, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2$Me, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a carbonyl group, it typically has a formula as set out below:

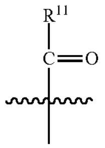

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2$OMe, —$CH_2$OEt, —$CH_2CH_2$OMe, —$CH_2CH_2$OEt, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2$Me, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a substituted or unsubstituted heterocyclic group, it is particularly typical that $R^1$ is a saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, if present one of $R^3$ and $R^4$ is H while the other is selected from —H, —F, —Cl, -Me, —$CF_3$, -MeO and —CN.

In further typical embodiments the compound is a compound having any one of the following formulae:

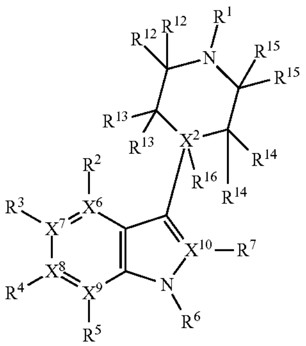

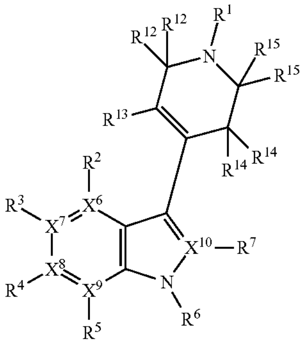

where the groups may be any of the specific or general groups as defined above or below herein. In this embodiment, it is typical that, where present, $R^{12}$, $R^{13}$, $R^{14}$, $R^{15}$, $R^{16}$, $R^2$, $R^5$, $R^6$, and $R^7$ are all H, (or alternatively wherein, if present $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group) and that either $R^3$ and $R^4$ are both H or one of $R^3$ and $R^4$ is not H. When $R^3$ is not H, $R^4$ is preferably H and $R^3$ is typically selected from —F, —Cl, -Me, —$CF_3$, —OMe, and —CN. When $R^4$ is not H, $R^3$ is preferably H and $R^4$ is typically selected from —F, —Cl, -Me, —$CF_3$, —OMe, and —CN. In these embodiments the X attached to $R^{16}$ is preferably a carbon atom such that it is part of a piperidinyl group. When X is N and is double bonded to another ring atom, the N group may carry a positive charge and may be associated with a negatively charged anionic group. In these embodiments it is typical that $R^1$ is selected from a sulphonyl group and a carbonyl group and a substituted or unsubstituted heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

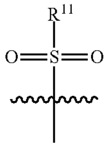

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a carbonyl group, it typically has a formula as set out below:

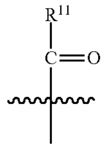

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)($CF_3$)$_2$, -Ph(2,3 or 2,4 or 2,5 or 2,6 or 3,4 or 3,5)$F_2$, -Ph(2,3 or 2,4 or 2,5 or 2,6 or 3,4 or 3,5)$C_2$, -Ph(2,3 or 2,4 or 2,5 or 2,6 or 3,4 or 3,5)(OMe)$_2$, -Ph(2,3 or 2,4 or 2,5 or 2,6 or 3,4 or 3,5) ($OCF_3$)$_2$, -Ph(2,3 or 2,4 or 2,5 or 2,6 or 3,4 or 3,5)(COOH)$_2$, -Ph(2,3 or 2,4 or 2,5 or 2,6 or 3,4 or 3,5)(COOMe)$_2$, -Ph(2,3 or 2,4 or 2,5 or 2,6 or 3,4 or 3,5)($SO_2Me$)$_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

and/or preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, if present one of $R^3$ and $R^4$ is H while the other is selected from —H, —F, —Cl, -Me, —$CF_3$, -MeO and —CN.

In further typical embodiments, the compound is a compound having any one of the following formulae:

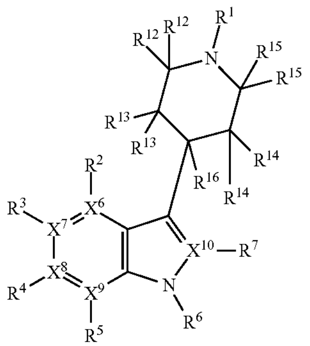

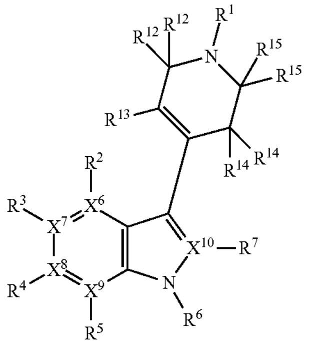

where the groups may be any of the specific or general groups as defined above or below herein. In this embodiment, it is typical that, where present, $R^{12}$, $R^{13}$, $R^{14}$, $R^{15}$, $R^{16}$, $R^2$, $R^5$, $R^6$, and $R^7$ are all H, (or alternatively wherein, if present $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group) and that either $R^3$ and $R^4$ are both H or one of $R^3$ and $R^4$ is not H. When $R^3$ is not H, $R^4$ is preferably H and $R^3$ is typically selected from —F, —Cl, -Me, —$CF_3$, —OMe, and —CN. When $R^4$ is not H, $R^3$ is preferably H and $R^4$ is typically selected from —F, —Cl, -Me, —$CF_3$, —OMe, and —CN. In these embodiments it is typical that $R^1$ is selected from a sulphonyl group and a carbonyl group and a substituted or unsubstituted heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

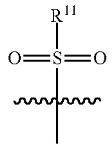

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)($CF_3$)$_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)(OMe)$_2$, -Ph(2,3 or 2,4 or 2,5 or 2,6 or 3,4 or 3,5) ($OCF_3$)$_2$, -Ph(2,3 or 2,4 or 2,5 or 2,6 or 3,4 or 3,5)(COOH)$_2$, -Ph(2,3 or 2,4 or 2,5 or 2,6 or 3,4 or 3,5)(COOMe)$_2$, -Ph(2,3 or 2,4 or 2,5 or 2,6 or 3,4 or 3,5)($SO_2Me$)$_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a carbonyl group, it typically has a formula as set out below:

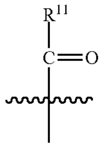

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-S-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

and/or preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, if present one of $R^3$ and $R^4$ is H while the other is selected from —H, —F, —Cl, -Me, —$CF_3$, -MeO and —CN.

In further typical embodiments, the compound is a compound having the following formula:

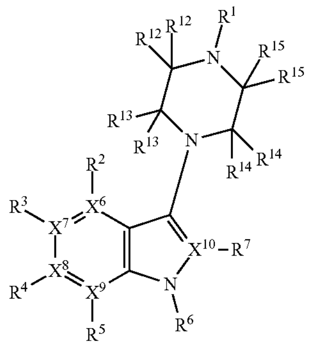

where the groups may be any of the specific or general groups as defined above or below herein. In this embodiment, it is typical that, where present, $R^{12}$, $R^{13}$, $R^{14}$, $R^{15}$, $R^2$, $R^5$, $R^6$, and $R^7$ are all H, (or alternatively wherein, if present $R^{13}$, $R^{14}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group) and that either $R^3$ and $R^4$ are both H or one of $R^3$ and $R^4$ is not H. When $R^3$ is not H, $R^4$ is preferably H and $R^3$ is typically selected from —F, —Cl, -Me, —$CF_3$, —OMe, and —CN. When $R^4$ is not H, $R^3$ is preferably H and $R^4$ is typically selected from —F, —Cl, -Me, —$CF_3$, —OMe, and —CN. In these embodiments it is typical that $R^1$ is selected from a substituted or unsubstituted sulphonyl group and a substituted or unsubstituted carbonyl group and a substituted or unsubstituted heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

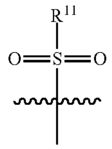

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a carbonyl group, it typically has a formula as set out below:

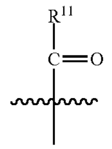

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein, if present, $R^{12}$, $R^{13}$, $R^{14}$, $R^{15}$, $R^2$, $R^5$, $R^6$, and $R^7$ are each H, or alternatively wherein, if present, $R^{13}$, $R^{14}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, if present one of $R^3$ and $R^4$ is H while the other is selected from —H, —F, —Cl, -Me, —$CF_3$, -MeO and —CN.

In further typical embodiments, the compound is a compound having any one of the following formulae:

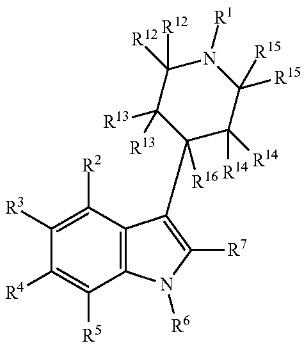

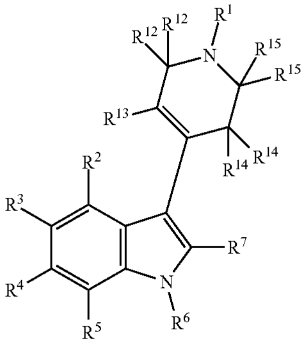

where the groups may be any of the specific or general groups as defined above or below herein. In this embodiment, it is typical that, where present, $R^{12}$, $R^{13}$, $R^{14}$, $R^{15}$, $R^{16}$, $R^2$, $R^5$, $R^6$, and $R^7$ are all H, (or alternatively wherein, if present $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group) and that either $R^3$ and $R^4$ are both H or one of $R^3$ and $R^4$ is not H. When $R^3$ is not H, $R^4$ is preferably H and $R^3$ is typically selected from —F, —Cl, -Me, —$CF_3$, —OMe, and —CN. When $R^4$ is not H, $R^3$ is preferably H and $R^4$ is typically selected from —F, —Cl, -Me, —$CF_3$, —OMe, and —CN. In these embodiments it is typical that $R^1$ is selected from a substituted or unsubstituted sulphonyl group and a substituted or unsubstituted carbonyl group and a substituted or unsubstituted heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

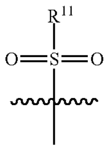

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a carbonyl group, it typically has a formula as set out below:

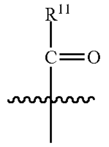

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, one of $R^3$ and $R^4$ is H while the other is selected from —H, —F, —Cl, -Me, —$CF_3$, -MeO and —CN.

In further typical embodiments, the compound is a compound having any one of the following formulae:

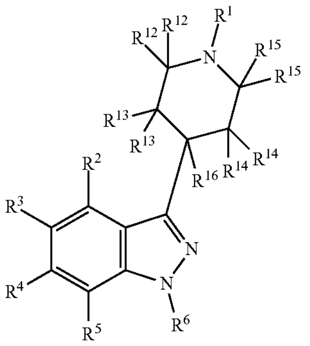

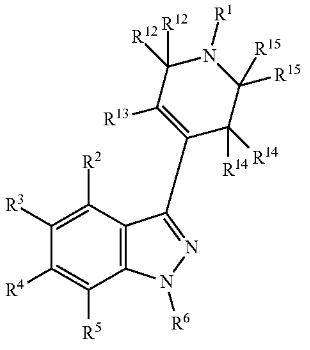

where the groups may be any of the specific or general groups as defined above or below herein. In this embodiment, it is typical that, where present, $R^{12}$, $R^{13}$, $R^{14}$, $R^{15}$, $R^{16}$, $R^2$, $R^5$, and $R^6$ are all H, (or alternatively wherein, if present $R^{13}$, $R^{14}$, $R^{16}$, $R^2$, $R^5$, and $R^6$ are each H, and one or both of $R^{12}$ and/or one or both of $R^{15}$ are selected from a $C_1$-$C_3$ alkyl group optionally substituted with an —OH group or an —$NH_2$ group) and that either $R^3$ and $R^4$ are both H or one of $R^3$ and $R^4$ is not H. When $R^3$ is not H, $R^4$ is preferably H and $R^3$ is typically selected from —F, —Cl, -Me, —$CF_3$, —OMe, and —CN. When $R^4$ is not H, $R^3$ is preferably H and $R^4$ is typically selected from —F, —Cl, -Me, —$CF_3$, —OMe, and —CN. In these embodiments it is typical that $R^1$ is selected from a substituted or unsubstituted sulphonyl group and a substituted or unsubstituted carbonyl group and a substituted or unsubstituted heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

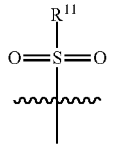

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a carbonyl group, it typically has a formula as set out below:

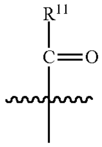

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5) $(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

and/or preferably wherein, if present, $R^{12}$, $R^{13}$, $R^{14}$, $R^{15}$, $R^{16}$, $R^2$, $R^5$, and $R^6$ are each H, or alternatively wherein, if present, $R^{13}$, $R^{14}$, $R^{16}$, $R^2$, $R^5$, and $R^6$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, one of $R^3$ and $R^4$ is H while the other is selected from —H, —F, —Cl, -Me, —$CF_3$, -MeO and —CN.

In further typical embodiments, the compound is a compound having any one of the following formulae:

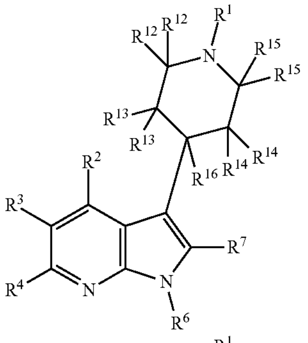

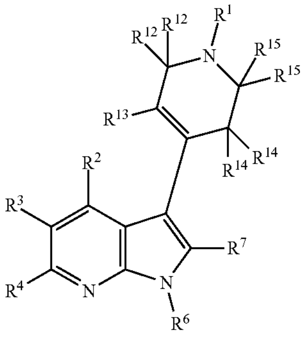

where the groups may be any of the specific or general groups as defined above or below herein. In this embodiment, it is typical that, where present, $R^{12}$, $R^{13}$, $R^{14}$, $R^{15}$, $R^{16}$, $R^2$, $R^6$, and $R^7$ are all H, (or alternatively wherein, if present $R^{13}$, $R^{14}$, $R^{16}$, $R^2$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group) and that either $R^3$ and $R^4$ are both H or one of $R^3$ and $R^4$ is not H. When $R^3$ is not H, $R^4$ is preferably H and $R^3$ is typically selected from —F, —Cl, —$CF_3$, -Me, —OMe, and —CN. When $R^4$ is not H, $R^3$ is preferably H and $R^4$ is typically selected from —F, —Cl, -Me, —$CF_3$, —OMe, and —CN. In these embodiments it is typical that $R^1$ is selected from a substituted or unsubstituted sulphonyl group and a substituted or unsubstituted carbonyl group and a substituted or unsubstituted heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

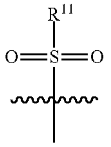

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5) $(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ is H and one of $R^3$ and $R^4$ is H while the other is selected from —H, —F, —Cl, -Me, —$CF_3$, -MeO and —CN. When $R^1$ is a carbonyl group, it typically has a formula as set out below:

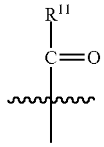

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2$Me, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ is H and one of $R^3$ and $R^4$ is H while the other is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

and/or preferably wherein, if present, $R^{12}$, $R^{13}$, $R^{14}$, $R^{15}$, $R^{16}$, $R^2$, $R^6$, and $R^7$ are each H, or alternatively wherein, if present, $R^{13}$, $R^{14}$, $R^{16}$, $R^2$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, one of $R^3$ and $R^4$ is H while the other is selected from —H, —F, —Cl, -Me, —$CF_3$, -MeO and —CN.

In further typical embodiments, the compound is a compound having any one of the following formulae:

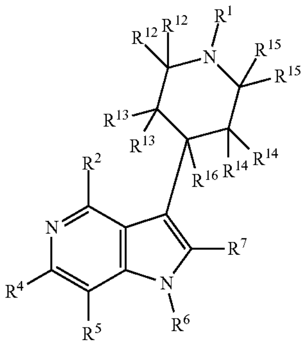

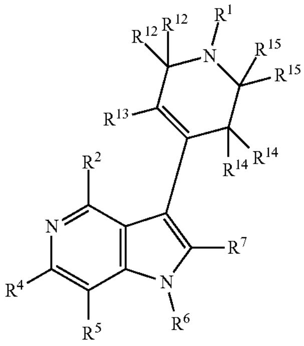

where the groups may be any of the specific or general groups as defined above or below herein. In this embodiment, it is typical that, where present, $R^{12}$, $R^{13}$, $R^{14}$, $R^{15}$, $R^{16}$, $R^2$, $R^5$, $R^6$, and $R^7$ are all H, (or alternatively wherein, if present $R^{13}$, $R^{14}$, $R^{15}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group) and that $R^4$ is H or is not H. When $R^4$ is not H, $R^4$ is typically selected from —F, —Cl, -Me, —$CF_3$, —OMe, and —CN. In these embodiments it is typical that $R^1$ is selected from a substituted or unsubstituted sulphonyl group and a substituted or unsubstituted carbonyl group and a substituted or unsubstituted heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

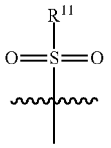

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2$OMe, —$CH_2$OEt, —$CH_2CH_2$OMe, —$CH_2CH_2$OEt, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2$Me, -Ph(2,3 or 2,4 or 2,5 or 2,6 or 3,4 or 3,5)$Me_2$, -Ph(2,3 or 2,4 or 2,5 or 2,6 or 3,4 or 3,5)$CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$C_2$, -Ph(2,3 or 2,4 or 2,5 or 2,6 or 3,4 or 3,5)$(OMe)_2$, -Ph(2,3 or 2,4 or 2,5 or 2,6 or 3,4 or 3,5)$(OCF_3)_2$, -Ph(2,3 or 2,4 or 2,5 or 2,6 or 3,4 or 3,5)$(COOH)_2$, -Ph(2,3 or 2,4 or 2,5 or 2,6 or 3,4 or 3,5)$(COOMe)_2$, -Ph(2,3 or 2,4 or 2,5 or 2,6 or 3,4 or 3,5)$(SO_2Me)_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and $R^4$ is selected from —H, —F, —Cl, -Me, —$CF_3$, -MeO and —CN. When $R^1$ is a carbonyl group, it typically has a formula as set out below:

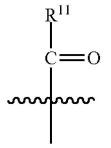

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2$OMe, —$CH_2$OEt, —$CH_2CH_2$OMe, —$CH_2CH_2$OEt, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2$Me, -Ph(2,3 or 2,4 or 2,5 or 2,6 or 3,4 or 3,5)$Me_2$, -Ph(2,3 or 2,4 or 2,5 or 2,6 or 3,4 or 3,5)$(CF_3)_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)(OMe)$_2$, -Ph(2,3 or 2,4 or 2,5 or 2,6 or 3,4 or 3,5)(OCF$_3$)$_2$, -Ph(2,3 or 2,4 or 2,5 or 2,6 or 3,4 or 3,5)(COOH)$_2$, -Ph(2,3 or 2,4 or 2,5 or 2,6 or 3,4 or 3,5)(COOMe)$_2$, -Ph(2,3 or 2,4 or 2,5 or 2,6 or 3,4 or 3,5)(SO$_2$Me)$_2$ and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and $R^4$ is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

and/or preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^3$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, $R^4$ is selected from —H, —F, —Cl, -Me, —$CF_3$, -MeO and —CN.

In further typical embodiments, the compound is a compound having any one of the following formulae:

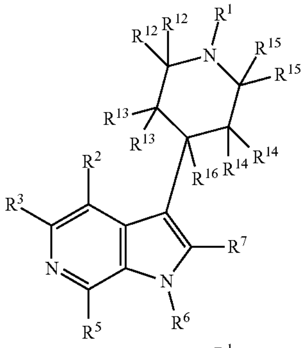

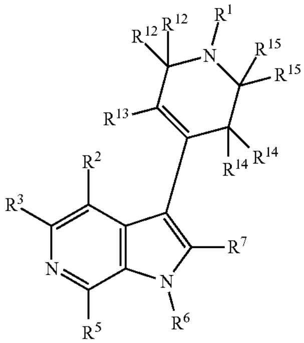

where the groups may be any of the specific or general groups as defined above or below herein. In this embodiment, it is typical that, where present, $R^{12}$, $R^{13}$, $R^{14}$, $R^{15}$, $R^{16}$, $R^2$, $R^5$, $R^6$, and $R^7$ are all H, (or alternatively wherein, if present $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group) and that $R^3$ is H or is not H. When $R^3$ is not H, $R^3$ is typically selected from —F, —Cl, -Me, —$CF_3$, —OMe, and —CN. In these embodiments it is typical that $R^1$ is selected from a substituted or unsubstituted sulphonyl group and a substituted or unsubstituted carbonyl group and a substituted or unsubstituted heterocyclic group (such as pyridyl groups, pyrimidyl groups, triazyl groups, oxazole groups, oxadiazole groups, diazole groups and thiophenyl groups). When $R^1$ is a sulphonyl group, it typically has a formula as set out below:

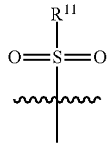

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2$OMe, —$CH_2$OEt, —$CH_2CH_2$OMe, —$CH_2CH_2$OEt, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2$Me, -Ph(2,3 or 2,4 or 2,5 or 2,6 or 3,4 or 3,5)$Me_2$, -Ph(2,3 or 2,4 or 2,5 or 2,6 or 3,4 or 3,5)($CF_3$)$_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)(OMe)$_2$, -Ph(2,3 or 2,4 or 2,5 or 2,6 or 3,4 or 3,5)(OCF$_3$)$_2$, -Ph(2,3 or 2,4 or 2,5 or 2,6 or 3,4 or 3,5)(COOH)$_2$, -Ph(2,3 or 2,4 or 2,5 or 2,6 or 3,4 or 3,5)(COOMe)$_2$, -Ph(2,3 or 2,4 or 2,5 or 2,6 or 3,4 or 3,5)(SO$_2$Me)$_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and $R^3$ is selected from —H, —F, —Cl, -Me, —$CF_3$, -MeO and —CN. When $R^1$ is a carbonyl group, it typically has a formula as set out below:

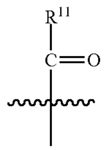

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2$OMe, —$CH_2$OEt, —$CH_2CH_2$OMe, —$CH_2CH_2$OEt, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2$Me, -Ph(2,3 or 2,4 or 2,5 or 2,6 or 3,4 or 3,5)$Me_2$, -Ph(2,3 or 2,4 or 2,5 or 2,6 or 3,4 or 3,5)($CF_3$)$_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)(OMe)$_2$, -Ph(2,3 or 2,4 or 2,5 or 2,6 or 3,4 or 3,5)(OCF$_3$)$_2$, -Ph(2,3 or 2,4 or 2,5 or 2,6 or 3,4 or 3,5)(COOH)$_2$, -Ph(2,3 or 2,4 or 2,5 or 2,6 or 3,4 or 3,5)(COOMe)$_2$, -Ph(2,3 or 2,4 or 2,5 or 2,6 or 3,4 or 3,5)($SO_2Me$)$_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^2$ and $R^5$ are H and $R^3$ is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

and/or preferably wherein, if present, $R^{12}$, $R^{13}$, $R^{14}$, $R^{15}$, $R^{16}$, $R^2$, $R^5$, $R^6$, and $R^7$ are each H, or alternatively wherein, if present, $R^{13}$, $R^{14}$, $R^{16}$, $R^2$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, $R^3$ is selected from —H, —F, —Cl, -Me, —$CF_3$, -MeO and —CN.

In further typical embodiments, the compound is a compound having any one of the following formulae:

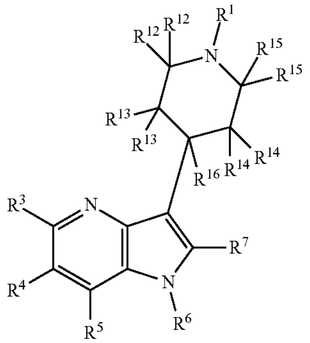

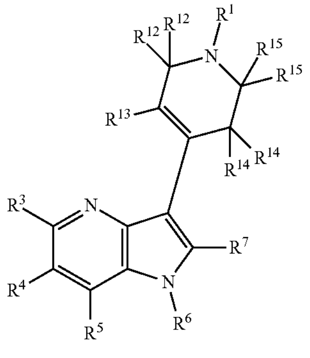

where the groups may be any of the specific or general groups as defined above or below herein. In this embodiment, it is typical that, where present, $R^{12}$, $R^{13}$, $R^{14}$, $R^{15}$1, $R^{16}$, $R^5$, $R^6$, and $R^7$ are all H, (or alternatively wherein, if present, $R^{13}$, $R^{14}$, $R^{16}$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group) and that either $R^3$ and $R^4$ are both H or one of $R^3$ and $R^4$ is not H. When $R^3$ is not H, $R^4$ is preferably H and $R^3$ is typically selected from —F, —Cl, -Me, —$CF_3$, —OMe, and —CN. When $R^4$ is not H, $R^3$ is preferably H and $R^4$ is typically selected from —F, —Cl, -Me, —$CF_3$, —OMe, and —CN. In these embodiments it is typical that $R^1$ is selected from a substituted or unsubstituted sulphonyl group and a substituted or unsubstituted carbonyl group and a substituted or unsubstituted heterocyclic group (such as pyridyl groups, pyrimidyl groups, triazyl groups, oxazole groups, oxadiazole groups, diazole groups and thiophenyl). When $R^1$ is a sulphonyl group, it typically has a formula as set out below:

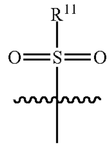

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_1$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)($CF_3$)$_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)(OMe)$_2$, -Ph(2,3 or 2,4 or 2,5 or 2,6 or 3,4 or 3,5)($OCF_3$)$_2$, -Ph(2,3 or 2,4 or 2,5 or 2,6 or 3,4 or 3,5)(COOH)$_2$, -Ph(2,3 or 2,4 or 2,5 or 2,6 or 3,4 or 3,5)(COOMe)$_2$, -Ph(2,3 or 2,4 or 2,5 or 2,6 or 3,4 or 3,5)($SO_2Me$)$_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^5$ is H and one of $R^3$ and $R^4$ is H while the other is selected from —H, —F, —Cl, -Me, —$CF_3$, -MeO and —CN. When $R^1$ is a carbonyl group, it typically has a formula as set out below:

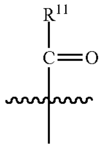

wherein $R^{11}$ is H or a substituted or unsubstituted organic group, and is typically a group selected from -Me, -Et, —Pr, -iPr, -cyclopropyl, -nBu, -iBu, -tBu, —$CF_3$, —$CCl_3$, —OMe, —OEt, —$CH_2OMe$, —$CH_2OEt$, —$CH_2CH_2OMe$, —$CH_2CH_2OEt$, —$NH_2$, —NHMe, —$NMe_2$, —NHEt, —$NEt_2$, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOH, -Ph(2, 3 or 4)COOMe, -Ph(2, 3 or 4)$SO_2Me$, -Ph(2,3 or 2,4 or 2,5 or 2,6 or 3,4 or 3,5)$Me_2$, -Ph(2,3 or 2,4 or 2,5 or 2,6 or 3,4 or 3,5)($CF_3$)$_2$, -Ph(2,3 or 2,4 or 2,5 or 2,6 or 3,4 or 3,5)$F_2$, -Ph(2,3 or 2,4 or 2,5 or 2,6 or 3,4 or 3,5)$Cl_2$, -Ph(2,3 or 2,4 or 2,5 or 2,6 or 3,4 or 3,5)(OMe)$_2$, -Ph(2,3 or 2,4 or 2,5 or 2,6 or 3,4 or 3,5)(OCF$_3$)$_2$, -Ph(2,3 or 2,4 or 2,5 or 2,6 or 3,4 or 3,5)(COOH)$_2$, -Ph(2,3 or 2,4 or 2,5 or 2,6 or 3,4 or 3,5)(COOMe)$_2$, -Ph(2,3 or 2,4 or 2,5 or 2,6 or 3,4 or 3,5)(SO$_2$Me)$_2$, and a substituted or unsubstituted heterocyclic group (such as pyridyl groups, pyrimidyl groups, triazyl groups, oxazole groups, oxadiazole groups, diazole groups and thiophenyl groups such as 2-thiophenyl, and 3-thiophenyl). In these embodiments, preferably $R^5$ is H and one of $R^3$ and $R^4$ is H while the other is selected from —H, —F, —Cl, -Me, —$CF_3$, -MeO and —CN. When $R^1$ is a heterocyclic group, it is particularly typical that $R^1$ is a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

and/or preferably wherein, if present, $R^{12}$, $R^{13}$, $R^{14}$, $R^{15}$, $R^{16}$, $R^5$, $R^6$, and $R^7$ are each H, or alternatively wherein, if present, $R^{13}$, $R^{14}$, $R^{16}$, $R^5$, $R^6$, and $R^7$ are each H, and one or both of $R^{12}$ and/or one or both of $R^{15}$ are selected from a $C_1$-$C_3$ alkyl group optionally substituted with an —OH group or an —$NH_2$ group;

and/or preferably wherein, one of $R^3$ and $R^4$ is H while the other is selected from —H, —F, —Cl, -Me, —$CF_3$, -MeO and —CN.

In particularly advantageous embodiments, the invention relates to a compound having any one of the following formulae:

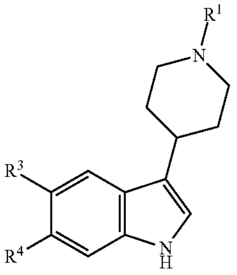
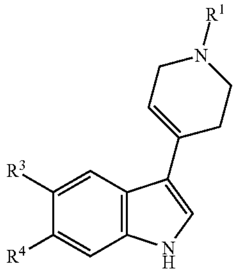

wherein $R^1$ is selected from the following substituents:

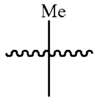
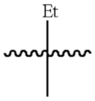
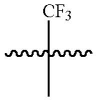
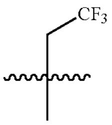
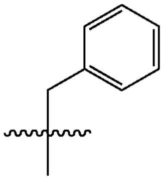
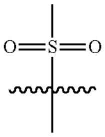
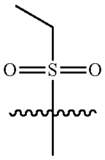
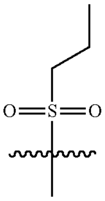

-continued

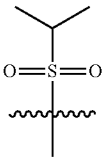
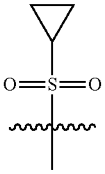
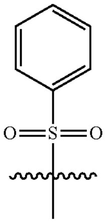
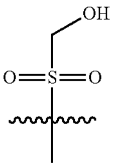
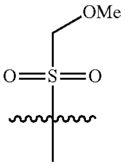
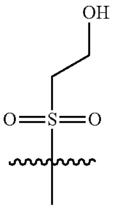
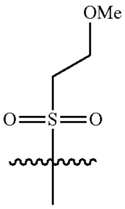
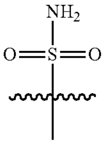
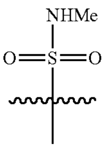
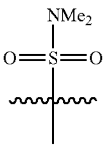
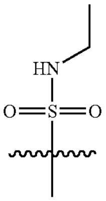
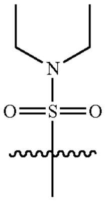
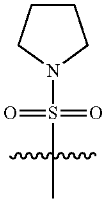
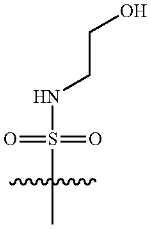
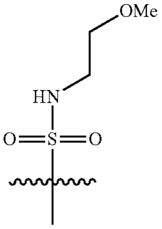
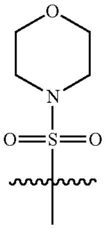
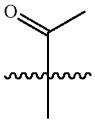
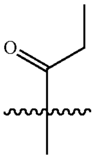
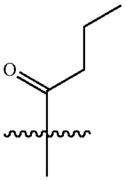
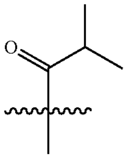
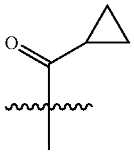
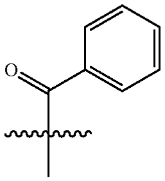
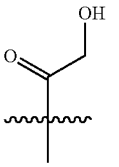
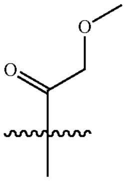
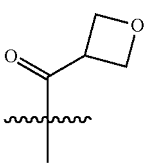
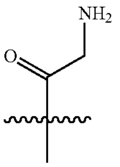
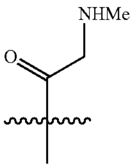
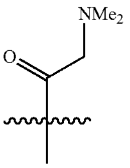
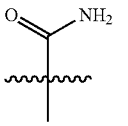

-continued
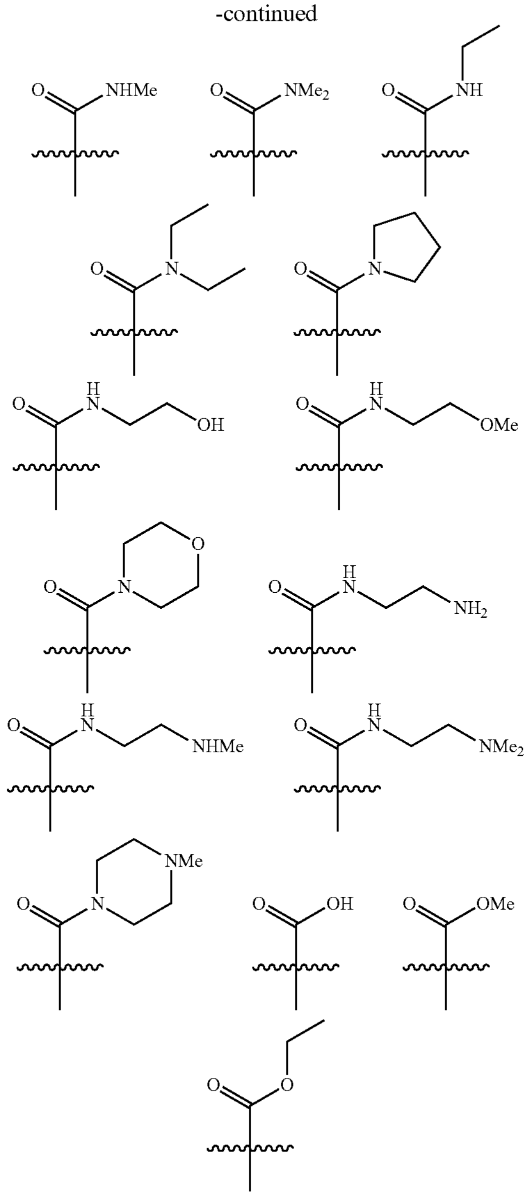
or when $R^1$ is a heterocyclic group, selected from the following groups:
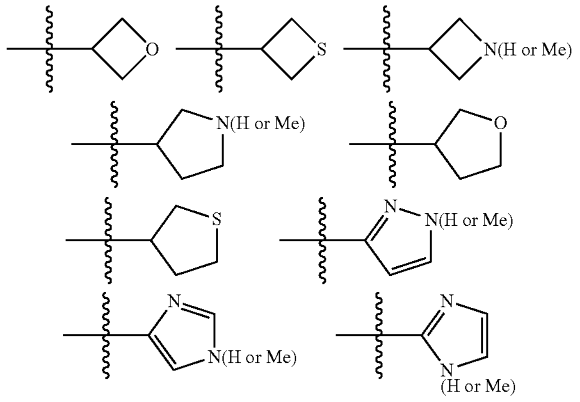
-continued
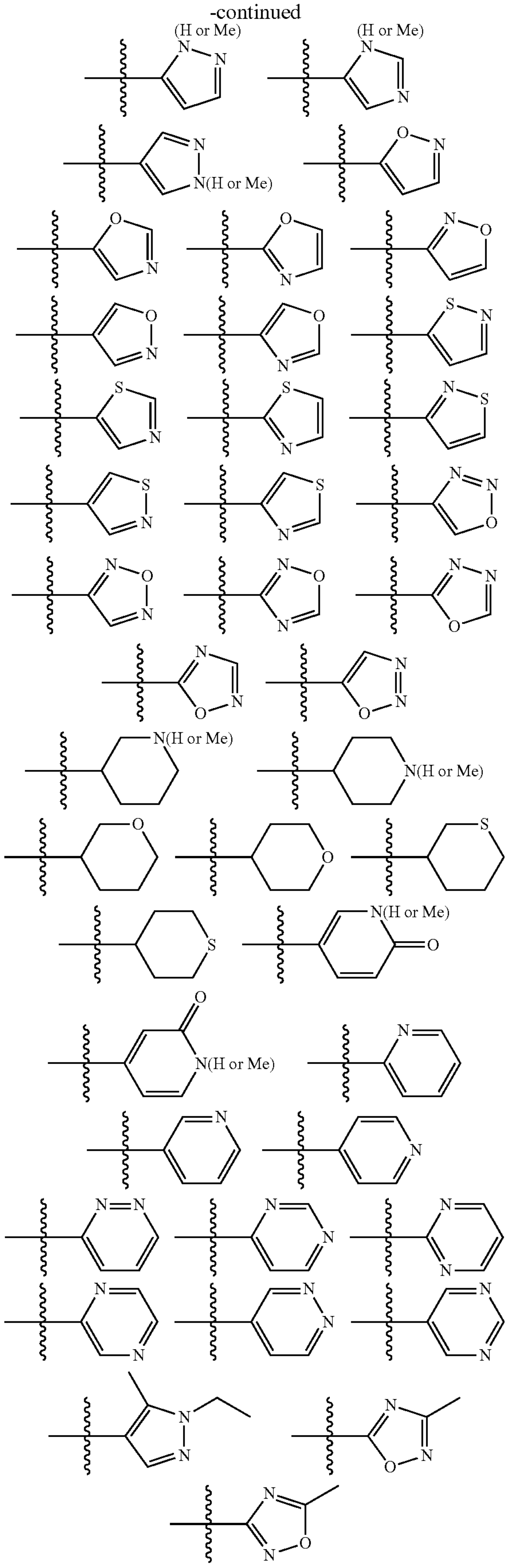

and wherein $R^3$ and $R^4$ are independently selected from the following: —H, —F, —Cl, -Me, —$CF_3$, —CN, —OMe, —OPh, —$OCH_2Ph$, —$OCH_2NH_2$, —$OCH_2NHMe$, —$OCH_2NMe$, —$OCH_2CH_2NH_2$, —$OCH_2CH_2NHMe$, —$OCH_2CH_2NMe$, preferably wherein one of $R^3$ and $R^4$ is H or alternatively preferably wherein one of $R^3$ and $R^4$ is —F and the other is —Cl.

As will be noted from the above, it is especially typical in the present invention that the compounds comprise an $R^1$ group that comprises a substituted or unsubstituted sulphonyl group or a substituted or unsubstituted carbonyl group or a substituted or unsubstituted heterocyclic group. Whilst typical such groups have been described above in various embodiments, further more preferred groups are those selected from a group having one of the following structures. Thus, when $R^1$ is a sulphonyl group, it typically has a formula as set out below:

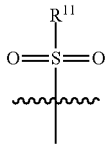

wherein $R^{11}$ a group selected from -Me, -Et, —Pr, -cyclopropyl, -nBu, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOMe, -Ph(2, 3 or 4)$SO_2Me$, substituted or unsubstituted 1,2-diazol-4-yl, substituted or unsubstituted 2-thiophenyl, and substituted or unsubstituted 3-thiophenyl. In these embodiments, preferably $R^2$ and $R^5$ are H and one of $R^3$ and $R^4$ is H while the other is selected from —H, —F, —Cl, -Me, —$CF_3$, -MeO and —CN. When $R^1$ is a carbonyl group, it typically has a formula as set out below:

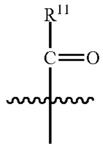

wherein $R^{11}$ a group selected from -Me, -Et, —Pr, -cyclopropyl, -nBu, -Ph, -Ph(2, 3 or 4)Me, -Ph(2, 3 or 4)$CF_3$, -Ph(2, 3 or 4)F, -Ph(2, 3 or 4)Cl, -Ph(2, 3 or 4)OMe, -Ph(2, 3 or 4)$OCF_3$, -Ph(2, 3 or 4)COOMe, -Ph(2, 3 or 4)$SO_2Me$, substituted or unsubstituted 1,2-diazol-4-yl, substituted or unsubstituted 2-thiophenyl, and substituted or unsubstituted 3-thiophenyl. In these embodiments, preferably $R^2$ and $R^5$ are H and one of $R^3$ and $R^4$ is H while the other is selected from —H, —F, —Cl, -Me, —$CF_3$, -MeO and —CN.

In the present invention, in the embodiments described both above and below, it is typical that $R^1$ is selected from H and:

- a carbonyl group selected from —(CO)Me, —(CO)Et, —(CO)Pr, —(CO)iPr, —(CO)nBu, —(CO)iBu, —(CO)tBu, —(CO)Ph, —(CO)$CH_2Ph$, —(CO)$CH_2OCH_3$, —(CO)$CH_2OH$, —(CO)$CH_2NH_2$, (CO)$CH_2NHMe$, —(CO)$CH_2NMe_2$, —(CO)cyclopropyl, and —(CO)isopropyl(1,3)oxy;
- a sulphonyl group selected from —$SO_2Me$, —$SO_2Et$, —$SO_2Pr$, —$SO_2iPr$, —$SO_2Ph$, —$SO_2$-(2,3 or 4)-F-Ph, —$SO_2$-cyclopropyl, and —$SO_2CH_2CH_2OCH_3$; and
- a group selected from —(CO)OEt, —(CO)NHEt, —$CH_2CF_3$, -Me, —$CH_2Ph$,
- a heterocyclic group selected from pyridin-2-yl, pyridin-3-yl, pyridin-4-yl, thiophen-2-yl, thiophen-3-yl, pyrimidin-2-yl, pyrimidin-4-yl, pyrimidin-5-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), in each case preferably wherein, where present, $R^{12}$, $R^{13}$, $R^{13'}$, $R^{14}$, $R^{15}$, $R^{15'}$, $R^{16}$, $R^{17}$, $R^2$, $R^5$, $R^6$, $R^7$, $R^8$ and $R^9$ are each H, (or alternatively wherein, if present $R^{13}$, $R^{13'}$, $R^{14}$, $R^{16}$, $R^{17}$, $R^2$, $R^5$, $R^6$, $R^7$, $R^8$ and $R^9$ are each H, and one or both of $R^{12}$ and/or one or both of $R^{15}$ and/or one or both of $R^{15'}$ are selected from a $C_1$-$C_3$ alkyl group optionally substituted with an —OH group or an —$NH_2$ group) and wherein one of $R^3$ and $R^4$ is H while the other is selected from —H, —F, —Cl, -Me, —$CF_3$, -MeO and —CN.

In the present invention, in the embodiments described both above and below, it is typical that, where present, $R^2$, $R^3$, $R^4$, $R^5$, $R^6$, $R^7$, $R^8$ and $R^9$ and are independently selected from H and:

—F and —Cl

-Me

—$CF_3$

—OMe

—CN

—$OCH_2Ph$;

—$OCH_2CH_2NMe_2$; and

=O (except $R^6$ is not =O)

in each case preferably wherein, where present, $R^2$, $R^5$, $R^6$, $R^7$, $R^8$ and $R^9$ are each H, and wherein one of $R^3$ and $R^4$ is H while the other is selected from —H, —F, —Cl, -Me, —$CF_3$, -MeO and —CN and in each case preferably wherein, where present, $R^{12}$, $R^{13}$, $R^{13'}$, $R^{14}$, $R^{15}$, $R^{15'}$, $R^{16}$ and $R^{17}$ are each H, or alternatively wherein, if present, $R^{13}$, $R^{13'}$, $R^{14}$, $R^{16}$, and $R^{17}$, are each H, and one or both of $R^{12}$ and/or one or both of $R^{15}$ and/or one or both of $R^{15'}$ are selected from a $C_1$-$C_3$ alkyl group optionally substituted with an —OH group or an —$NH_2$ group.

In the present invention, both the typical embodiments referred to above and below extend to compounds wherein $X^5$ and $X^{11}$ are present and where $R^8$ and $R^9$ are both H and where: all but one of $R^2$, $R^3$, $R^4$, $R^5$ and $R^7$ are H, or wherein all but two of $R^2$, $R^3$, $R^4$, $R^5$ and $R^7$ are H, or wherein all but three of $R^2$, $R^3$, $R^4$, $R^5$ and $R^7$ are H, or wherein all but four of $R^2$, $R^3$, $R^4$, $R^5$ and $R^7$ are H, or where all but five of $R^2$, $R^3$, $R^4$, $R^5$ and $R^7$ are H, or wherein all of $R^2$, $R^3$, $R^4$, $R^5$ and $R^7$ are not H. In such embodiments, typically, where present, all of $R^{12}$, $R^{13}$, $R^{13'}$, $R^{14}$, $R^5$, $R^{15'}$, $R^{16}$ and $R^{17}$ are H, (or alternatively wherein, if present, $R^{13}$, $R^{13'}$, $R^{14}$, $R^{16}$, and $R^{17}$, are each H, and one or both of $R^{12}$ and/or one or both of $R^{15}$ and/or one or both of $R^{15'}$ are selected from a $C_1$-$C_3$ alkyl group optionally substituted with an —OH group or an —$NH_2$ group), and/or typically one of $R^3$ and $R^4$ is H while the other is selected from —H, —F, —Cl, -Me, —$CF_3$, -MeO and —CN.

In the present invention, both the typical embodiments referred to above and below extend to compounds wherein $X^5$ and $X^{11}$ are absent and where: all but one of $R^2$, $R^3$, $R^4$, $R^5$ and $R^7$ are H, or wherein all but two of $R^2$, $R^3$, $R^4$, $R^5$ and $R^7$ are H, or wherein all but three of $R^2$, $R^3$, $R^4$, $R^5$ and $R^7$ are H, or wherein all but four of $R^2$, $R^3$, $R^4$, $R^5$ and $R^7$ are H, or where all but five of $R^2$, $R^3$, $R^4$, $R^5$ and $R^7$ are H, or wherein all of $R^2$, $R^3$, $R^4$, $R^5$ and $R^7$ are not H. In such embodiments, typically, where present, all of $R^{12}$, $R^{13}$, $R^{13'}$, $R^{14}$, $R^{15}$, $R^{16}$ and $R^{17}$ are H, (or alternatively wherein, if present, $R^{13}$, $R^{13'}$, $R^{14}$, $R^{16}$, and $R^{17}$, are each H, and one or both of $R^{12}$ and/or one or both of $R^{15}$ and/or one or both of $R^{15'}$ are selected from a $C_1$-$C_3$ alkyl group optionally substituted with an —OH group or an —$NH_2$ group), and/or typically one of $R^3$ and $R^4$ is H while the other is selected from —H, —F, —Cl, -Me, —$CF_3$, -MeO and —CN. In such embodiments, in some cases $R^7$ may be =O.

In all embodiments of the invention it is especially typical that $R^6$ is H. In such embodiments, typically one of $R^3$ and $R^4$ is H while the other is selected from —H, —F, —Cl, -Me, —$CF_3$, -MeO and —CN.

In some preferred embodiments, the invention therefore provides a tryptophan-2,3-dioxygenase (TDO) and/or indoleamine-2,3-dioxygenase (IDO) inhibitor compound for use in medicine, which compound comprises the following formula:

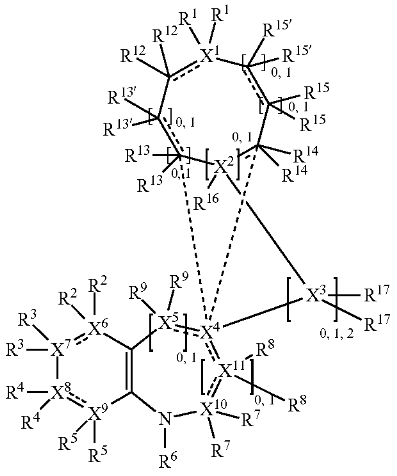

wherein $X^2$, $X^4$, $X^{10}$, and $X^{11}$ may be the same or different and each is independently selected from C and N; $X^1$, $X^3$, $X^5$, $X^6$, $X^7$, $X^8$, and $X^9$ may be the same or different and each is independently selected from C, N and O; each bond having a dotted line may independently be a double bond or a single bond, provided that valencies at each atom are maintained; the dotted lines joining $X^4$ with the carbon atoms either side of $X^2$ are single bonds, and are only present when $X^2$ is absent, $X^3$ is absent and $X^4$ is C, and when these bonds are present the ring carbons on each side of $X^2$ are not directly bonded to each other; each $R^1$ may be present or absent and may be the same or different and is selected from H and a substituted or unsubstituted organic group, provided that the number of $R^1$ groups present is such that the valency of $X^1$ is maintained; each $R^{12}$, $R^{13}$, $R^{13'}$, $R^{14}$, $R^{15}$ and $R^{15'}$ may be present or absent and may be the same or different and each is independently selected from H and a substituted or unsubstituted organic group, provided that the number of such R groups present is such that the valency of the ring carbon atoms is maintained; $R^{16}$ may be present or absent and is selected from H and a substituted or unsubstituted organic group, provided that the number of $R^{16}$ groups present is such that the valency of $X^2$ is maintained; each $R^{17}$ may be present or absent and may be the same or different and is independently selected from H and a substituted or unsubstituted organic group, provided that the number of $R^{17}$ groups present is such that the valency of $X^3$ is maintained; each $R^2$, $R^3$, $R^4$, and $R^5$ may be present or absent and may be the same or different and is selected from H and a substituted or unsubstituted organic group, provided that the number of such R groups present is such that the valencies of $X^6$, $X^7$, $X^8$, and $X^9$ are maintained; each $R^7$, $R^8$ and $R^9$ may be present or absent and may be the same or different and is selected from H and a substituted or unsubstituted organic group, provided that the number of such R groups present is such that the valencies of $X^{10}$, $X^{11}$, and $X^5$ are maintained; and $R^6$ is selected from H and a substituted or unsubstituted organic group, preferably H and a substituted or unsubstituted $C_1$-$C_6$ alkyl group;

and wherein no R group may form a ring with any other R group on an adjacent or a proximal atom, and wherein, where present, $R^1$, $R^{12}$, $R^{13}$, $R^{13'}$, $R^{14}$, $R^{15}$, $R^{15'}$, $R^{16}$, $R^{17}$, $R^2$, $R^3$, $R^4$, $R^5$, $R^6$, $R^7$, $R^8$, and $R^9$ are each independently selected from H and a group selected from the following groups:

a halogen (such as F, Cl, Br and I);

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);

a substituted or unsubstituted linear or branched $C_1$-$C_6$ halogenated alkyl group (such as —$CH_2F$, —$CH_2Cl$, —$CH_2Br$, —$CH_2I$, —$CF_3$, —$CCl_3$—$CBr_3$, —$CI_3$, —$CH_2CF_3$, —$CH_2CCl_3$, —$CH_2CBr_3$, and —$CH_2CI_3$);

an —$NH_2$ group or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$I_2$-Ph, —NH-2,(3,4,5 or 6)$Me_2$-Ph, —NH-2,(3,4,5 or 6)$Et_2$-Ph, —NH-2,(3,4,5, or 6)$Pr_2$-Ph, —NH-2,(3,4,5 or 6)$Bu_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group or a substituted or unsubstituted linear or branched $C_1$-$C_6$ alcohol group (such as —$CH_2OH$, —$CH_2CH_2OH$, —$CH_2CH_2CH_2OH$, —$CH_2CH_2H_2CH_2OH$, —$CH_2CH_2CH_2CH_2CH_2OH$, and —$CH_2CH_2CH_2CH_2CH_2CH_2OH$);

a substituted or unsubstituted linear or branched $C_1$-$C_6$ carboxylic acid group (such as —COOH, —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2$Ph, —(CO)$CH_2OH$, —(CO)$CH_2OCH_3$, —(CO)$CH_2NH_2$, —(CO)$CH_2$NHMe, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)$NHCH_2CH_2OH$, —(CO)$NHCH_2CH_2$OMe, —(CO)$NHCH_2CH_2NH_2$, —(CO)$NHCH_2CH_2$NHMe, and —(CO)$NHCH_2CH_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe);

a substituted or unsubstituted linear or branched $C_1$-$C_6$ amide group (such as —CO—$NH_2$, —CO—NMeH, —CO—$NMe_2$, —CO-NEtH, —CO-NEtMe, —CO-$NEt_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —$OCH_2Cl$, —$OCHCl_2$, —$OCCl_3$, —O-Ph, —O—$CH_2$-Ph, —O—$CH_2$-(2,3 or 4)-F-Ph, —O—$CH_2$-(2,3 or 4)-Cl-Ph, —$CH_2$OMe, —$CH_2$OEt, —$CH_2$OPr, —$CH_2$OBu, —$CH_2CH_2$OMe, —$CH_2CH_2CH_2$OMe, —$CH_2CH_2CH_2CH_2CH_2$OMe, and —$CH_2CH_2CH_2CH_2CH_2$OMe);

a substituted or unsubstituted linear or branched amino-alkoxy group (such as —$OCH_2NH_2$, —$OCH_2$NHMe, —$OCH_2NMe_2$, —$OCH_2$NHEt, —$OCH_2NEt_2$, —$OCH_2CH_2NH_2$, —$OCH_2C$ $H_2$NHMe, —$OCH_2CH_2NMe_2$, —$OCH_2CH_2$NHEt, and —$OCH_2CH_2NEt_2$;

a substituted or unsubstituted sulphonyl group (such as —$SO_2$Me, —$SO_2$Et, —$SO_2$Pr, —$SO_2$iPr, —$SO_2$Ph, —$SO_2$-(2,3 or 4)-F-Ph, —$SO_2$— cyclopropyl, —$SO_2CH_2CH_2OCH_3$), —$SO_2NH_2$, —$SO_2$NHMe, —$SO_2NMe_2$, —$SO_2$NHEt, —$SO_2NEt_2$, —$SO_2$-pyrrolidine-N-yl, —$SO_2$-morpholine-N-yl, —$SO_2NHCH_2$OMe, and —$SO_2NHCH_2CH_2$OMe;

a substituted or unsubstituted aminosulphonyl group (such as —$NHSO_2$Me, —$NHSO_2$Et, —$NHSO_2$Pr, —$NHSO_2$iPr, —$NHSO_2$Ph, —$NHSO_2$-(2,3 or 4)-F-Ph, —$NHSO_2$-cyclopropyl, —$NHSO_2CH_2CH_2OCH_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-$(NO_2)$-Ph-, 3-$(NO_2)$-Ph-, 4-$(NO_2)$-Ph-, 2-$(NH_2)$-Ph-, 3-$(NH_2)$-Ph-, 4-$(NH_2)$-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-);

a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-4-yl, (1,3,4-oxadiazol)-5-yl, (1,3-thiazol)-2-yl, (1,3-thiazol)-4-yl, (1,3-thiazol)-5-yl, furan-2-yl, and furan-3-yl); or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl); and where there are two R groups attached to the same atom, they may together form a group which is double bonded to that atom, (such as a carbonyl group (=O) or an alkene group (=$C(R')_2$) wherein each R' group is the same or different and is H or an organic group, preferably H or a straight or branched $C_1$-$C_5$ alkyl group);

preferably wherein $R^6$ is selected from H and the following groups:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ halogenated alkyl group (such as —$CH_2F$, —$CF_3$, and —$CH_2CF_3$);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted linear or branched $C_2$-$C_6$ alcohol group (such as —$CH_2CH_2OH$, —$CH_2CH_2CH_2OH$, —$CH_2CH_2CH_2CH_2OH$, —$CH_2CH_2CH_2CH_2CH_2OH$, and —$CH_2CH_2CH_2CH_2CH_2CH_2OH$); and a substituted or unsubstituted linear or branched $C_2$-$C_5$ carboxylic acid group (such as —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$).

Thus, the present invention provides a TDO or IDO inhibitor compound for use in medicine, which compound comprises a formula selected from one of the following:

1
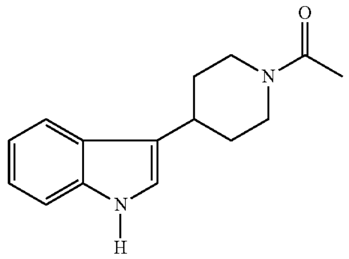
2
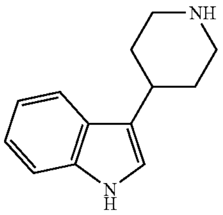
3
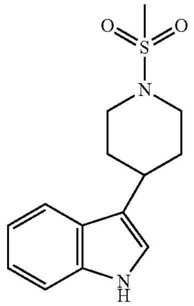
4
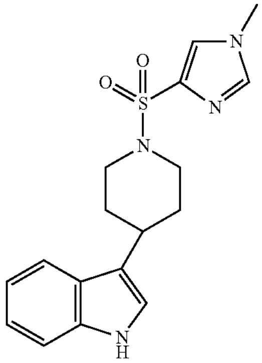
5
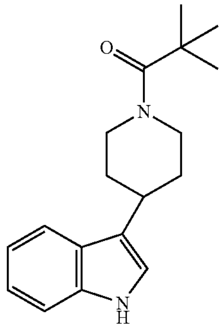
-continued
6
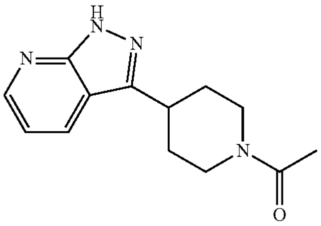
7
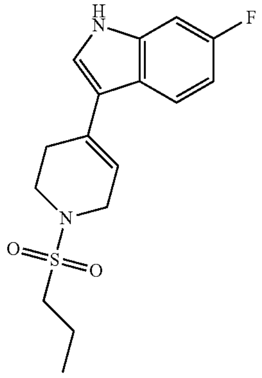
8
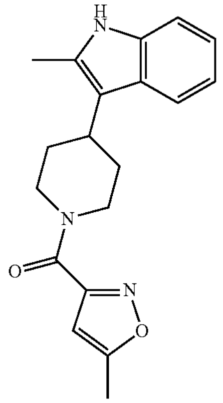
9
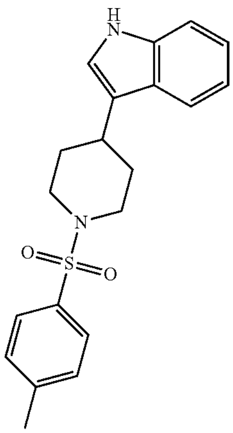

-continued
10
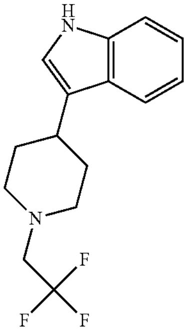
11
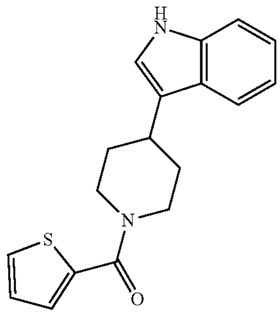
12
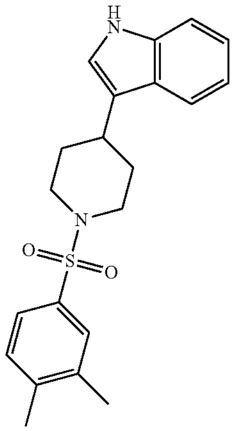
13
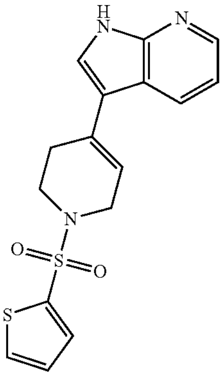
-continued
14
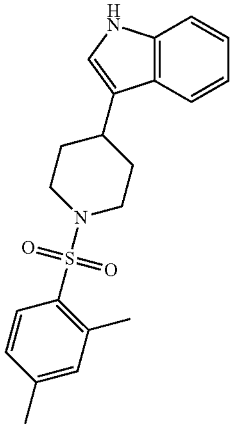
15
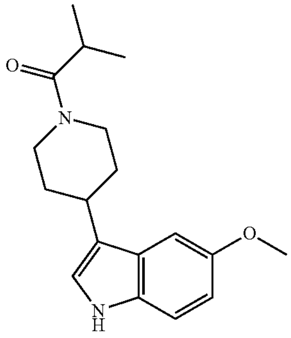
16
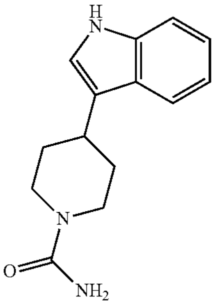
17
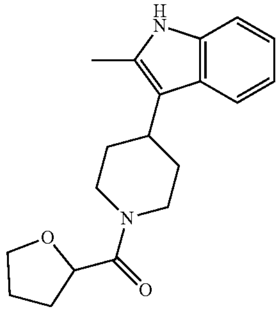

-continued
18
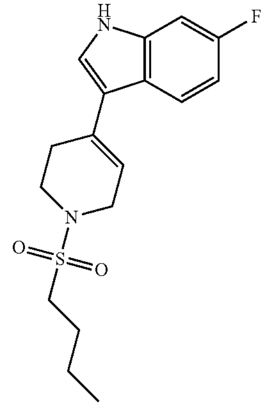
19
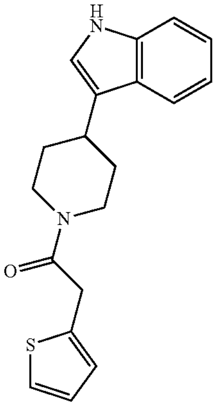
20
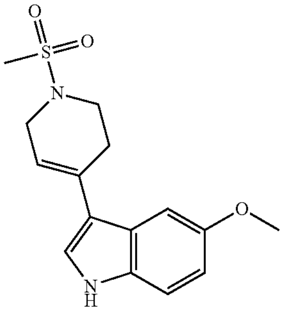
21
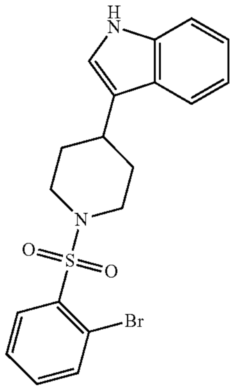
-continued
22
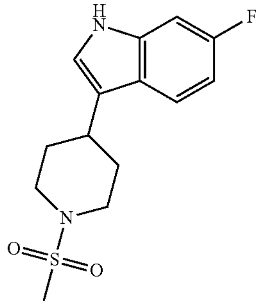
23
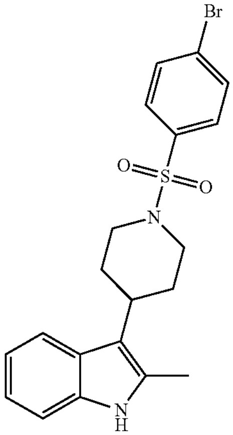
24
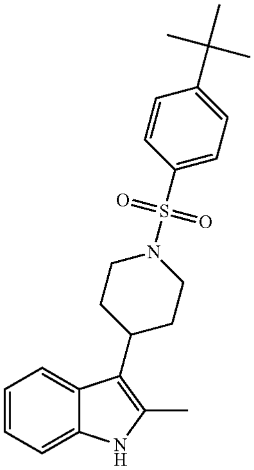
25
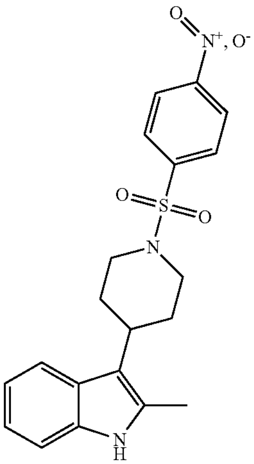

-continued
26
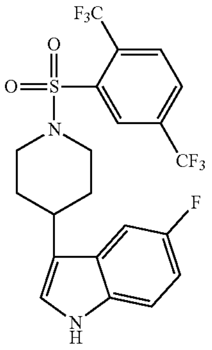
27
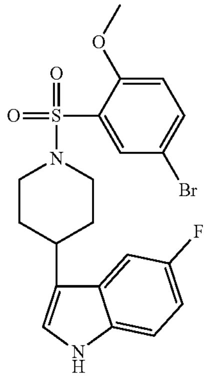
28
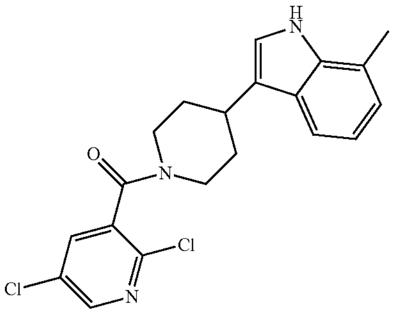
29
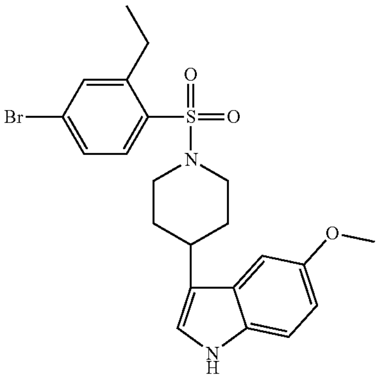
-continued
30
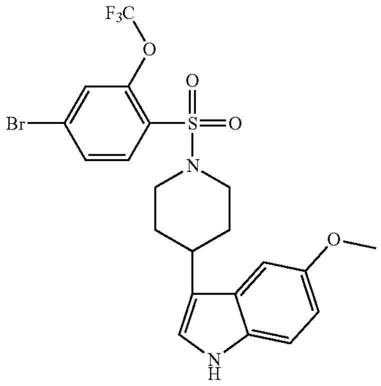
31
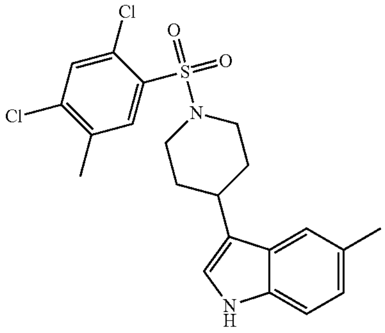
32
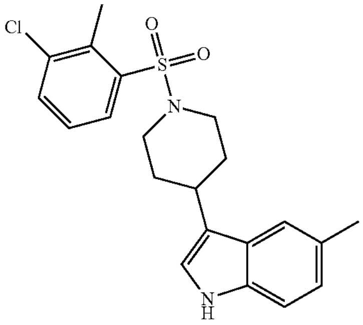
33
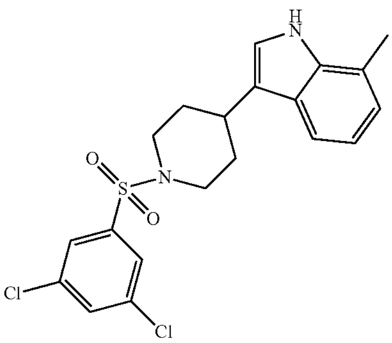

-continued
34
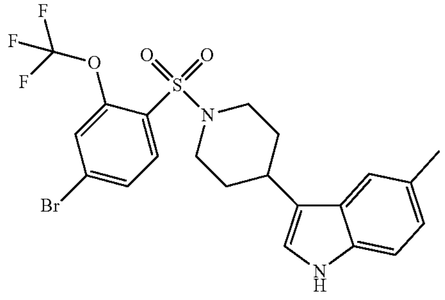
35
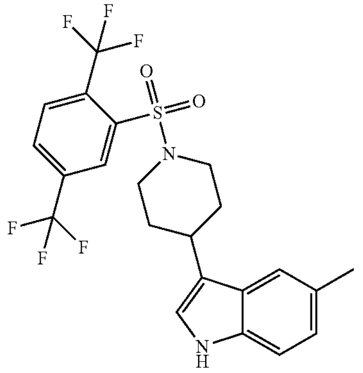
36
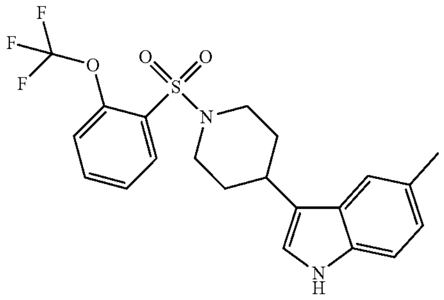
37
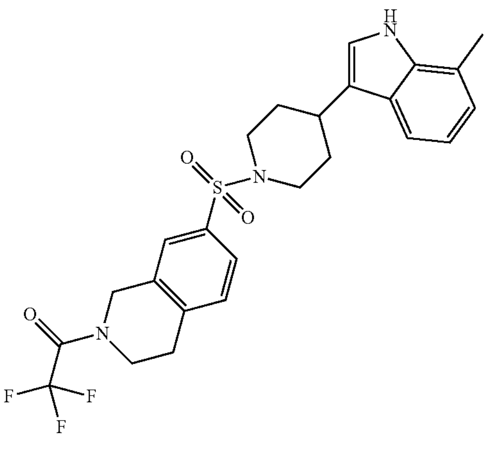
-continued
38
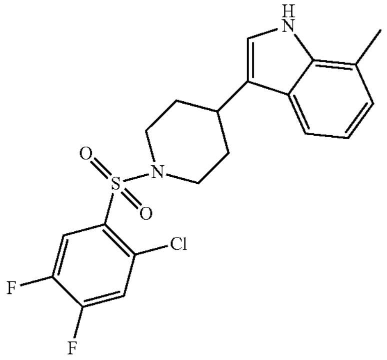
39
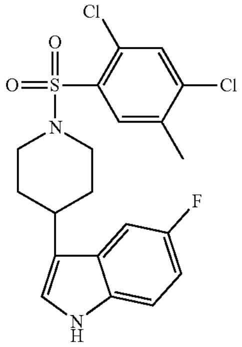
40
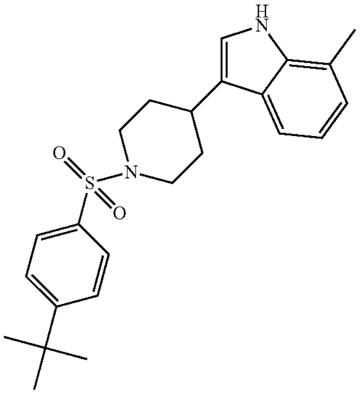
41
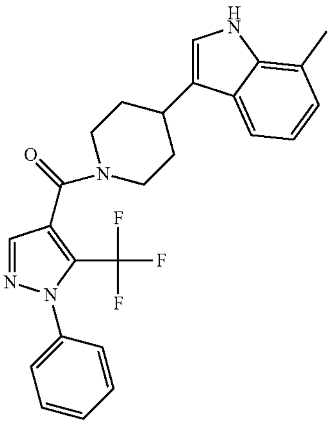

-continued
42
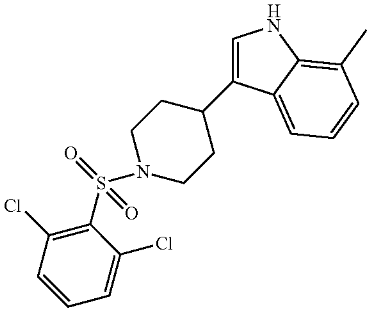
43
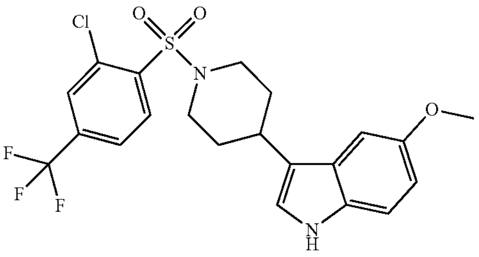
44
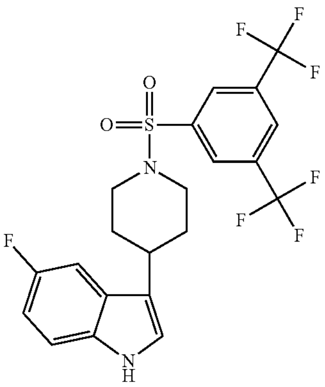
45
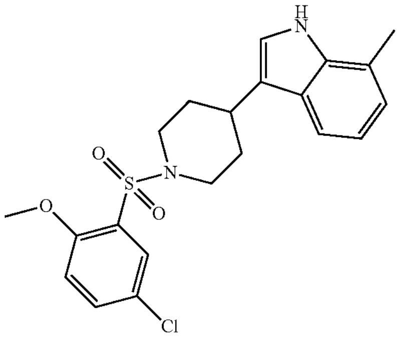
46
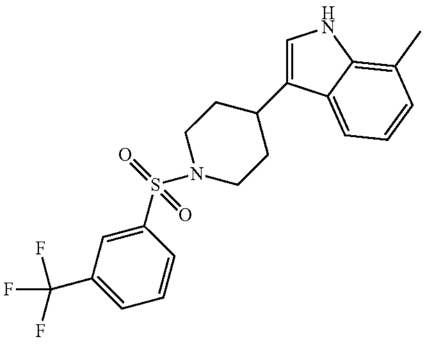
-continued
47
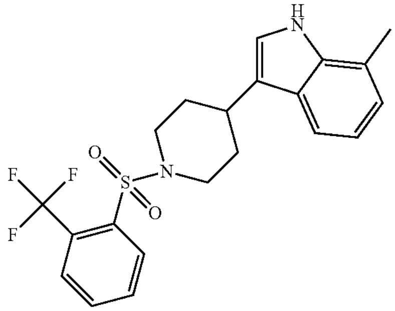
48
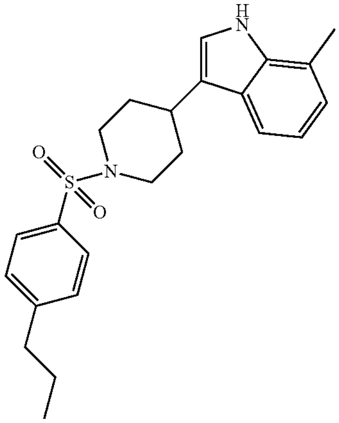
49
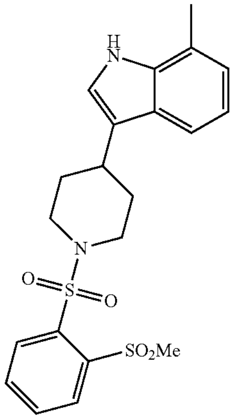
50
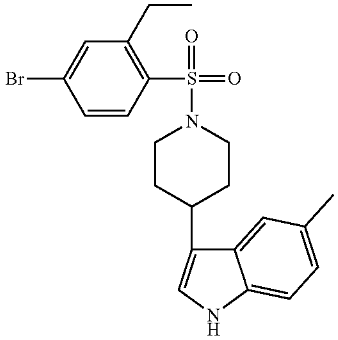

-continued
51
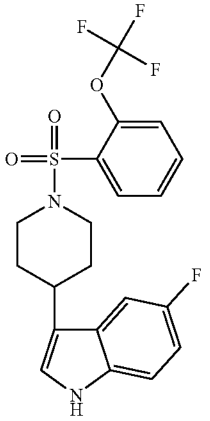
52
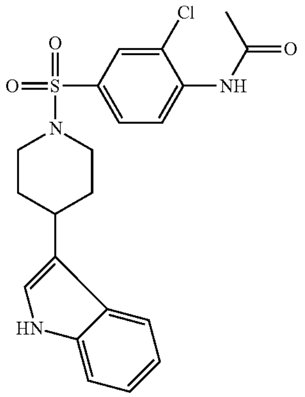
53
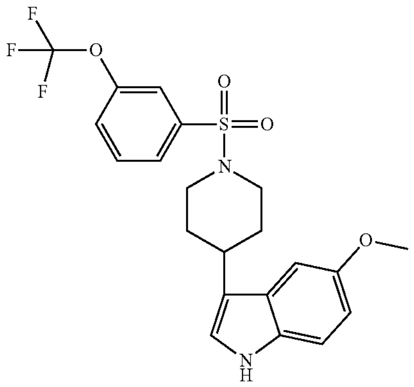
54
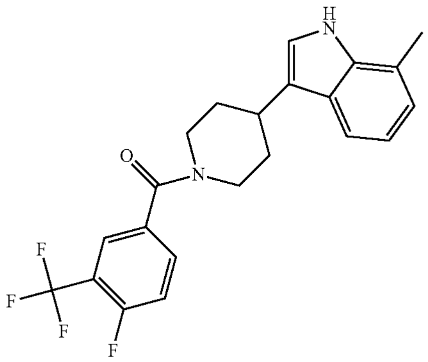
-continued
55
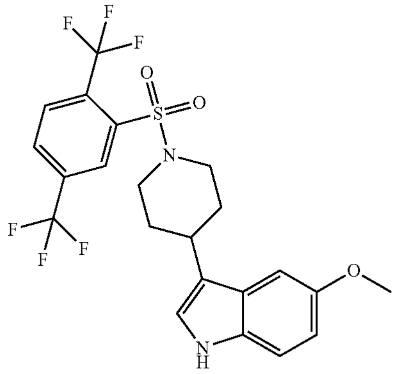
56
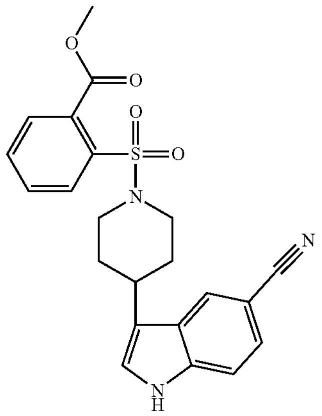
57
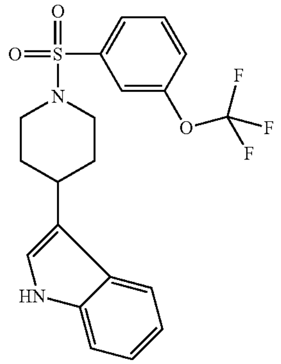
58
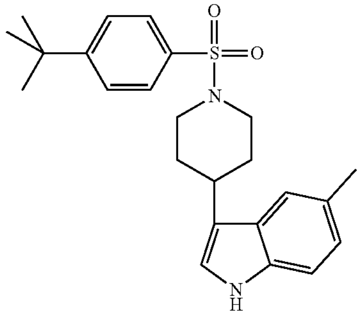

-continued
59
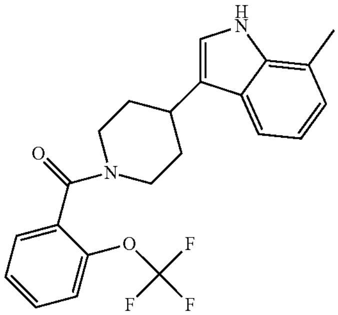
60
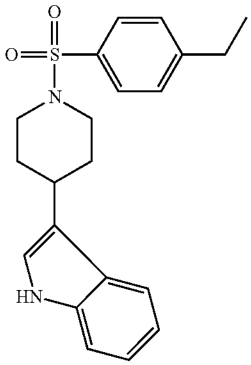
61
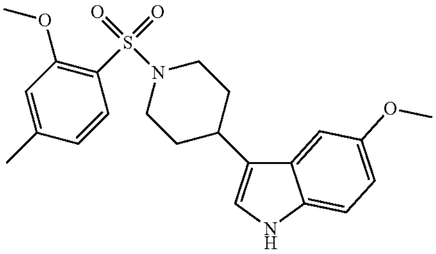
62
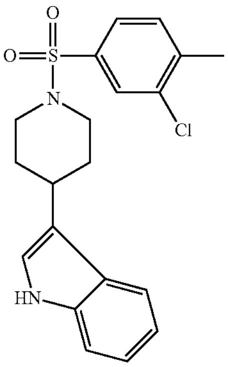
-continued
63
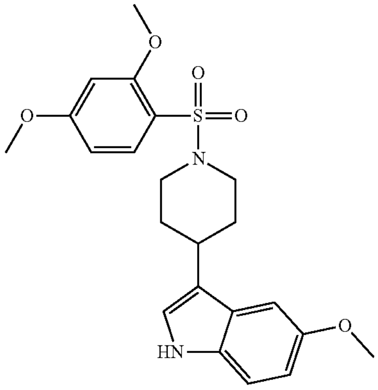
64
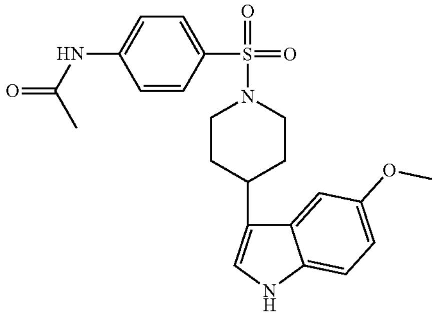
65
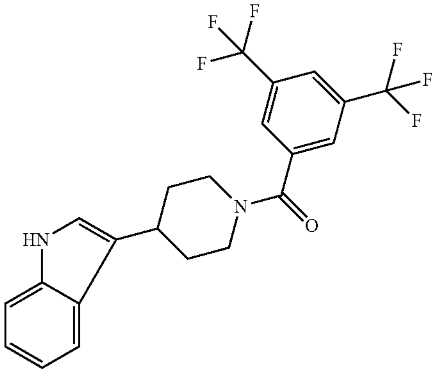
66
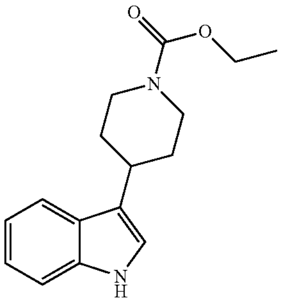

-continued
67
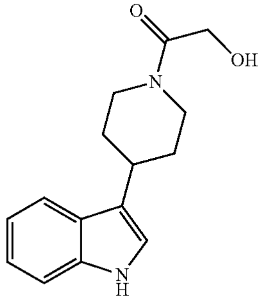
68
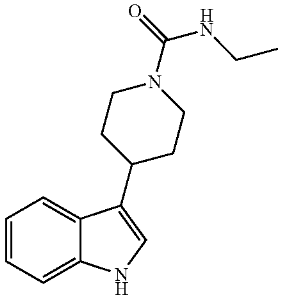
69
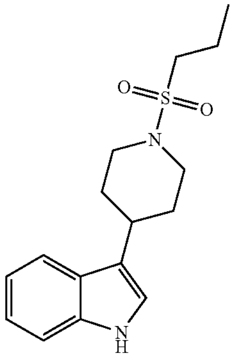
70
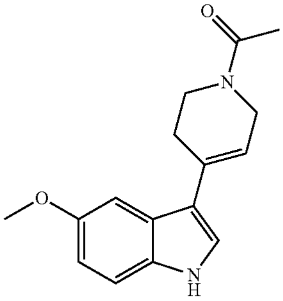
71
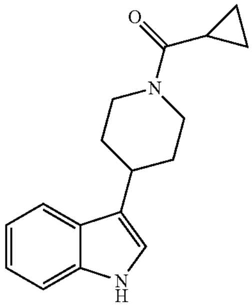
-continued
72
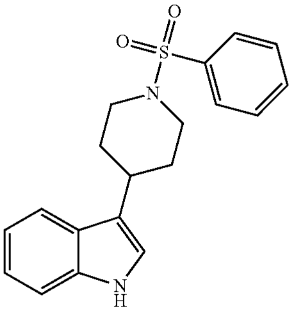
73
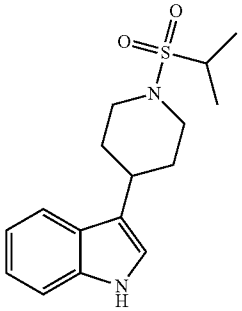
74
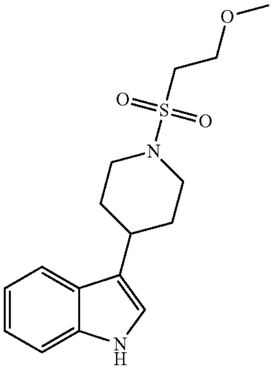
75
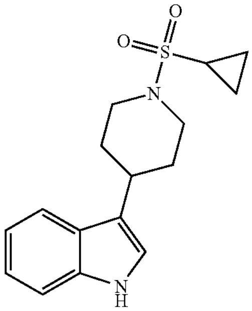
76
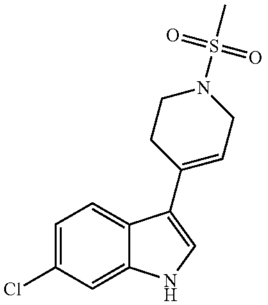

-continued
77
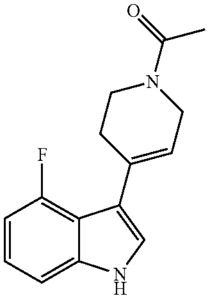
78
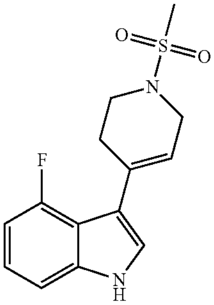
79
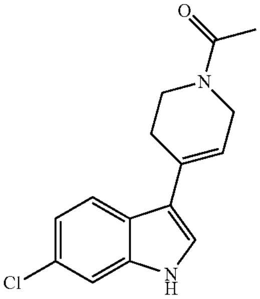
80
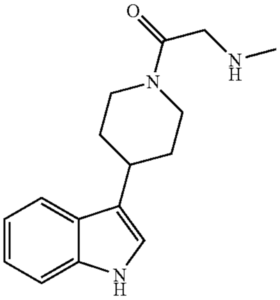
81
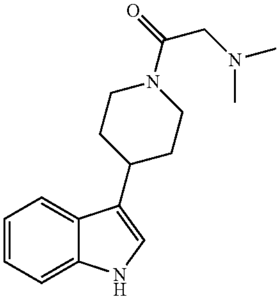
-continued
82
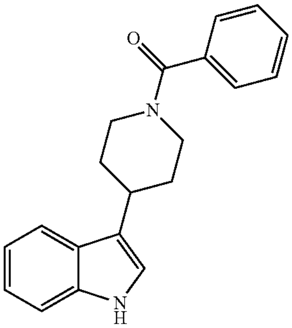
83
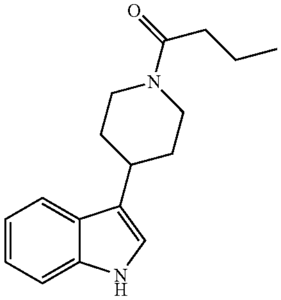
84
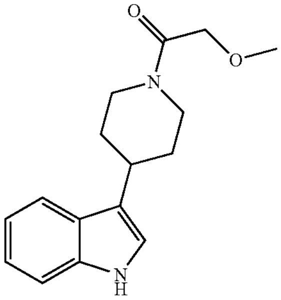
85
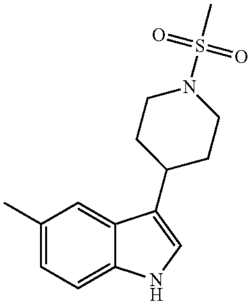
86
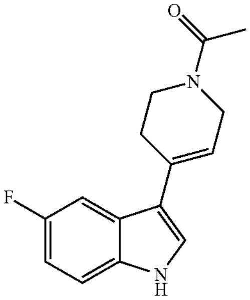

87
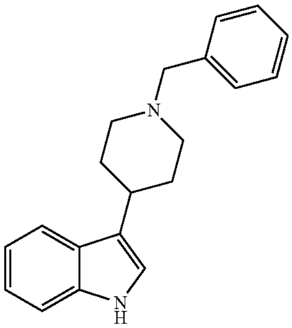
88
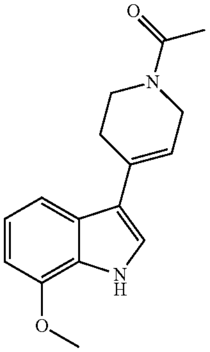
89
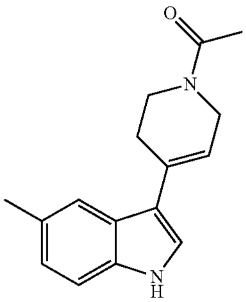
90
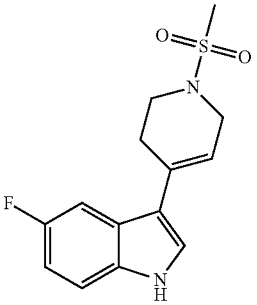
91
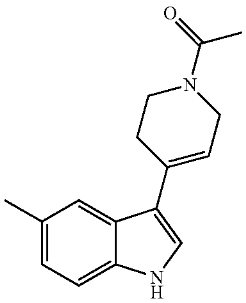
92
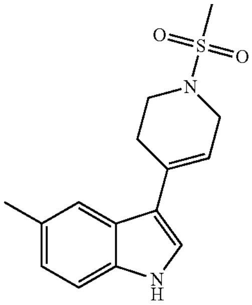
93
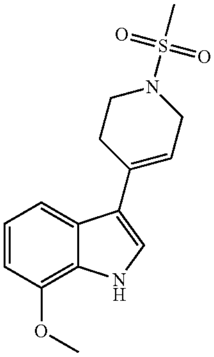
94
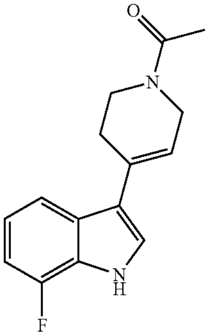
95
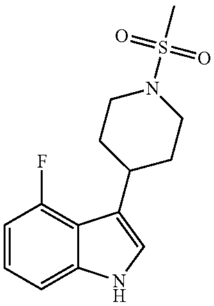
96
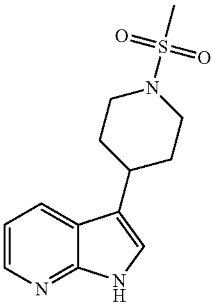

-continued
97
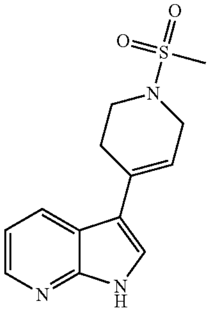
98
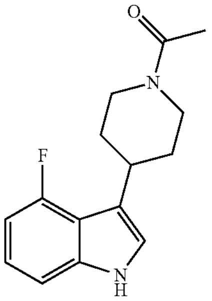
99
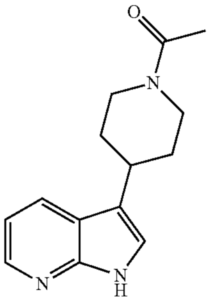
100
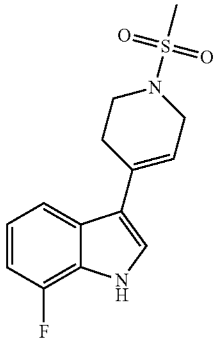
101
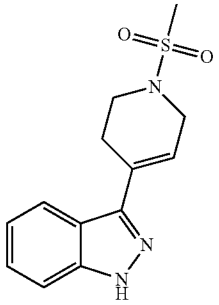
-continued
102
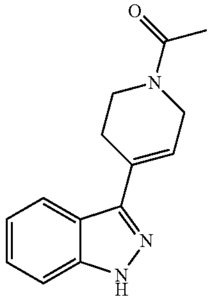
103
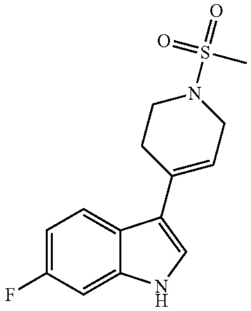
104
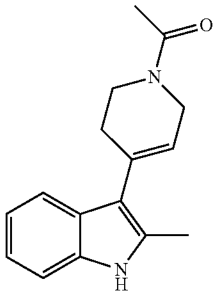
105
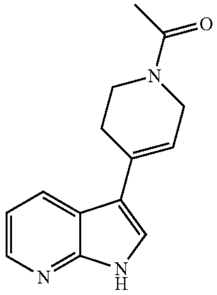
106
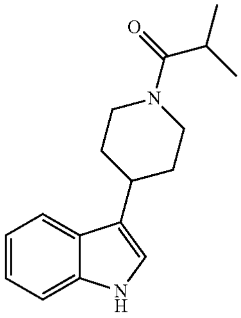

-continued
107
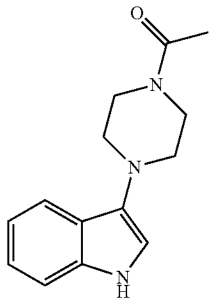
108
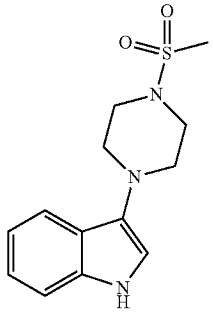
109
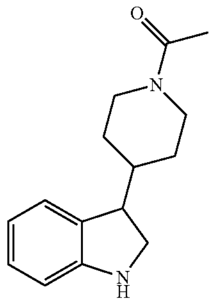
110
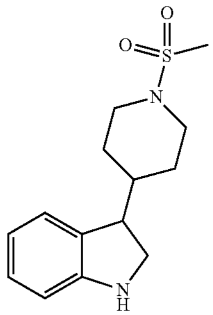
111
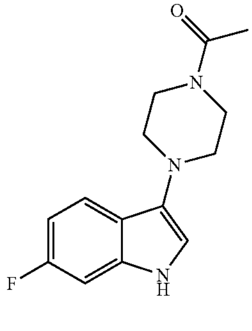
-continued
112
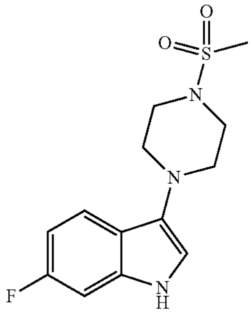
113
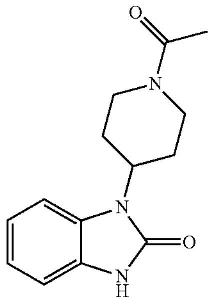
114
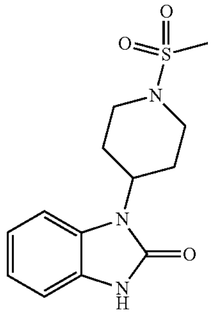
115
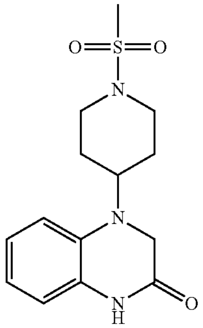
116
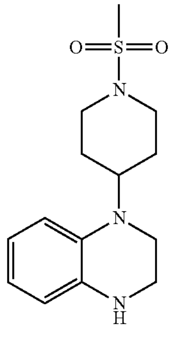

-continued
117
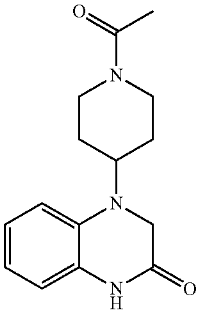
118
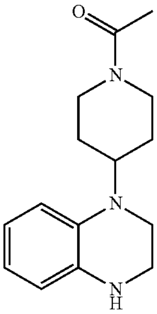
119
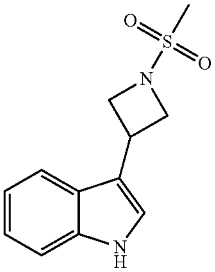
120
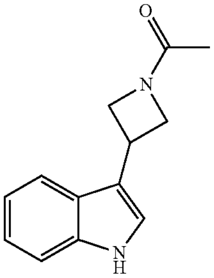
121
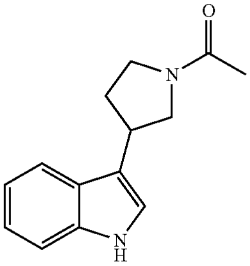
-continued
122
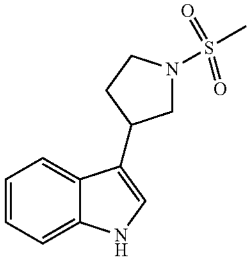
123
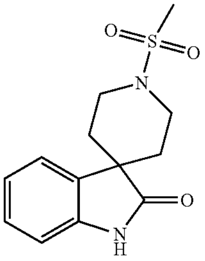
124
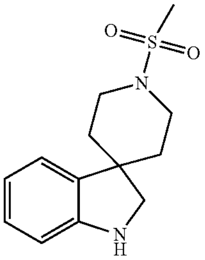
125
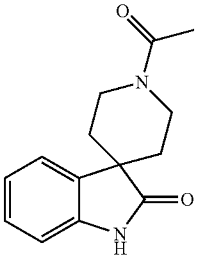
126
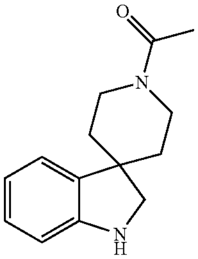
127
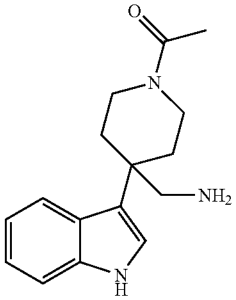

-continued
128
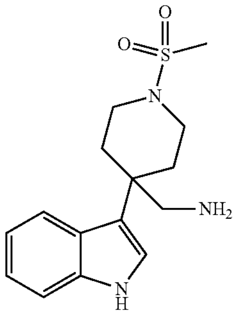
129
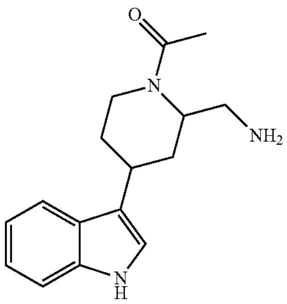
130
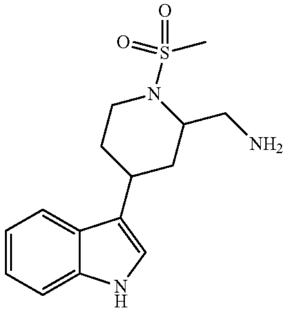
131
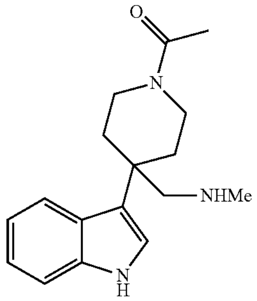
132
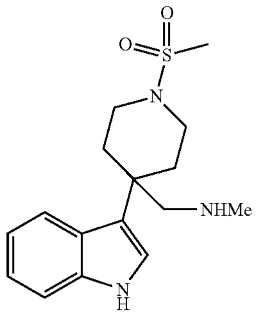
-continued
133
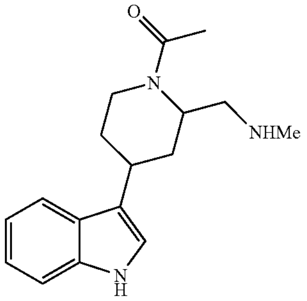
134
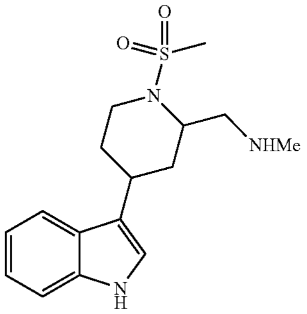
135
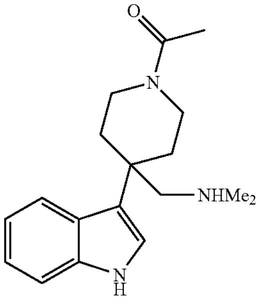
136
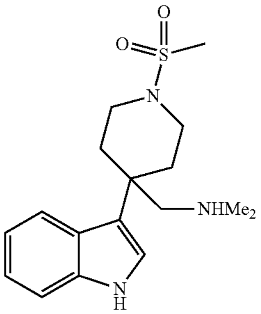
137
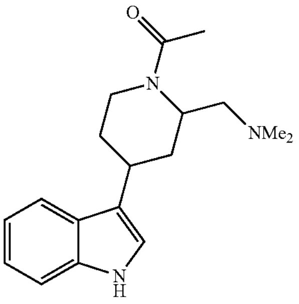

-continued
138
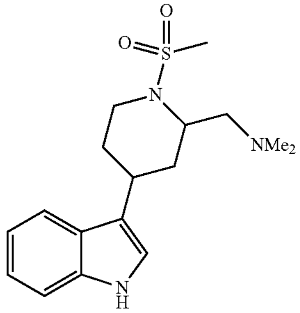
139
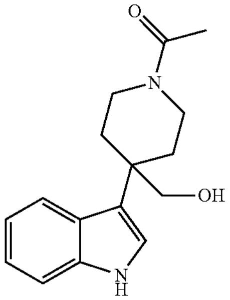
140
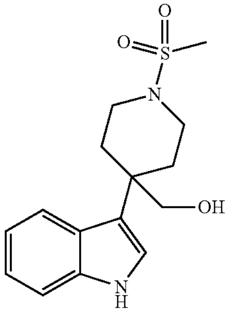
141
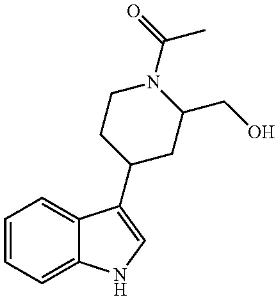
142
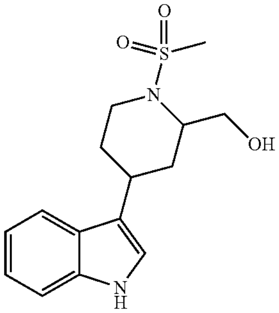
-continued
143
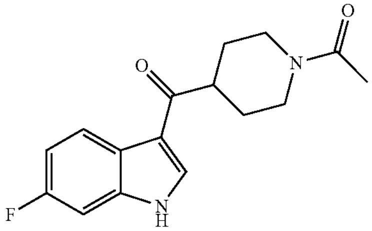
144
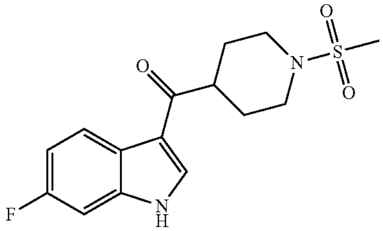
145
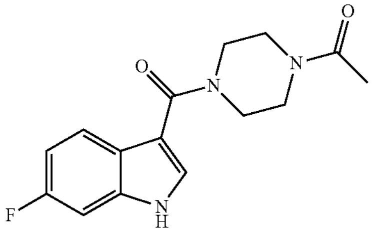
146
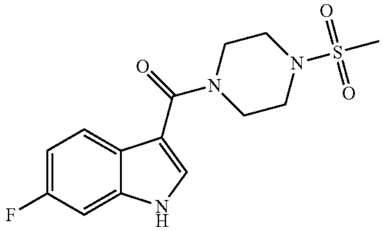
147
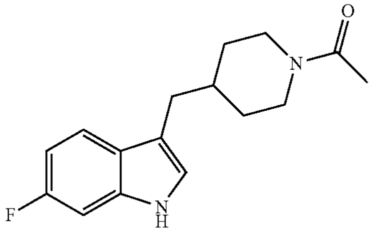
148
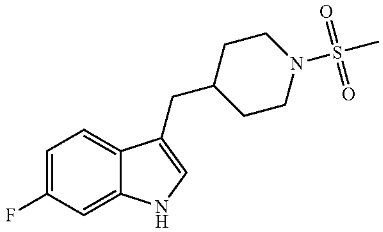

-continued
149
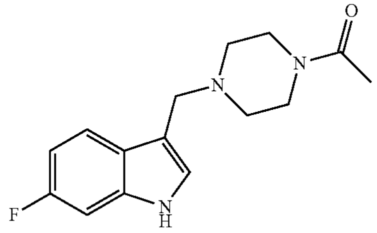
150
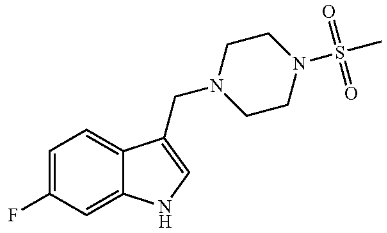
151
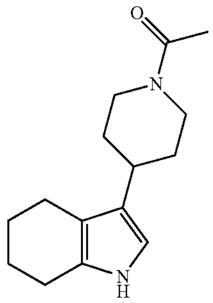
152
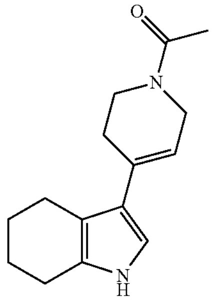
153
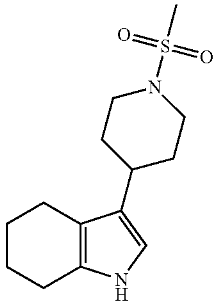
-continued
154
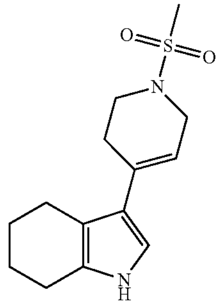
155
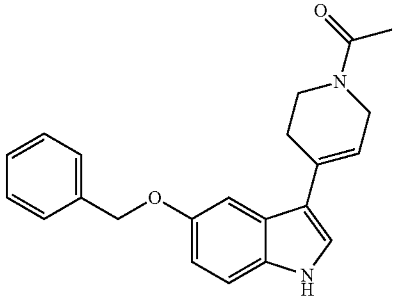
156
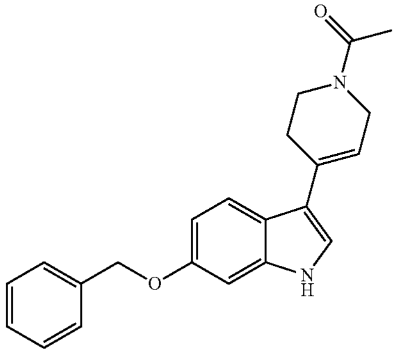
157
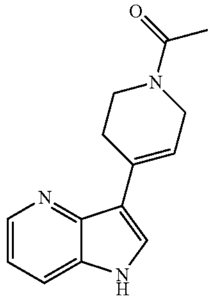
158
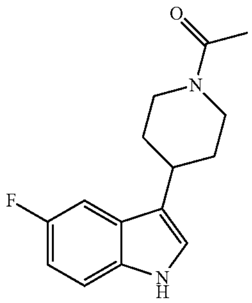

-continued
159
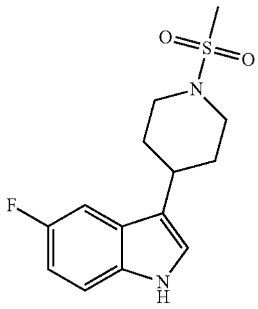
160
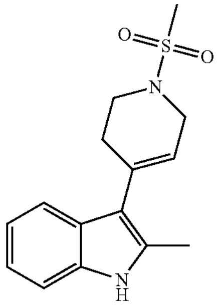
161
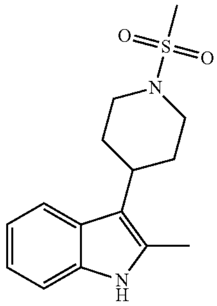
162
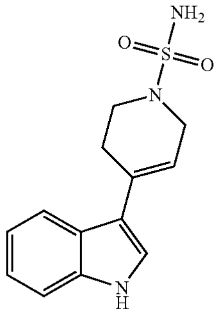
163
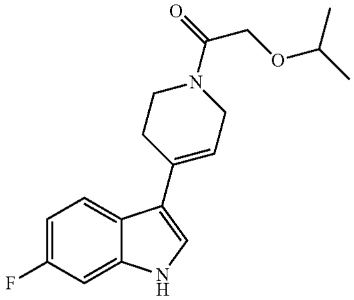
-continued
164
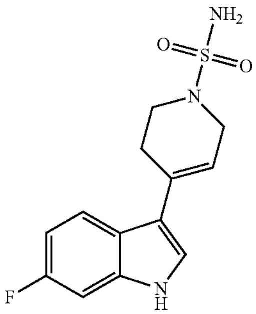
165
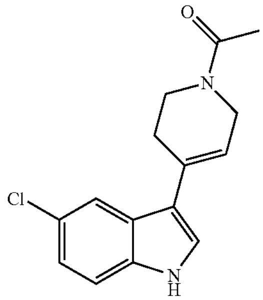
166
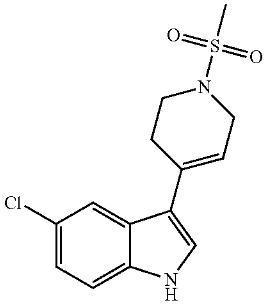
167
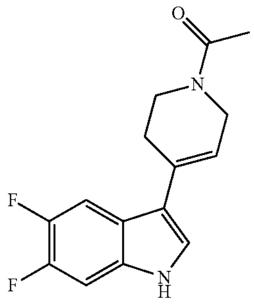
168
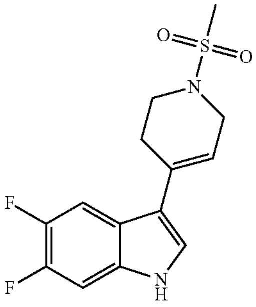

-continued
169
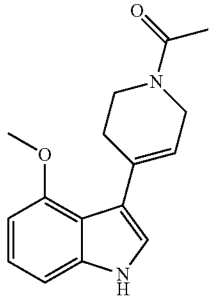
170
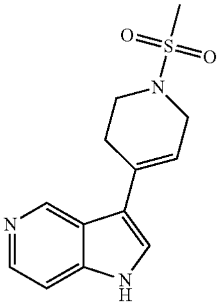
171
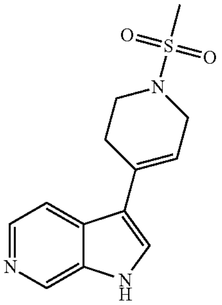
172
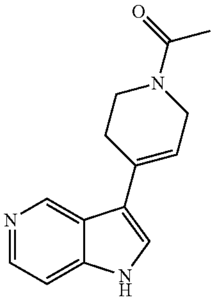
173
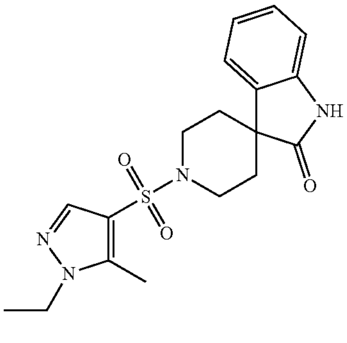
-continued
174
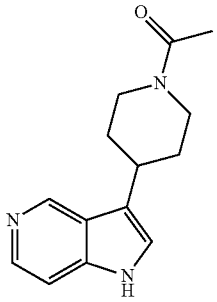
175
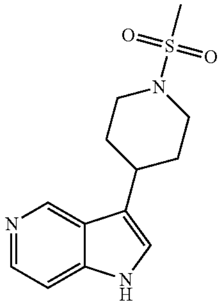
176
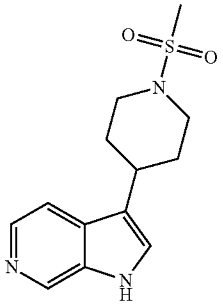
177
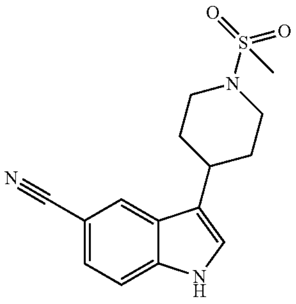
178
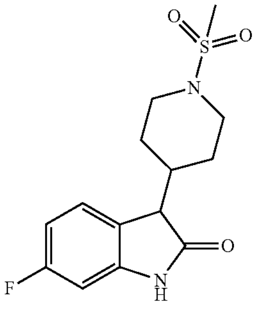

-continued
179
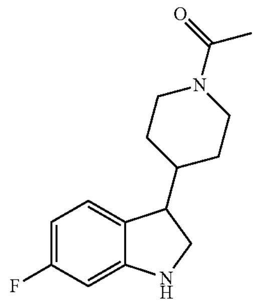
180
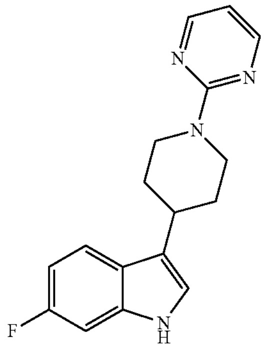
181
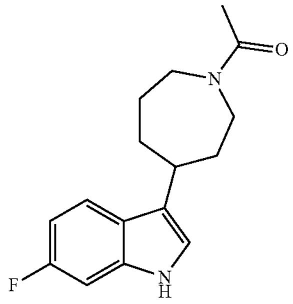
182
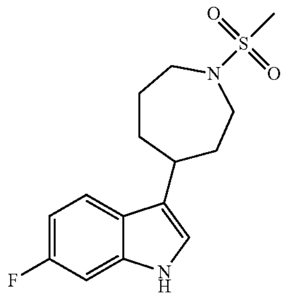
183
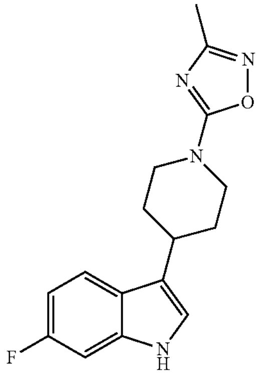
-continued
184
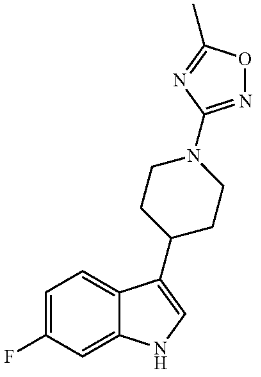
185
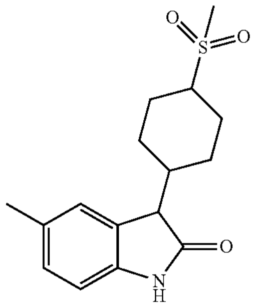
186
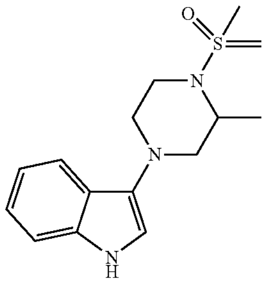
187
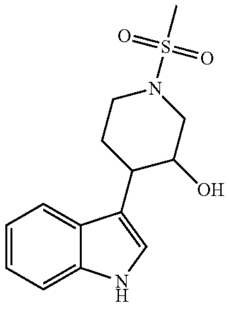
188
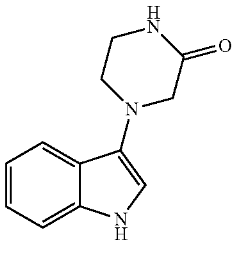

189
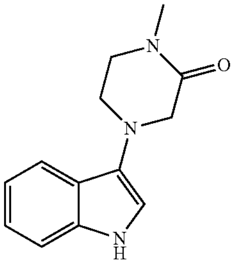
190
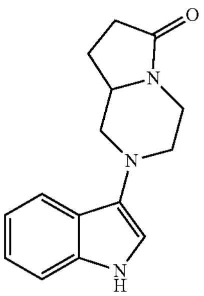
191
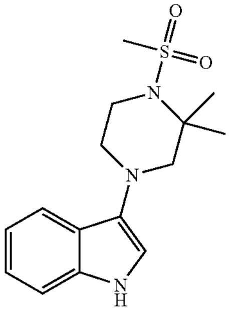
192
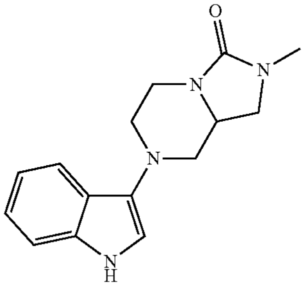
193
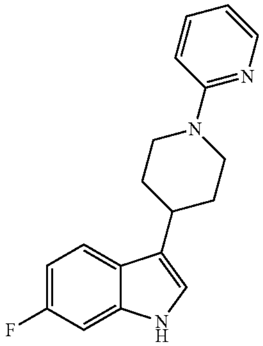
194
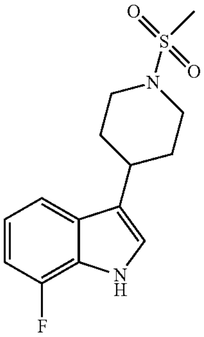
195
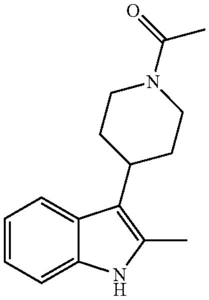
196
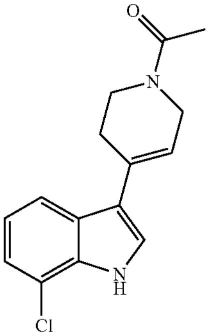
197
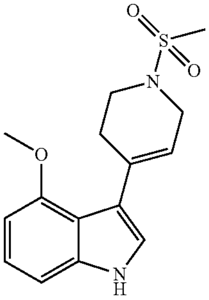
198
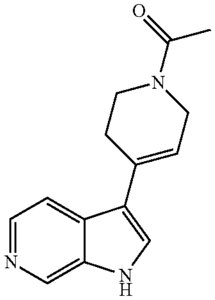

-continued
199
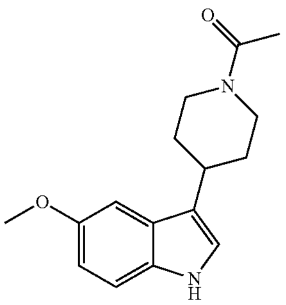
200
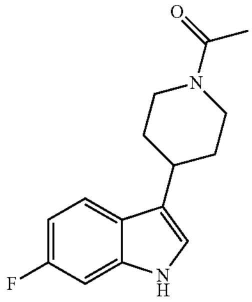
201
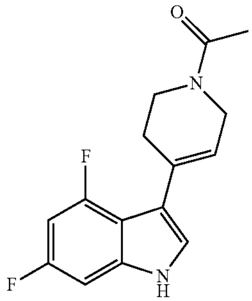
202
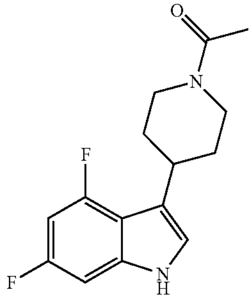
203
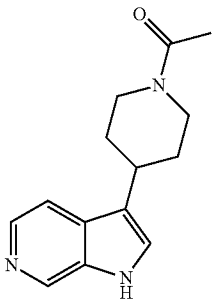
-continued
204
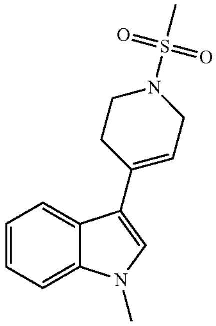
205
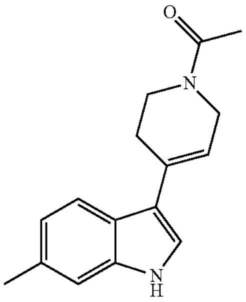
206
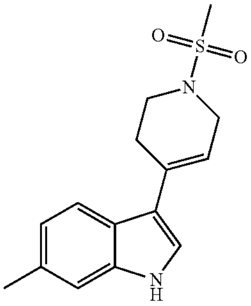
207
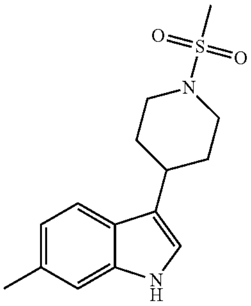
208
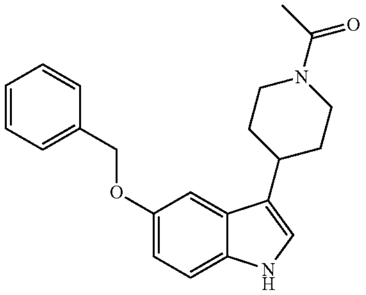

-continued
209
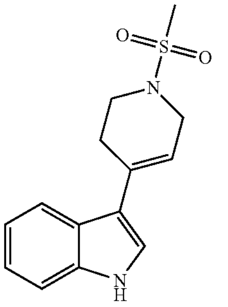
210
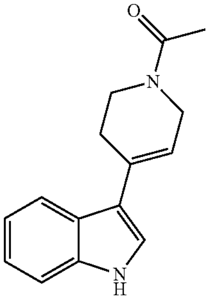
211
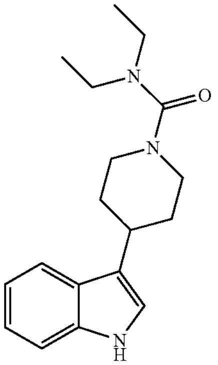
212
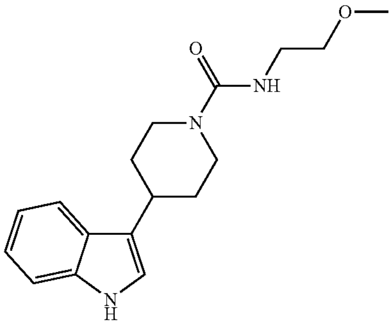
213
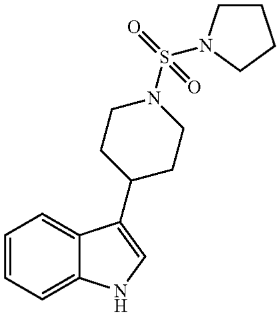
-continued
214
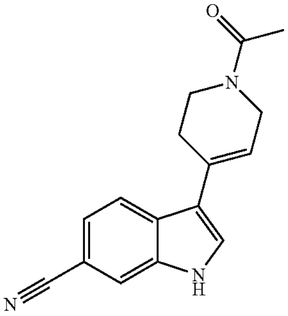
215
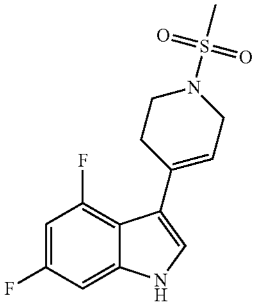
216
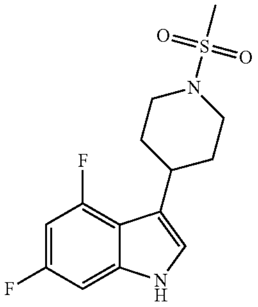
217
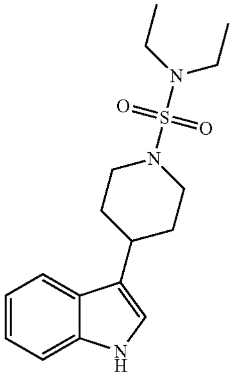
218
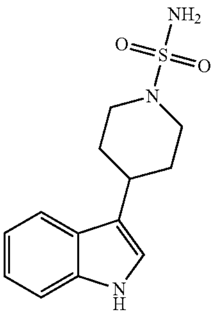

-continued
219
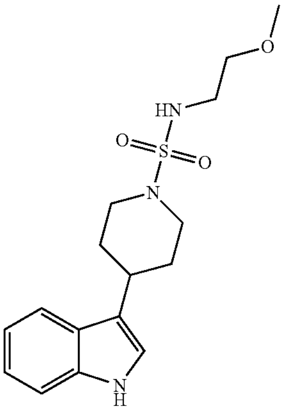
220
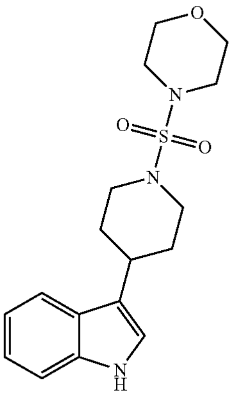
221
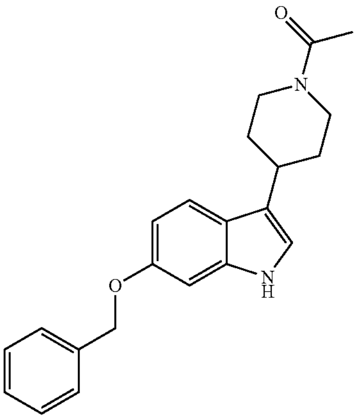
222
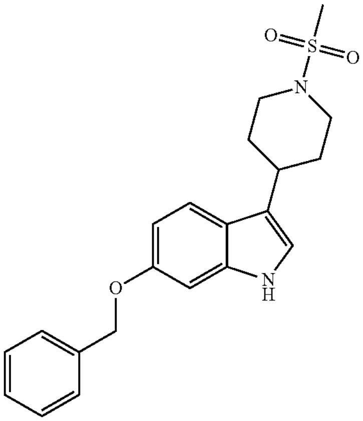
-continued
223
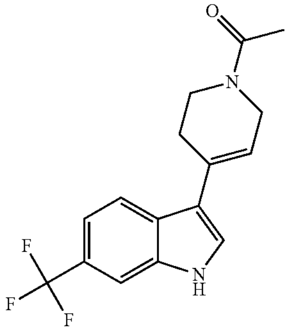
224
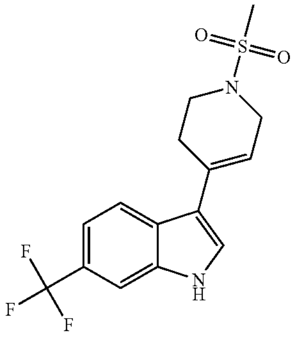
225
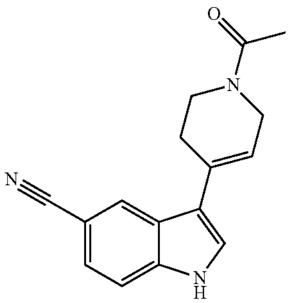
226
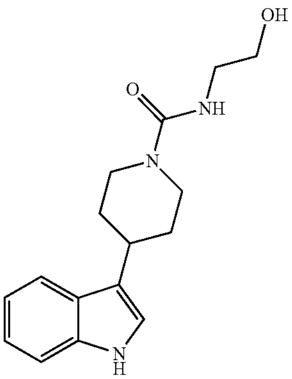

-continued
227
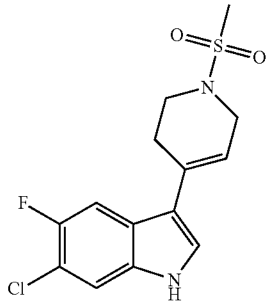
228
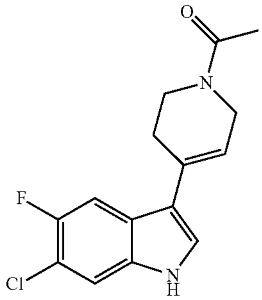
229
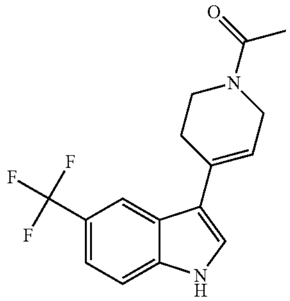
230
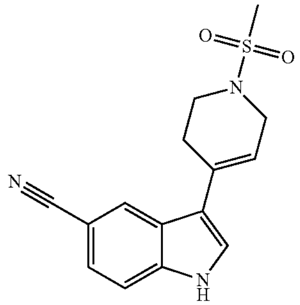
231
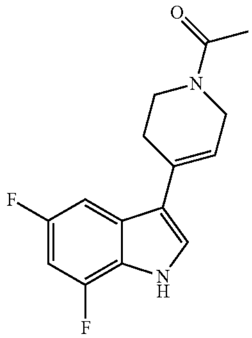
-continued
232
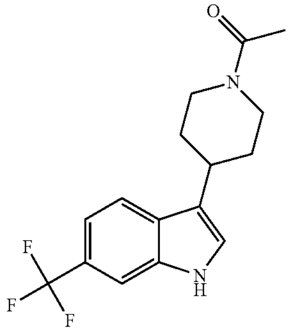
233
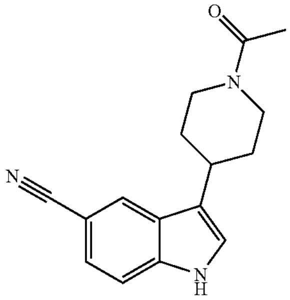
234
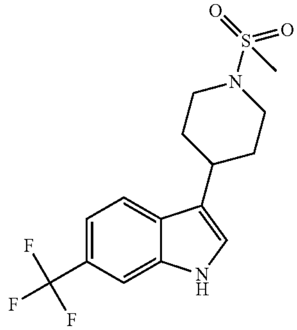
235
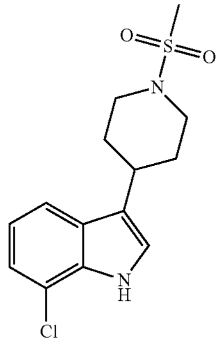
236
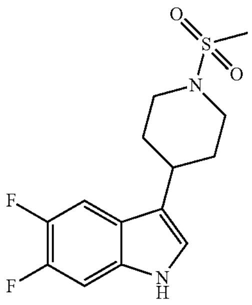

-continued
237
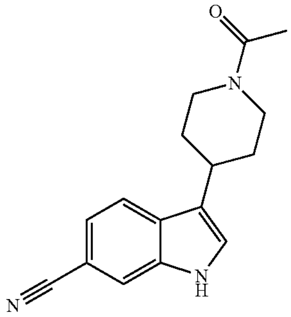
238
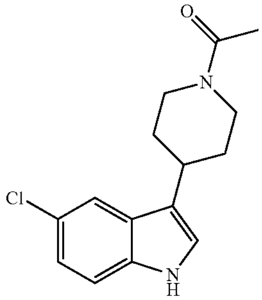
239
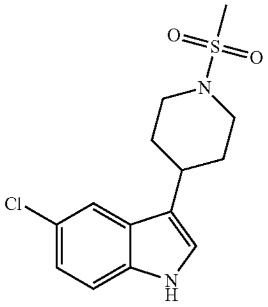
240
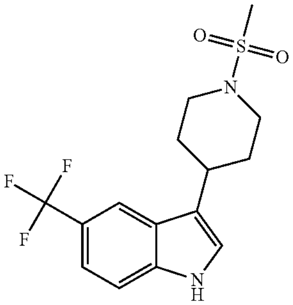
241
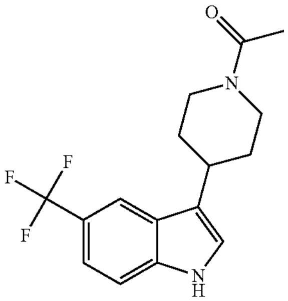
-continued
242
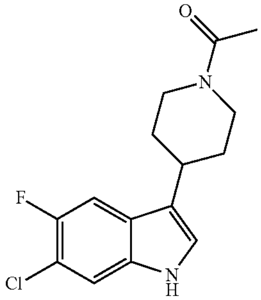
243
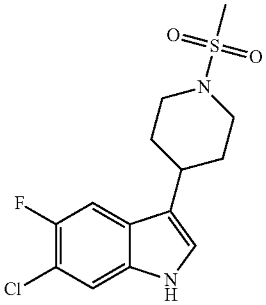
244
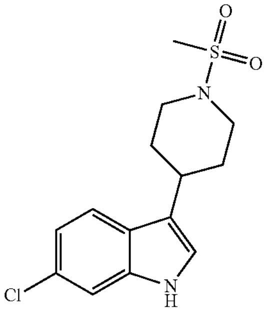
245
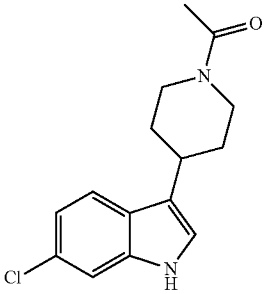
246
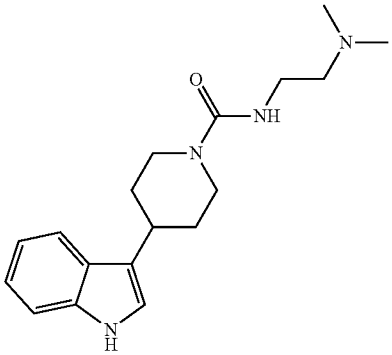

-continued
247
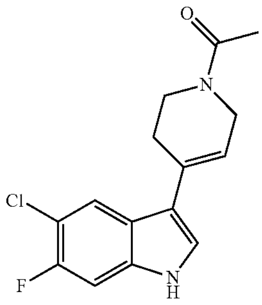
248
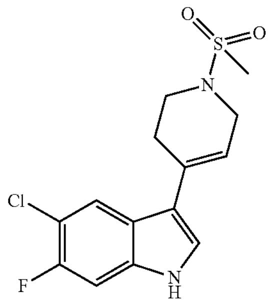
249
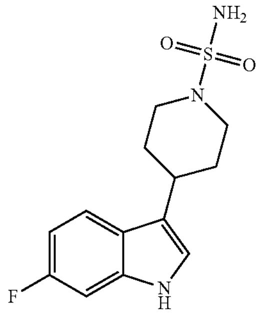
250
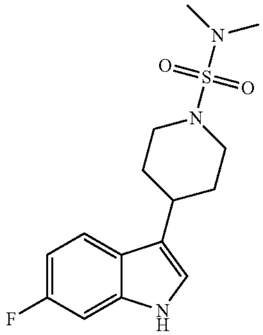
251
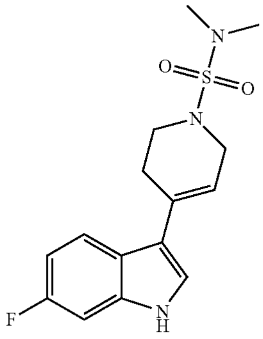
-continued
252
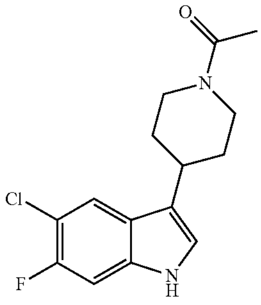
253
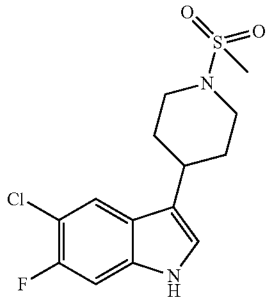
254
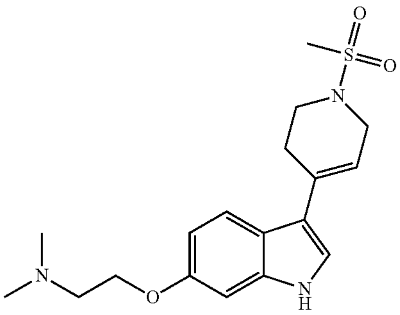
255
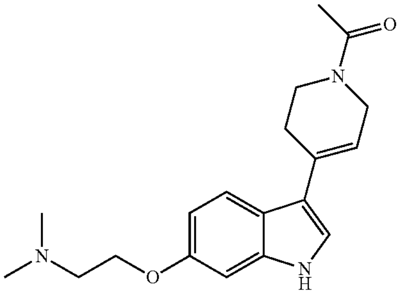
256
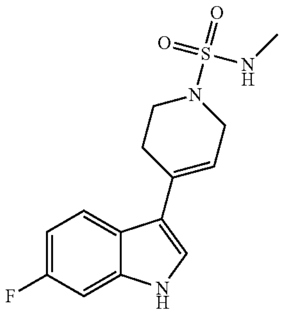

-continued
257
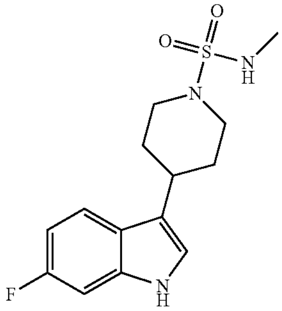
258
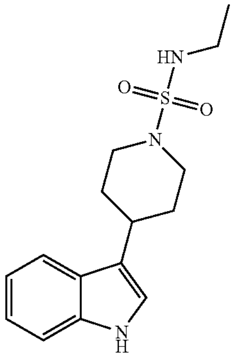
259
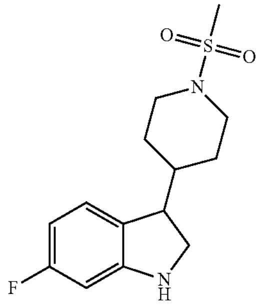
260
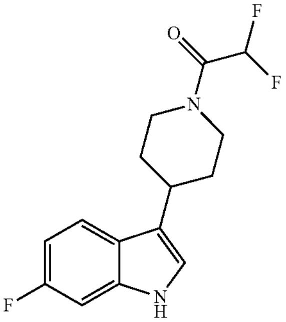
261
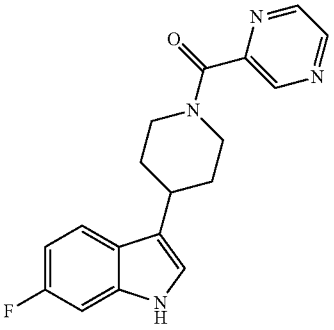
-continued
262
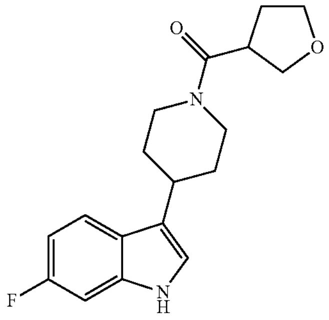
263
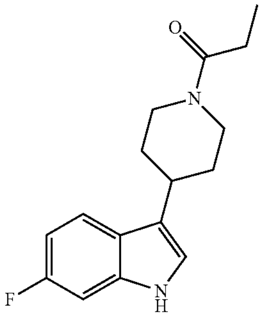
264
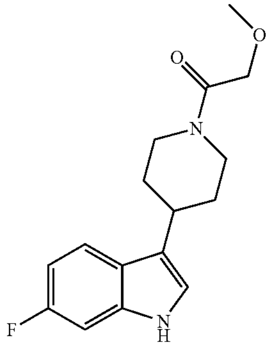
265
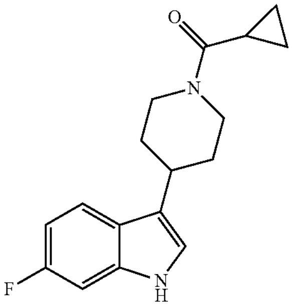
266
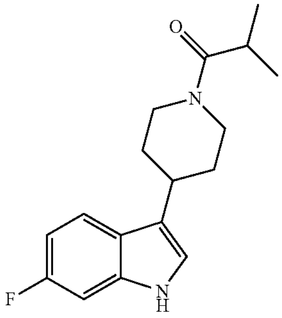

-continued
267
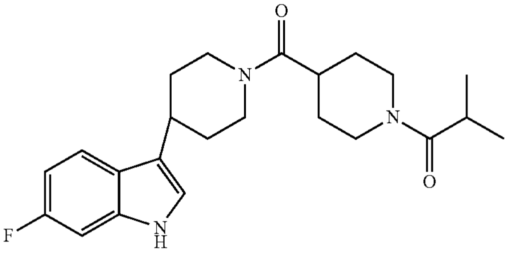
268
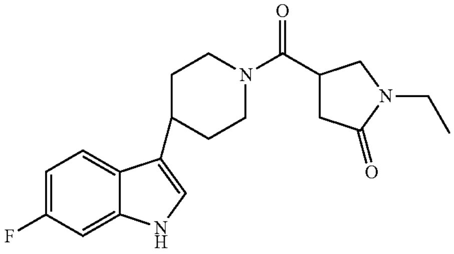
269
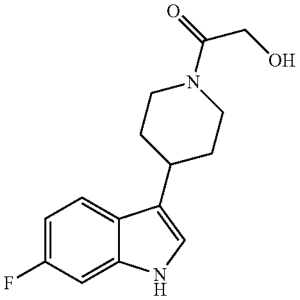
270
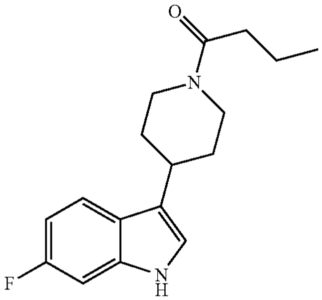
271
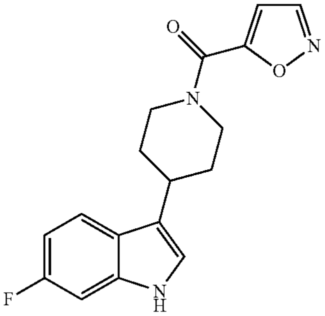
-continued
272
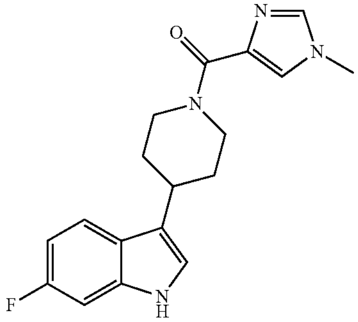
273
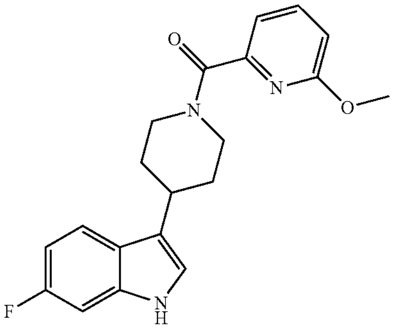
274
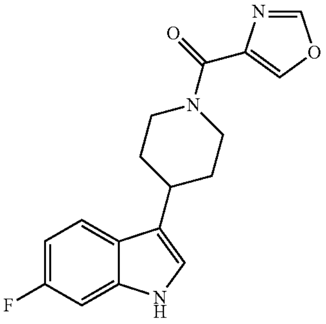
275
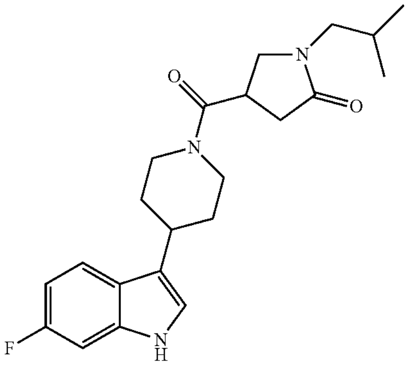

-continued
276
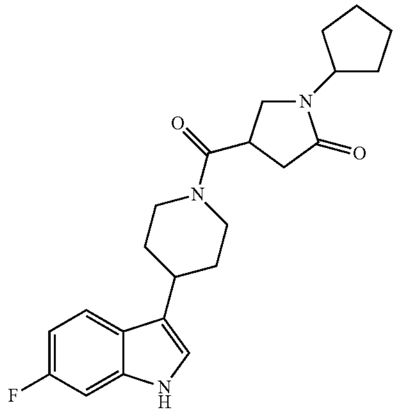
277
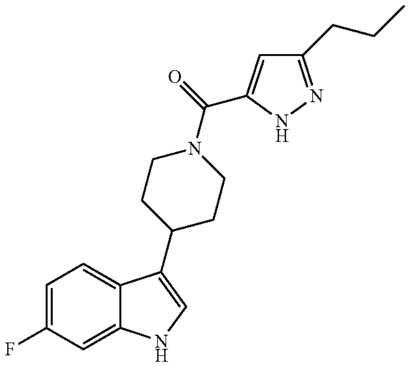
278
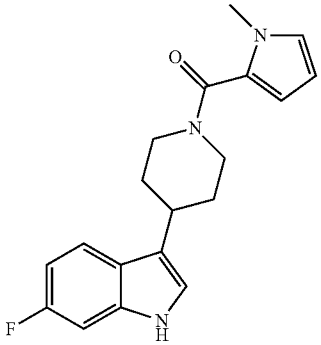
279
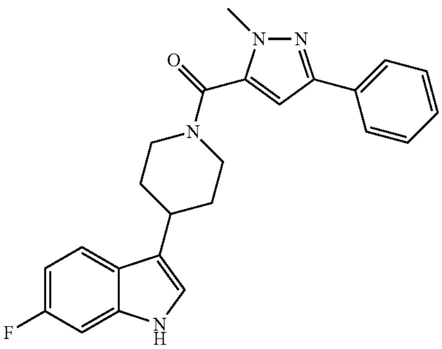
-continued
280
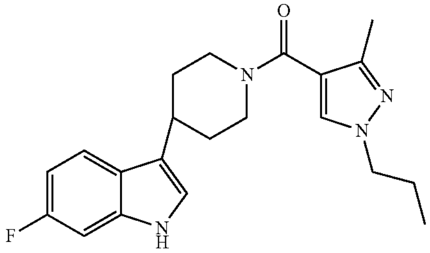
281
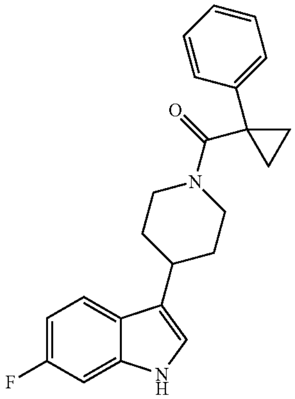
282
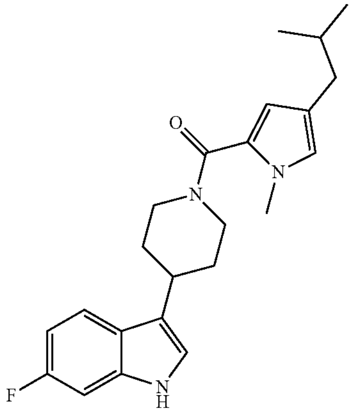
283
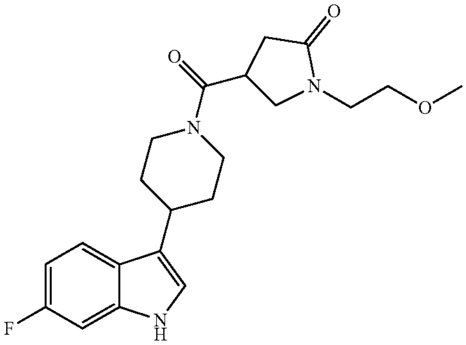

284
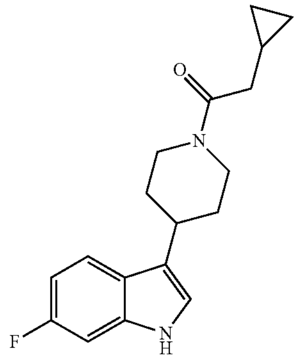
285
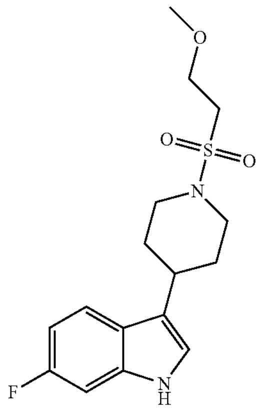
286
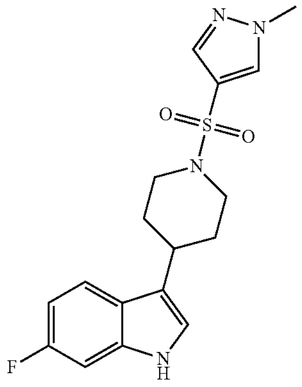
287
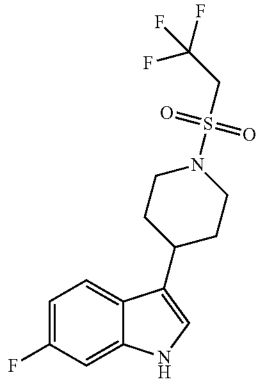
288
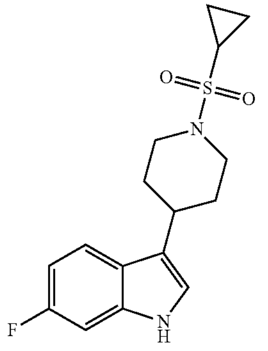
289
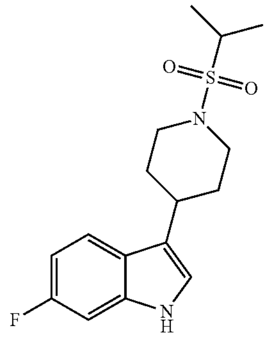
290
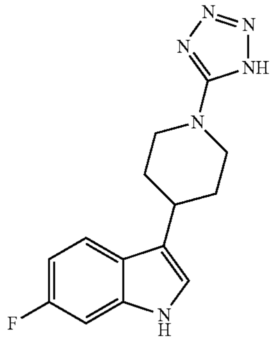
291
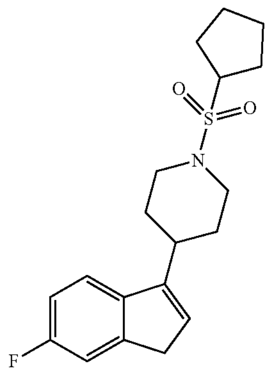

-continued
292
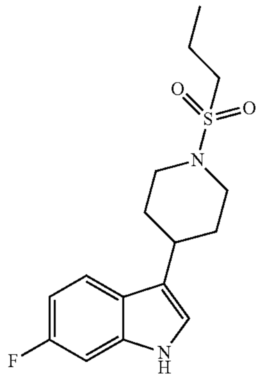
293
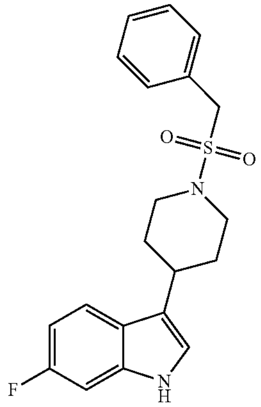
294
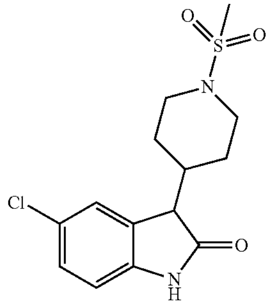
295
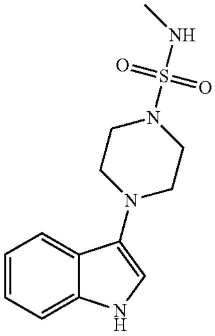
-continued
296
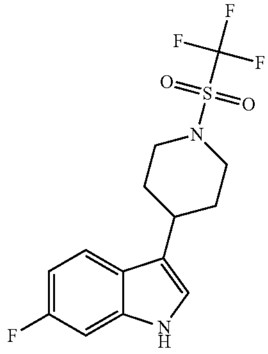
297
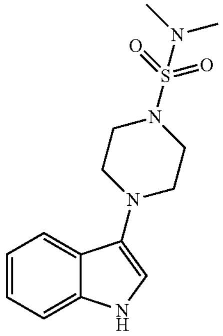
298
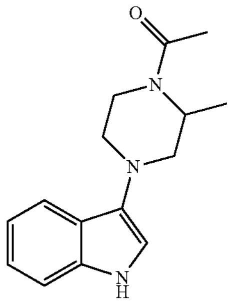
299
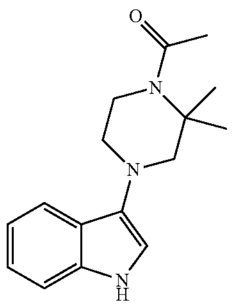

300
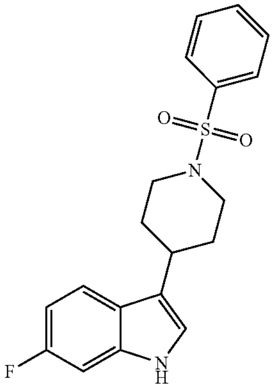
301
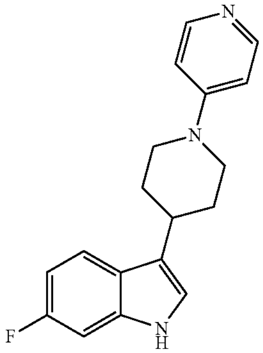
302
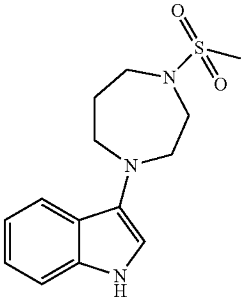
303
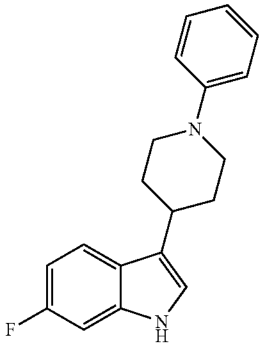
304
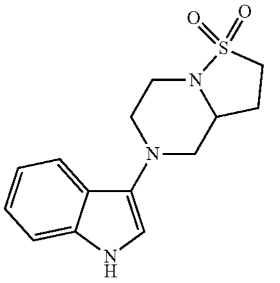
305
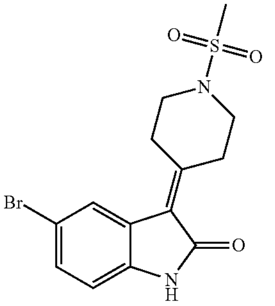
306
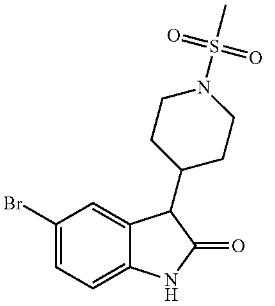
307
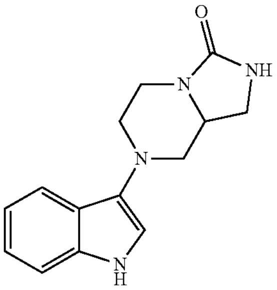
308
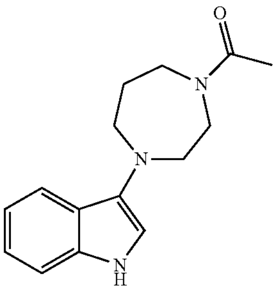

-continued
309
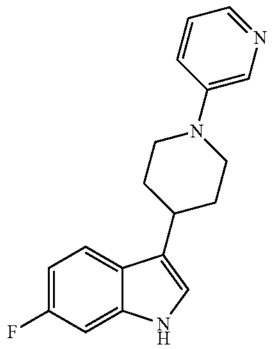
310
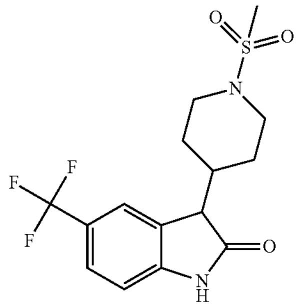
311
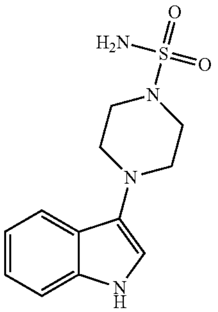
312
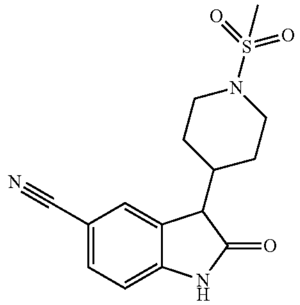
313
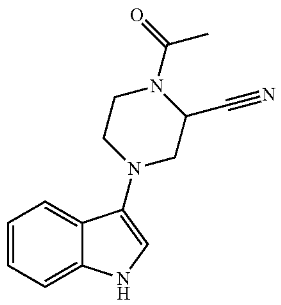
-continued
314
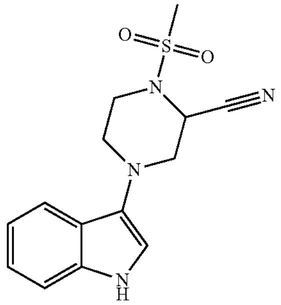
315
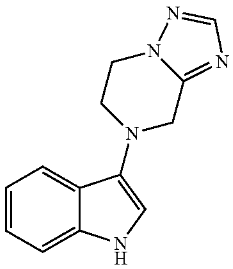
316
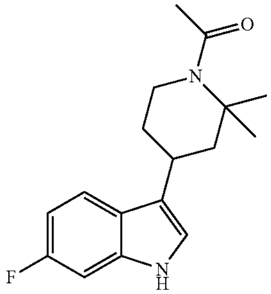
317
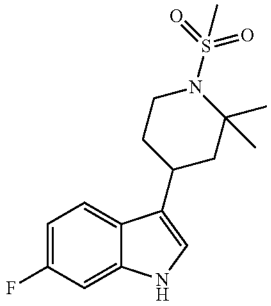
318
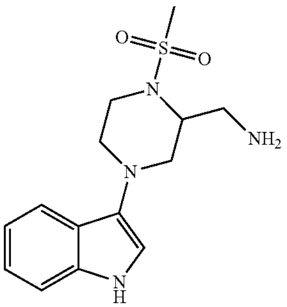

-continued

319

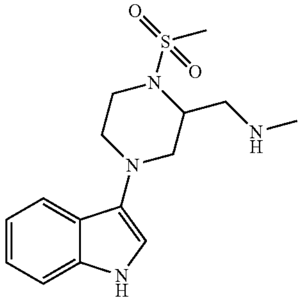

Typically, the above formulae (and all formulae herein) are shown in non-stereoisomeric form. For the avoidance of doubt, throughout the present disclosure a single formula is intended to represent all possible stereoisomers of a particular structure, including all possible isolated enantiomers corresponding to the formula, all possible mixtures of enantiomers corresponding to the formula, all possible mixtures of diastereomers corresponding to the formula, all possible mixtures of epimers corresponding to the formula and all possible racemic mixtures corresponding to the formula. In addition to this, the above formulae (and all formulae herein) are intended to represent all tautomeric forms equivalent to the corresponding formula.

In the context of the present invention, the medicinal use is not especially limited, provided that it is a use which is facilitated by the TDO and/or the IDO inhibitory effect of the compound. Thus, the compounds of the invention may be for use in any disease, condition or disorder that may be prevented, ameliorated or treated using a TDO and/or IDO inhibitor. Typically this comprises a disease condition and/or a disorder selected from: a cancer, an inflammatory condition, an infectious disease, a central nervous system disease or disorder, coronary heart disease, chronic renal failure, post anaesthesia cognitive dysfunction, a disease condition and/or a disorder relating to female reproductive health including contraception or abortion, and cataracts.

When the disease, condition or disorder is an inflammatory disease, condition or disorder, it is not especially limited, provided that the disease, condition or disorder is one which may be treated, prevented or ameliorated by using a TDO and/or IDO inhibitor. However, typically the inflammatory condition is a condition relating to immune B cell, T cell, dendritic cell, natural killer cell, macrophage, and/or neutrophil dysregulation.

When the disease, condition or disorder is a cancer, it is not especially limited, provided that the cancer is one which may be treated, prevented or ameliorated by using a TDO and/or IDO inhibitor. Thus the cancer may be a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, Proteus syndrome, and Proteus-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma). However, when the compound is an IDO inhibitor, typically (but not exclusively) the cancer is a cancer selected from acute myeloid leukemia (AML), a small-cell lung cancer, a melanoma, an ovarian cancer, a colorectal cancer, a pancreatic cancer, an endometrial cancer, and a skin papilloma. When the compound is a TDO inhibitor, typically (but not exclusively) the cancer is a cancer selected from a glioma, and a hepatocellular carcinoma.

When the disease is an infectious disease, it is not especially limited, provided that the disease is one which may be treated, prevented or ameliorated by using a TDO and/or IDO inhibitor. However, typically the infectious disease is selected from a bacterial infection and a viral infection, preferably a gut infection, sepsis, and sepsis induced hypotension.

When the disease, condition or disorder is a central nervous system disease, condition or disorder, it is not especially limited, provided that the disease, condition or disorder is one which may be treated, prevented or ameliorated by using a TDO and/or IDO inhibitor. However, the central nervous system disease, condition or disorder is typically selected from amyotrophic lateral sclerosis (AML), Huntington's disease, Alzheimer's disease, pain, a psychiatric disorder, multiple sclerosis, Parkinson's disease, and HIV related neurocognitive decline.

When the disease, condition or disorder is one relating to female reproductive health, it is not especially limited provided that the disease, condition or disorder is one which may be treated, prevented or ameliorated by using a TDO and/or IDO inhibitor. In typical embodiments the disease, condition or disorder is selected from gynaecological disorders such as endometriosis. Conditions relating to female reproductive health that are included in the invention include contraception and abortion such that the compounds of the invention may be used as a contraceptive and/or abortive agent.

The present invention also provides a pharmaceutical composition comprising a compound as defined above. Whilst the pharmaceutical composition is not especially limited, typically the composition further comprises a pharmaceutically acceptable additive and/or excipient. Typically, the composition is for treating a disease, condition or disorder as defined above.

In some embodiments the pharmaceutical composition is a composition for treating a cancer, further comprising a further agent for treating cancer. The further agent for treating cancer is not especially limited, provided that it affords some utility for cancer treatment. However, typically the further agent for treating cancer is selected from anti-microtubule agents, platinum coordination complexes, alkylating agents, antibiotic agents, topoisomerase II inhibitors, antimnetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors. An immunotherapeutic agent may consist of but is not limited to an anti-tumour vaccine, an oncolytic virus, an immune stimulatory antibody such as anti-CTLA4, anti-PD1, anti-PDL-1, anti-OX40, anti-41BB, anti-CD27, anti-CD137, and anti-GITR, a novel adjuvant, a peptide, a cytokine, a chimeric antigen receptor T cell therapy (CAR-T), a small molecule immune modulator, tumour microenvironment modulators, and anti-angiogenic agents.

In still further embodiments the invention provides a pharmaceutical kit for treating a cancer, which pharmaceutical kit comprises:

(a) a compound as defined above; and (b) a further agent for treating cancer; preferably wherein the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors;

wherein the compound and the further agent are suitable for administration simultaneously, sequentially or separately.

Further provided by the invention is a method of treating a disease and/or a condition and/or a disorder, which method comprises administering to a patient (or subject) a compound, or a composition, or a kit as defined above. The method is typically a method for treating any disease condition or disorder mentioned herein. In typical embodiments, the method is a method for treating a cancer. Preferably such a method comprises administering to a patient (or subject) a compound or a composition as defined above and a further agent for treating cancer as defined above. The compound or composition and the further agent may administered simultaneously, sequentially or separately, depending upon the agents and patients involved, and the type of cancer indicated.

Typically, in all embodiments of the invention, both above and below, the patient (or subject) is an animal, typically a mammal, and more typically a human.

Further provided by the invention is a method of synthesis of a compound as defined above, which method comprises a step of substituting the substituent (typically an H group) at the 3-position of a substituted or unsubstituted indole or azaindole compound, with a different substituent. Typically the different substituent is substituted or unsubstituted piperidine or a substituted or unsubstituted tetrahydropyridine group. However, in some embodiments, the different substituent is a precursor to a substituted or unsubstituted piperidine or a substituted or unsubstituted tetrahydropyridine group.

In typical embodiments, this method of synthesis is carried out by refluxing under acid or base catalysis. The skilled person may select the type and strength of acid or base, and the reaction conditions, with reference to known synthesis techniques. In some embodiments, the method comprises an additional hydrogenation step. The skilled person may select the reaction conditions, with reference to known synthesis techniques.

In addition to compounds for use in medicine, the present invention, and in particular the synthetic method, provides compounds that were not previously known, such compounds comprising a formula selected from one of the following:

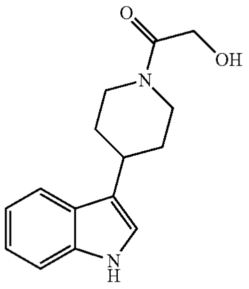

67

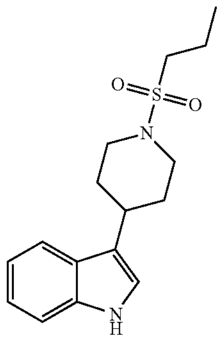

69

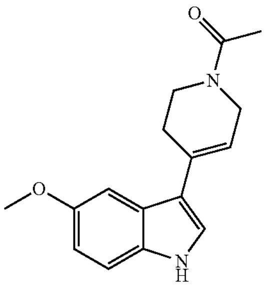

70

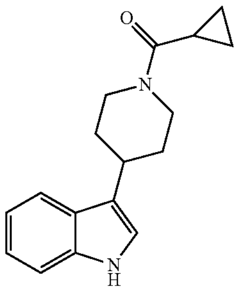

71

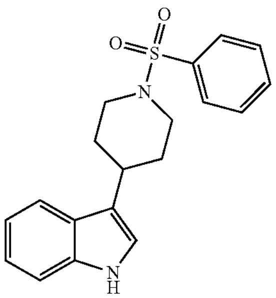

72

-continued
73
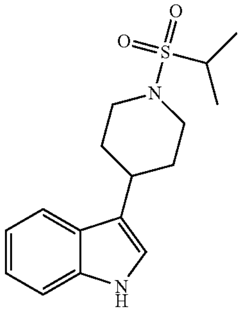
74
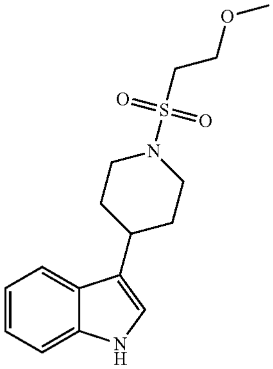
75
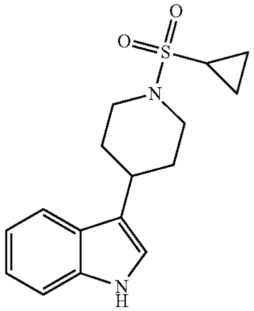
76
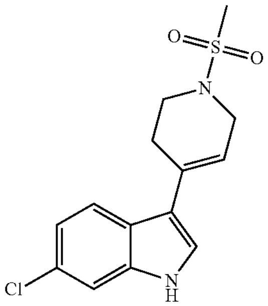
77
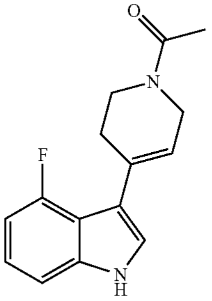
-continued
78
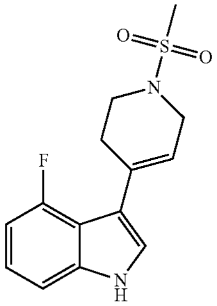
79
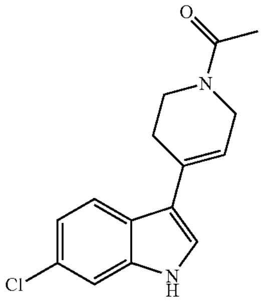
80
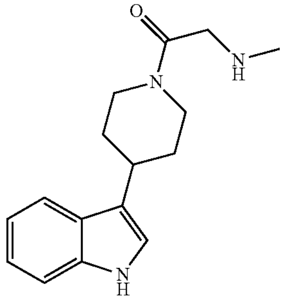
85
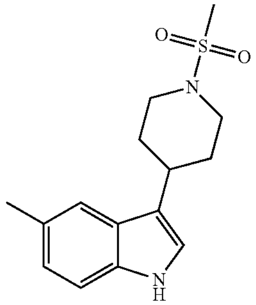
86
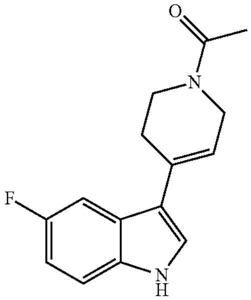

-continued
88
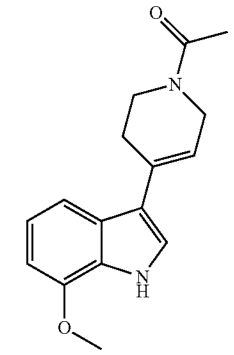
89
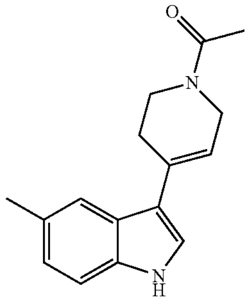
90
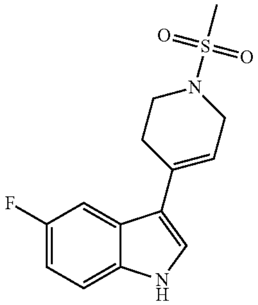
91
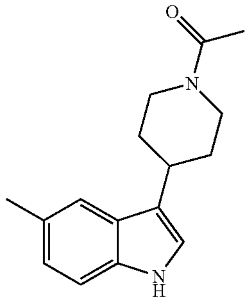
92
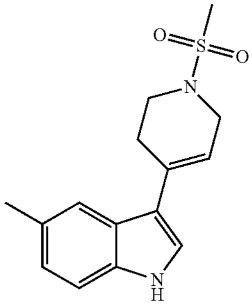
-continued
93
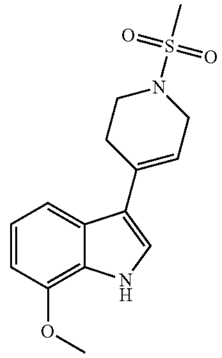
94
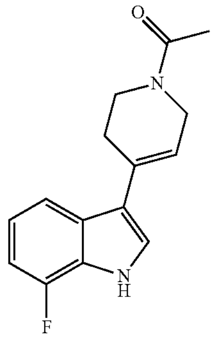
95
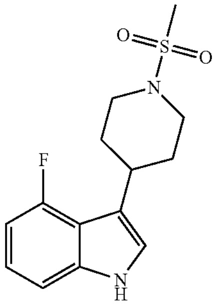
96
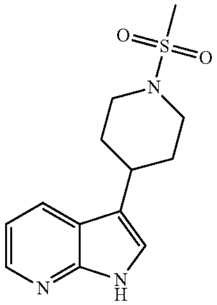
97
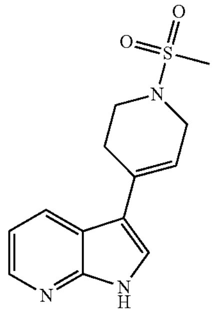

-continued
98
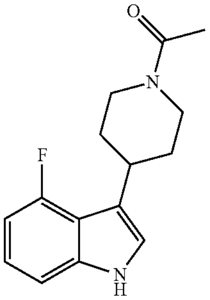
99
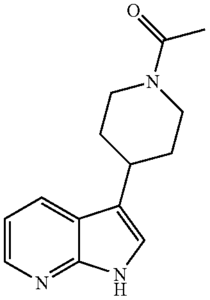
100
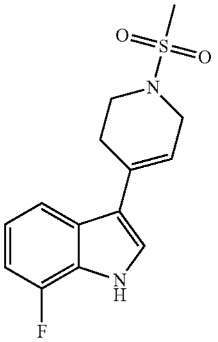
101
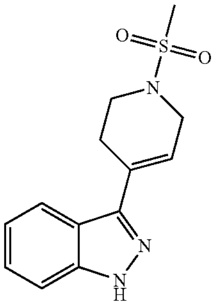
102
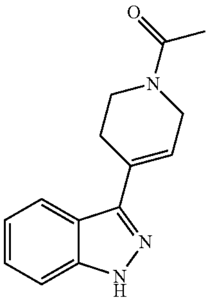
-continued
106
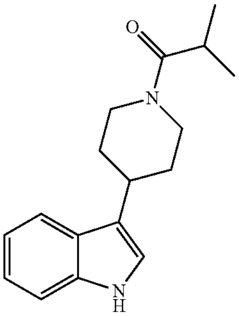
107
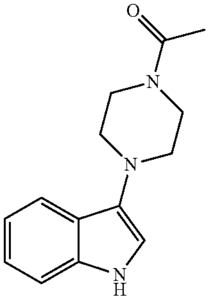
108
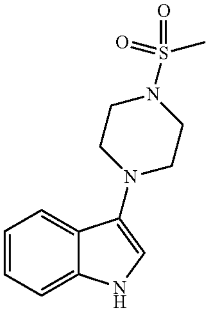
110
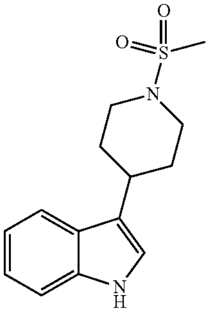
111
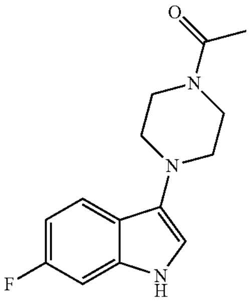

-continued
112
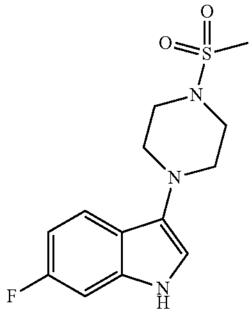
115
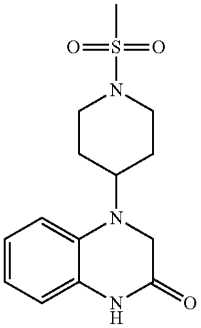
116
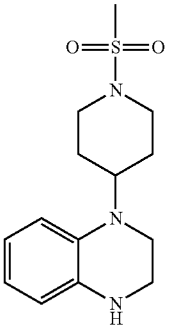
117
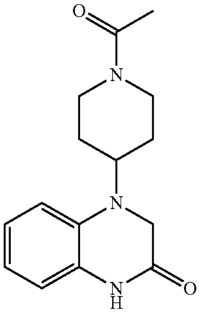
118
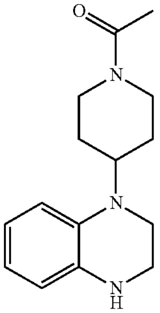
-continued
119
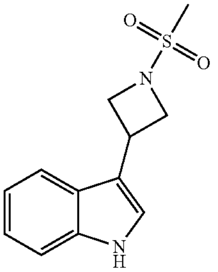
120
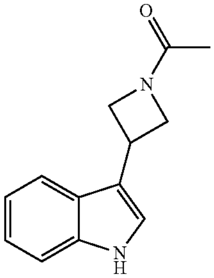
121
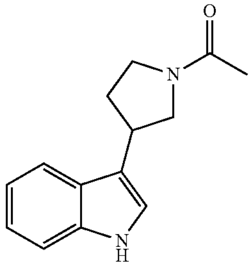
122
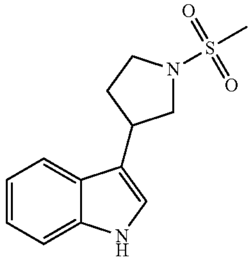
123
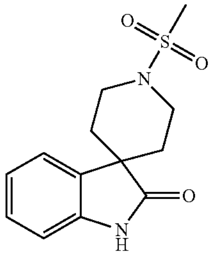
124
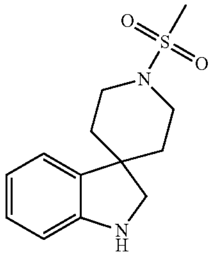

-continued
126
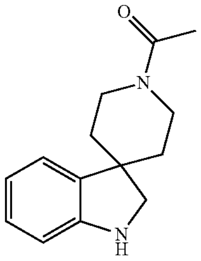
127
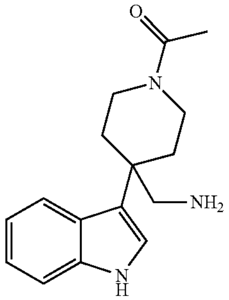
128
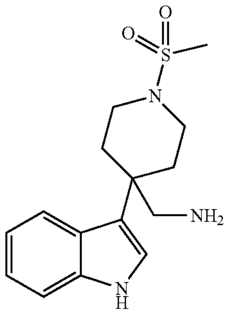
129
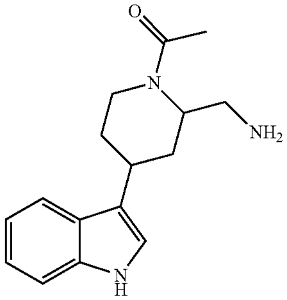
130
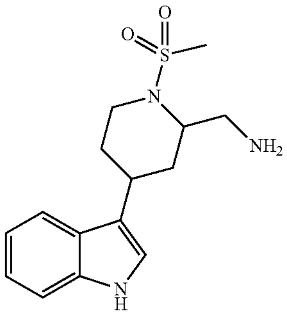
-continued
131
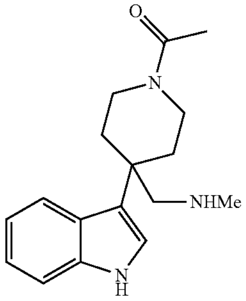
132
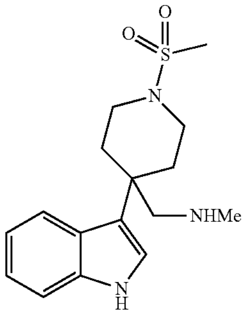
133
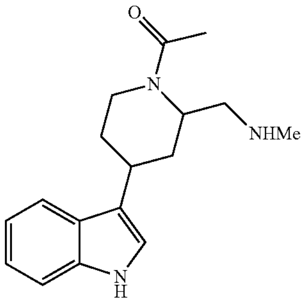
134
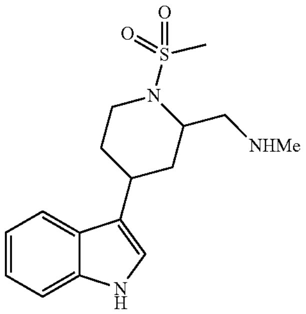
135
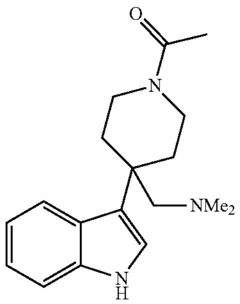

136
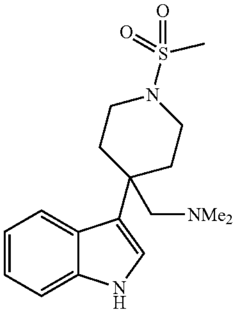
137
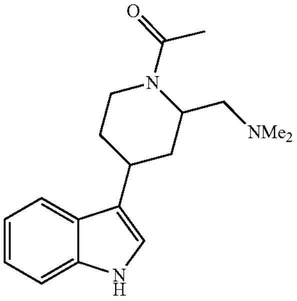
138
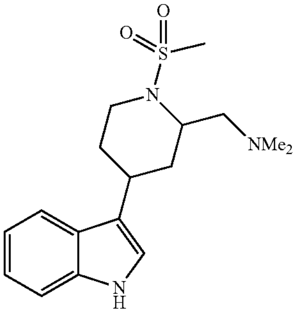
139
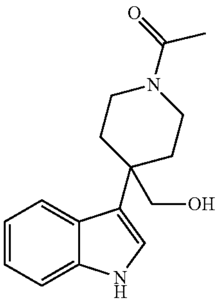
140
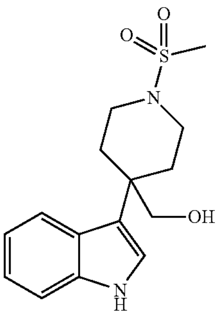
141
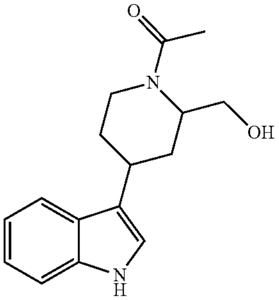
142
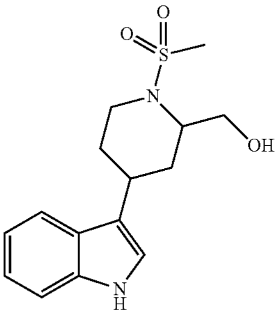
143
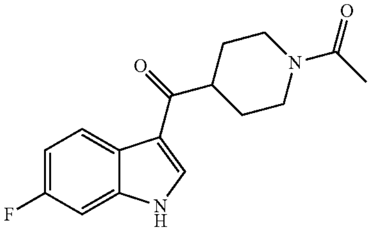
144
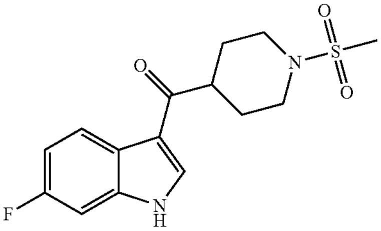
145
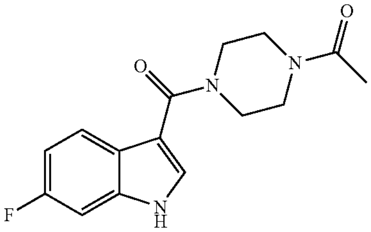
146
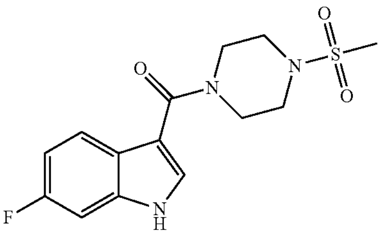

-continued
147
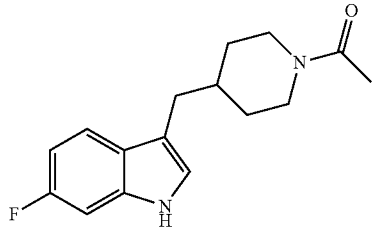
148
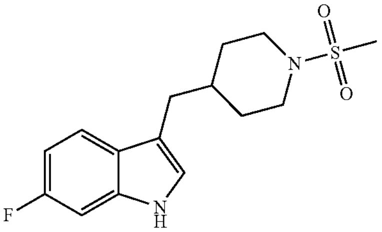
149
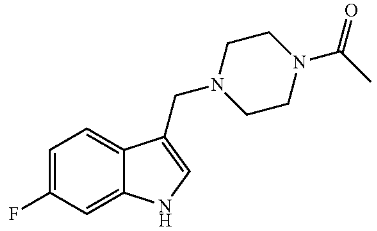
150
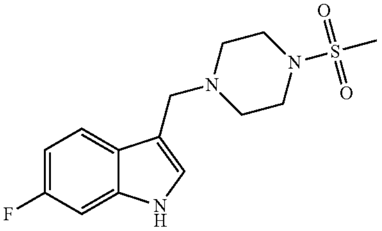
151
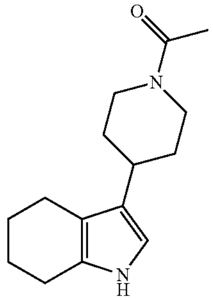
152
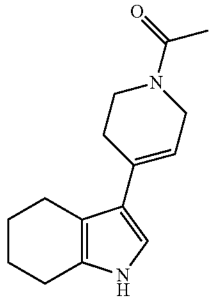
-continued
153
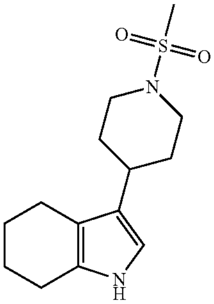
154
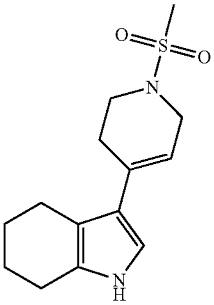
155
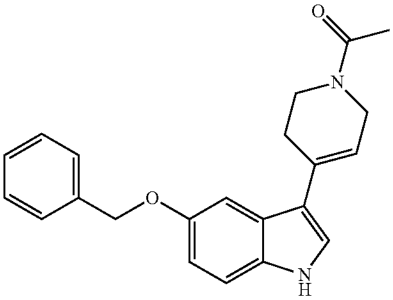
156
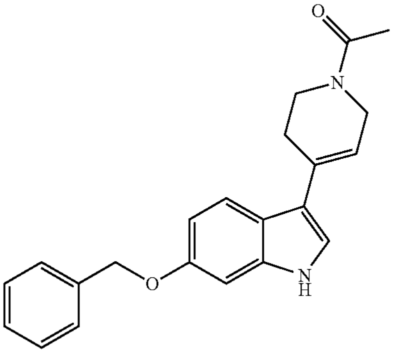
157
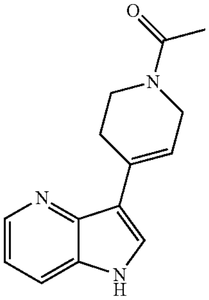

-continued
158
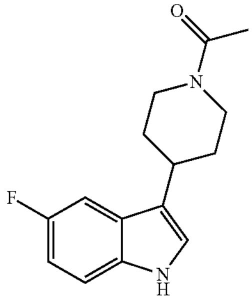
159
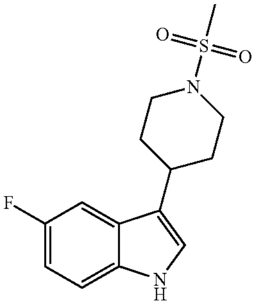
160
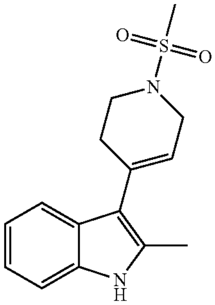
161
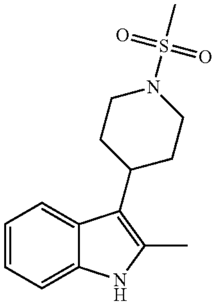
165
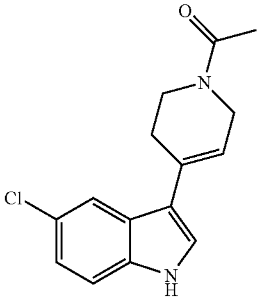
-continued
166
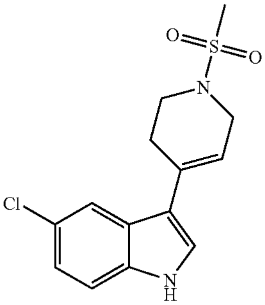
167
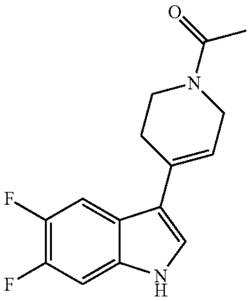
168
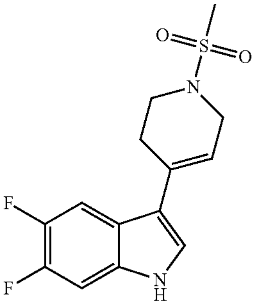
169
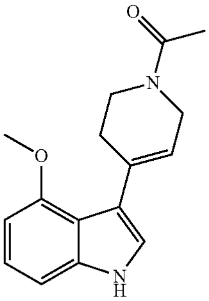
170
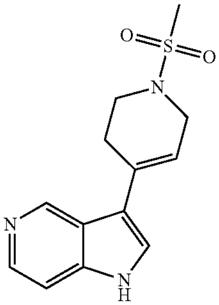

-continued
171
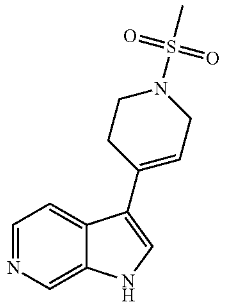
172
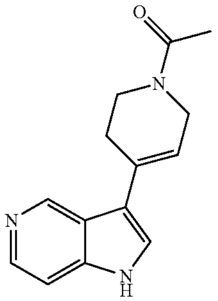
174
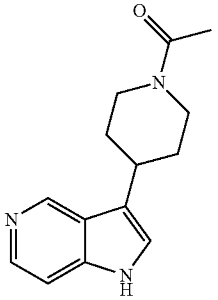
175
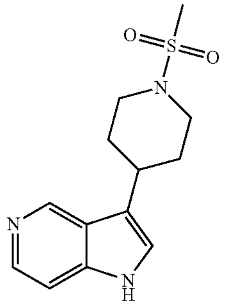
176
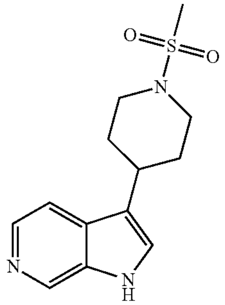
-continued
177
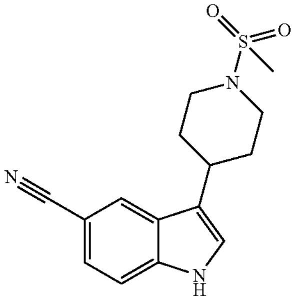
178
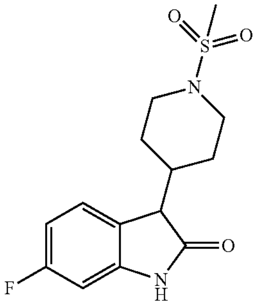
179
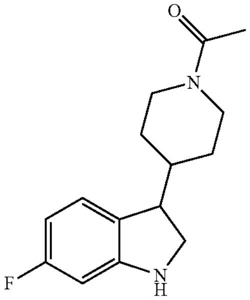
180
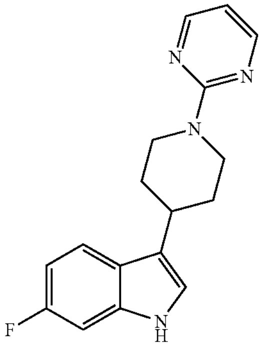
181
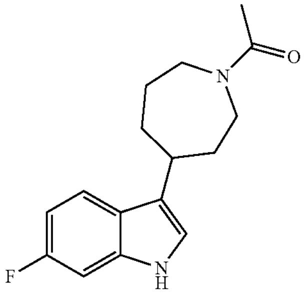

-continued
182
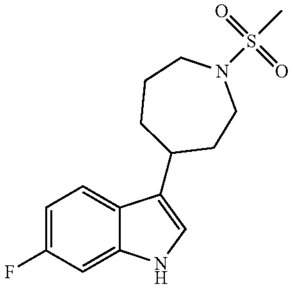
183
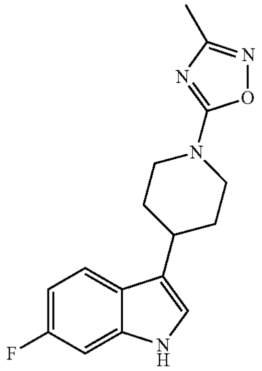
184
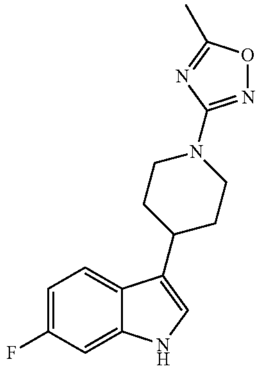
185
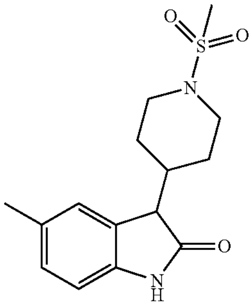
186
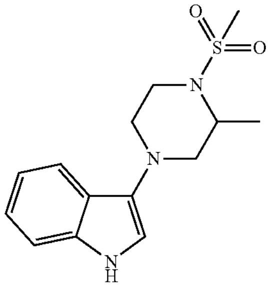
-continued
187
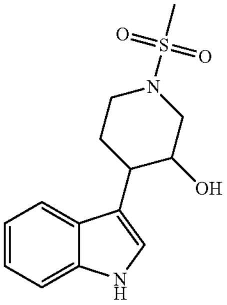
188
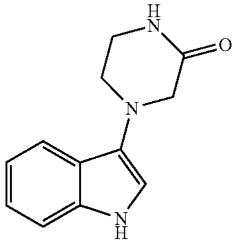
189
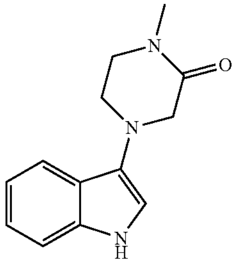
190
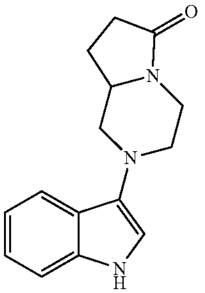
191
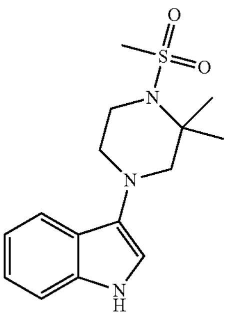

-continued
192
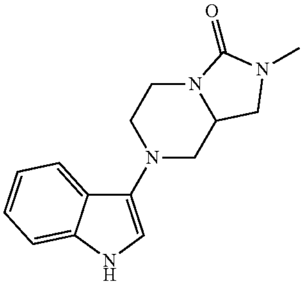
193
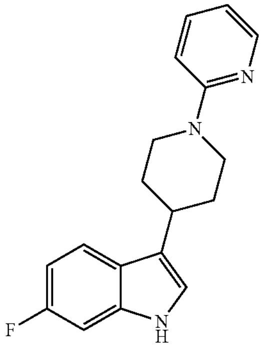
194
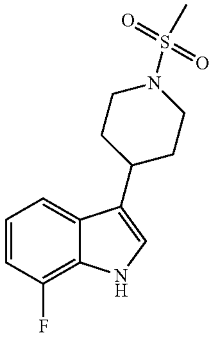
195
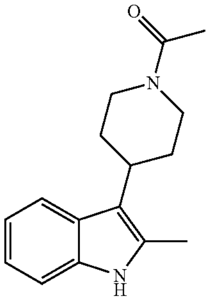
196
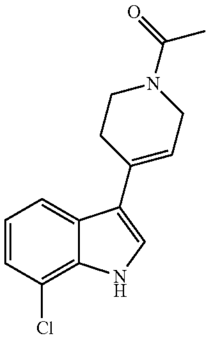
-continued
197
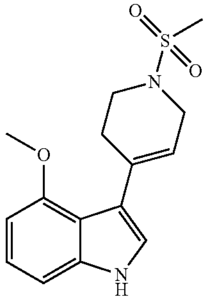
198
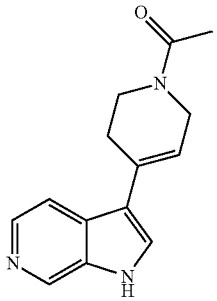
200
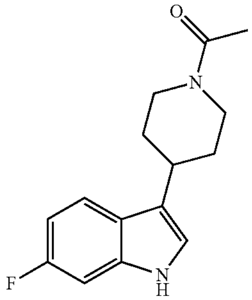
201
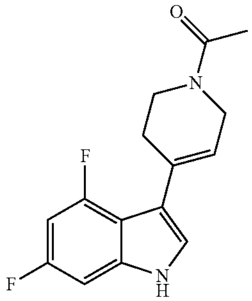
202
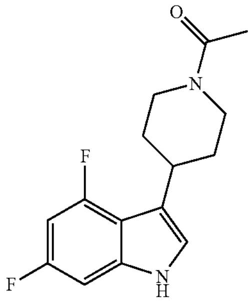

-continued
203
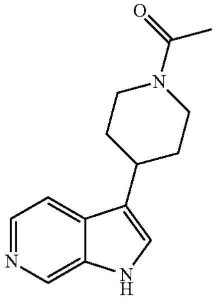
204
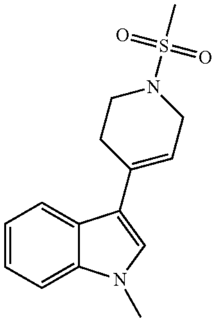
205
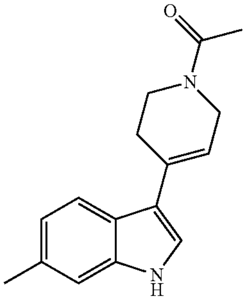
206
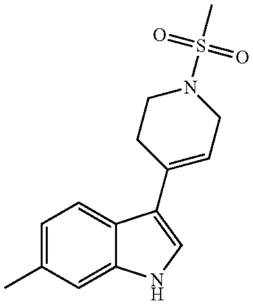
207
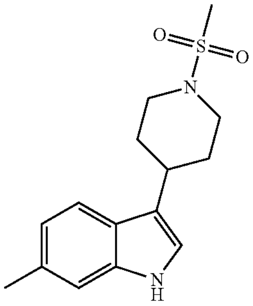
-continued
209
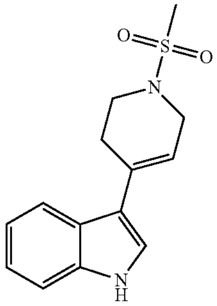
210
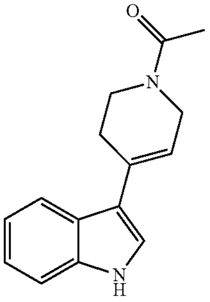
211
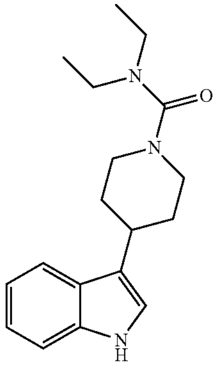
212
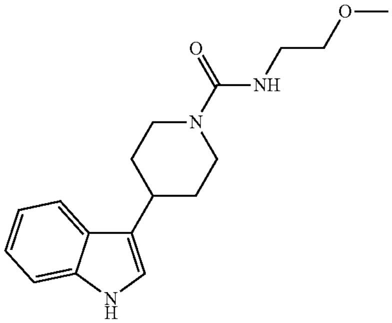
213
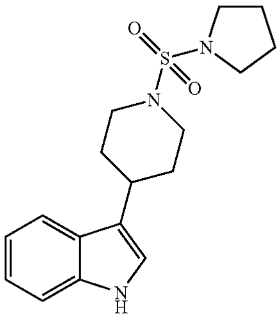

-continued
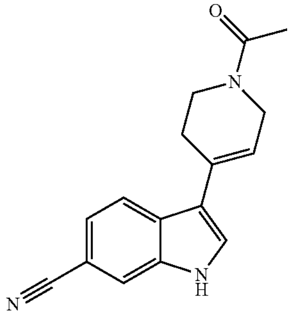
214
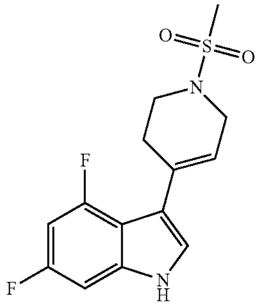
215
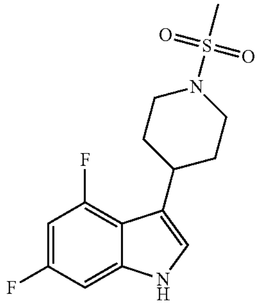
216
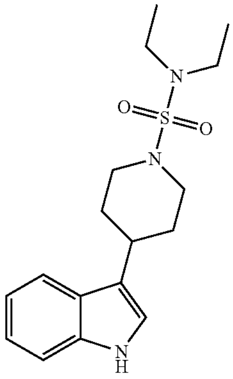
217
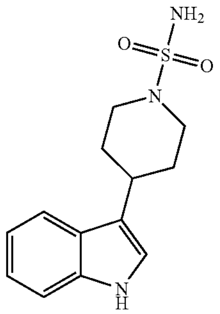
218
-continued
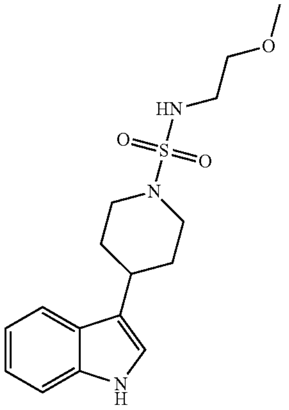
219
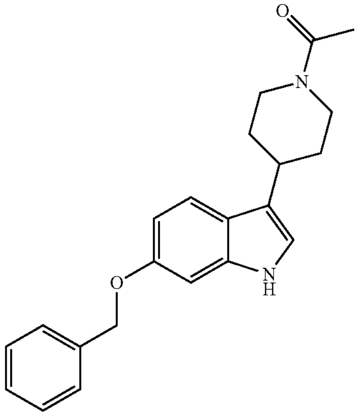
221
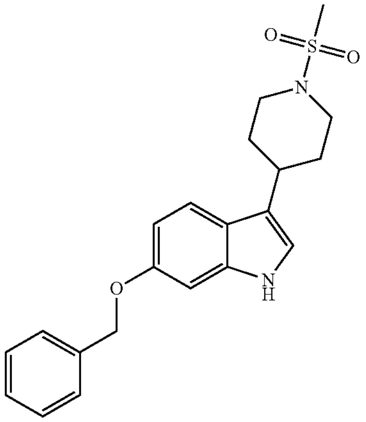
222
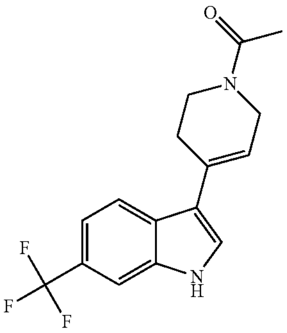
223

-continued
224
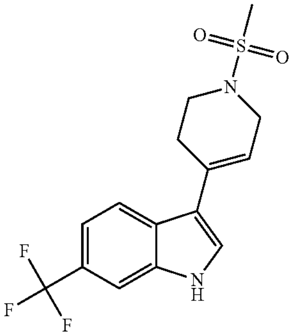
225
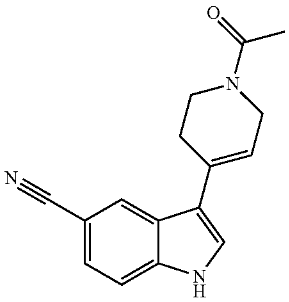
226
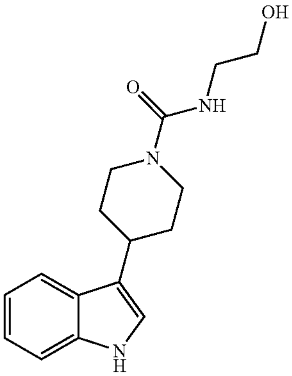
227
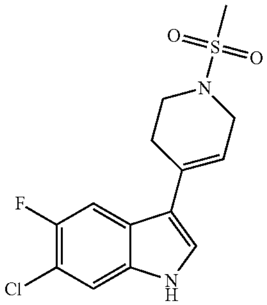
228
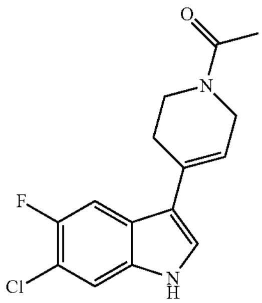
-continued
229
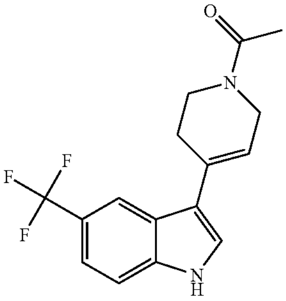
230
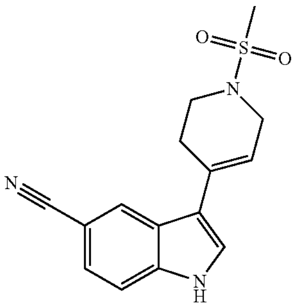
231
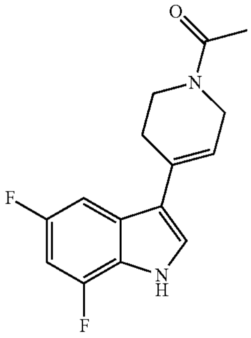
232
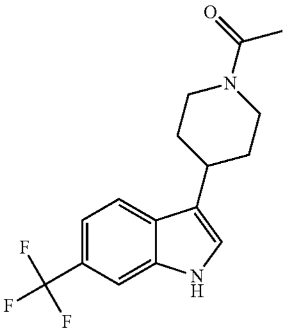
233
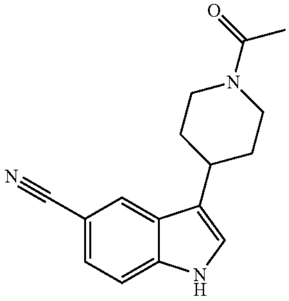

-continued
234
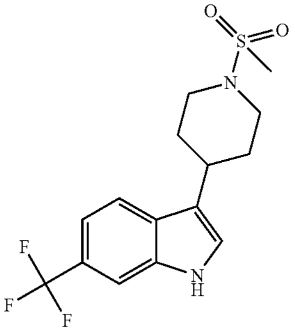
235
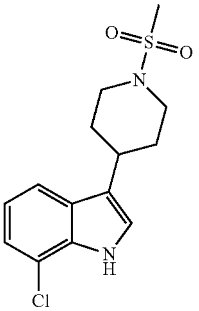
236
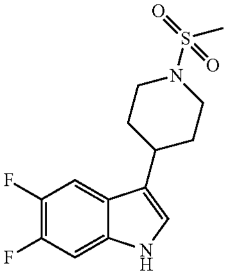
237
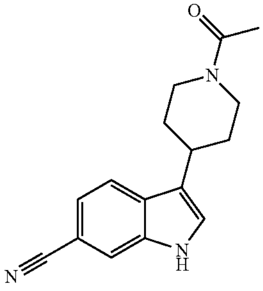
239
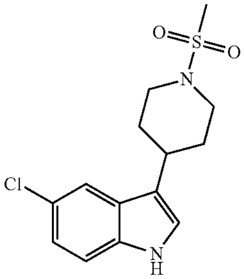
-continued
240
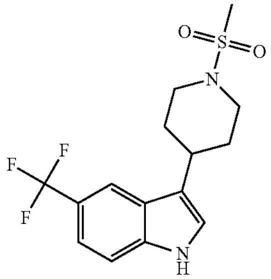
241
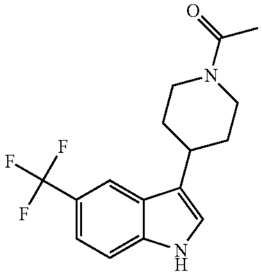
242
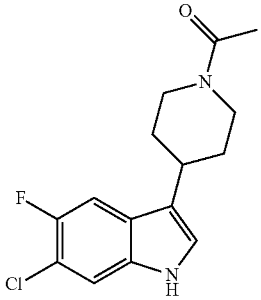
243
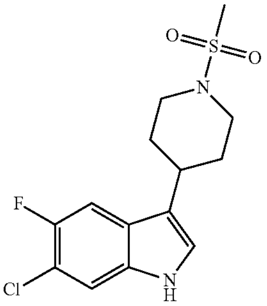
244
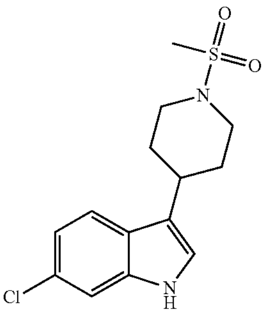

-continued
245
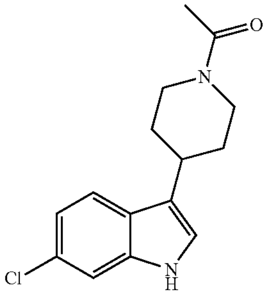
246
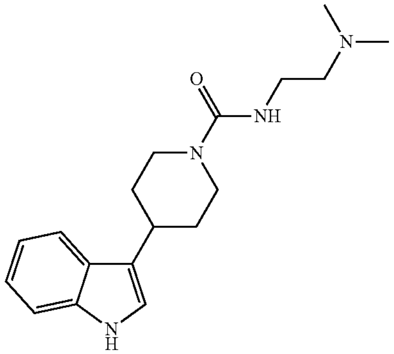
247
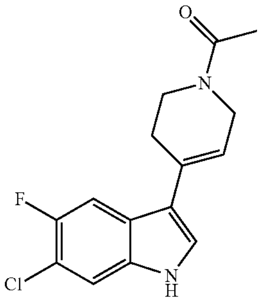
248
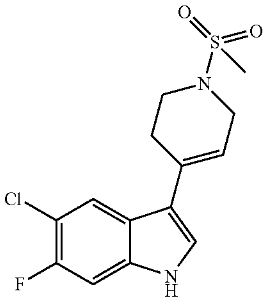
249
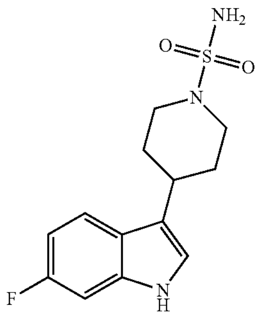
-continued
250
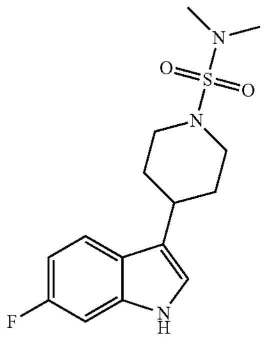
251
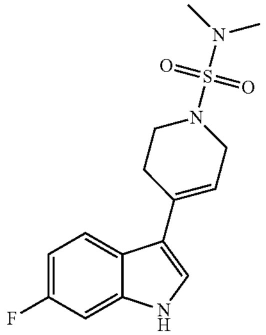
252
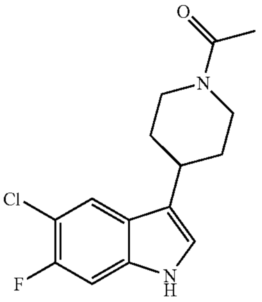
253
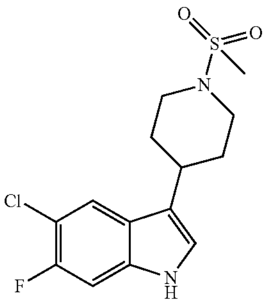
254
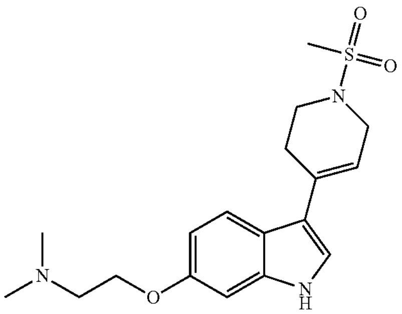

-continued
255
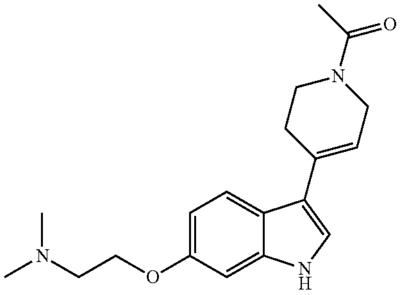
256
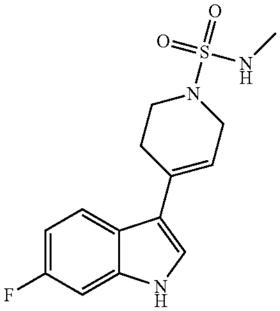
257
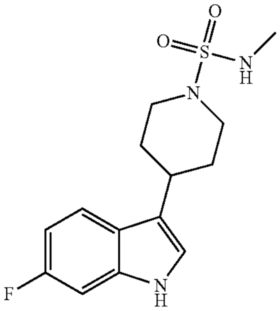
258
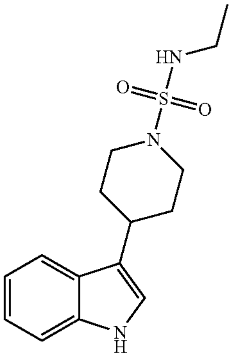
259
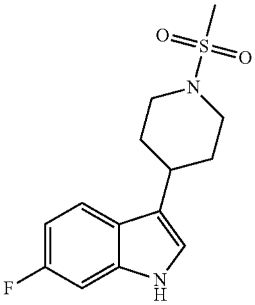
-continued
260
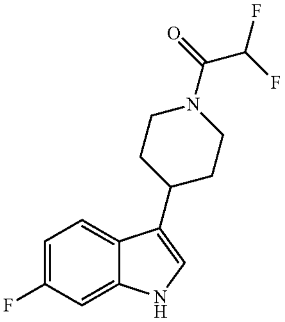
261
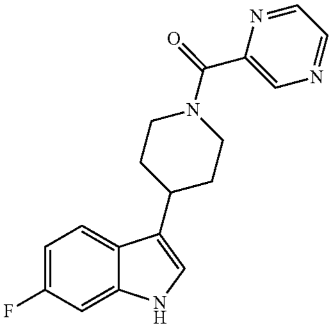
262
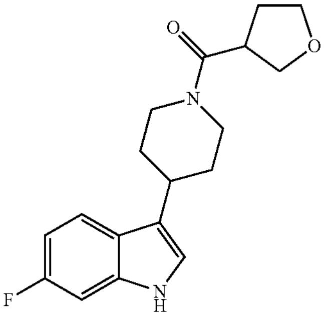
263
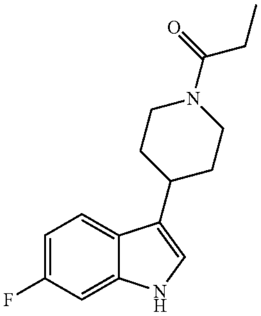

-continued
264
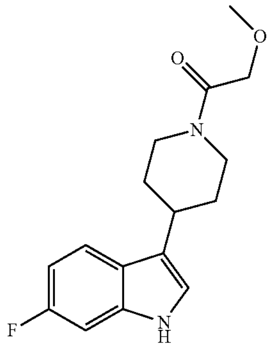
265
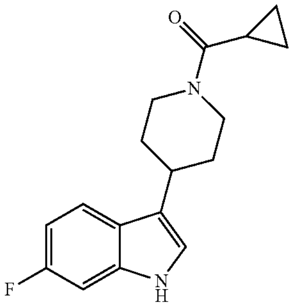
266
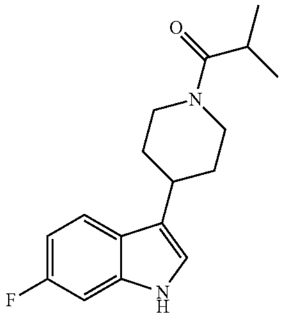
267
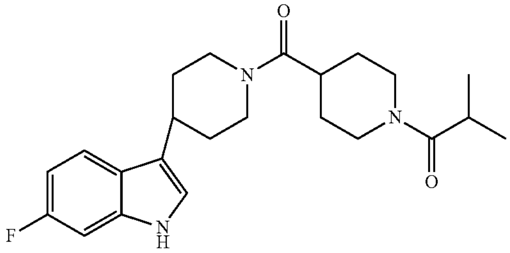
268
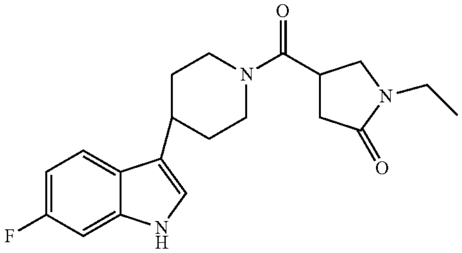
-continued
269
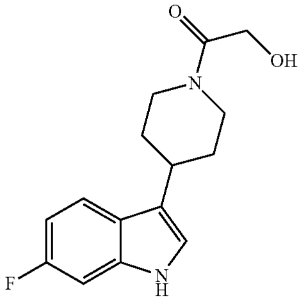
270
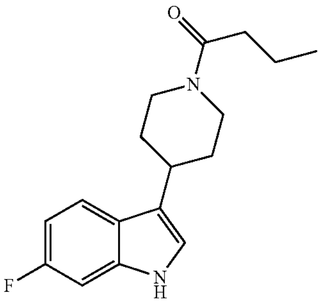
271
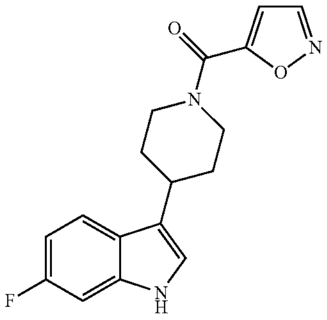
272
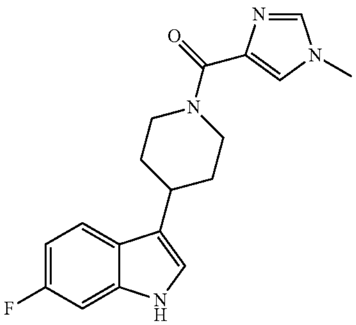
273
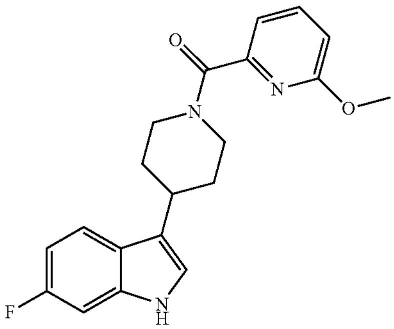

-continued
274
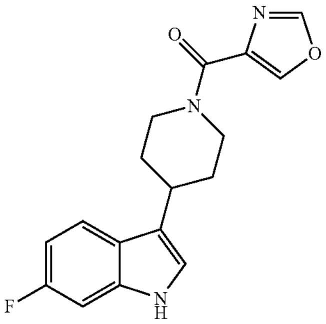
275
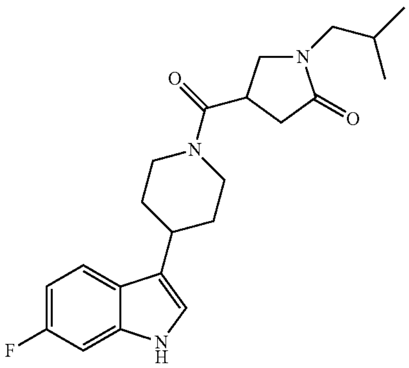
276
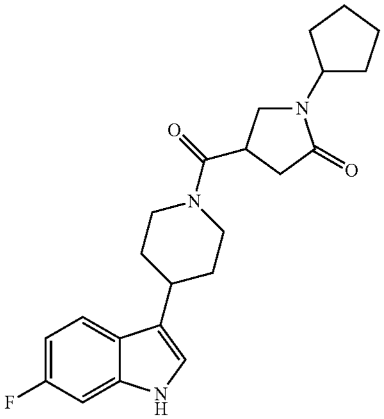
277
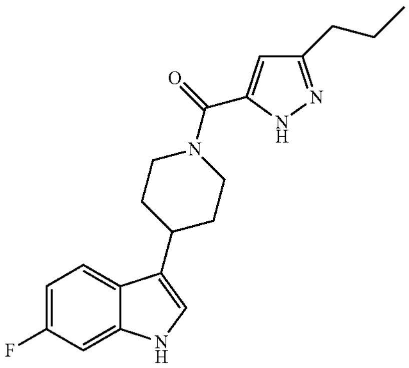
-continued
278
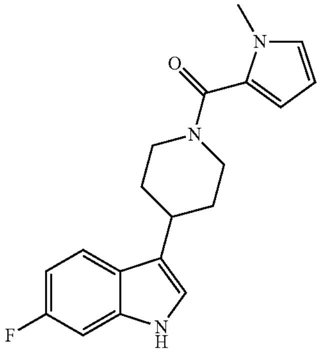
279
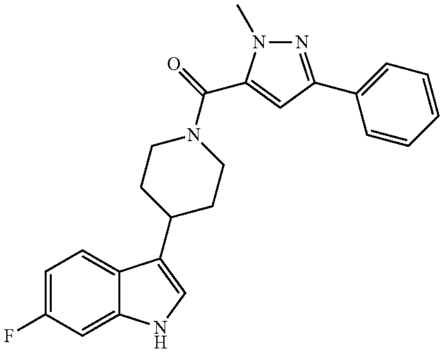
280
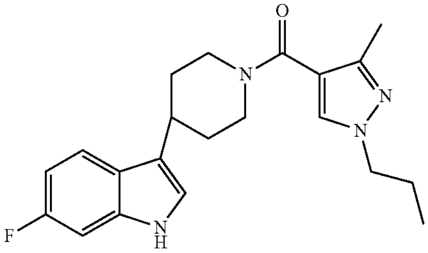
281
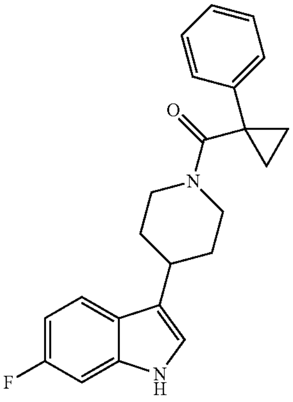

-continued
282
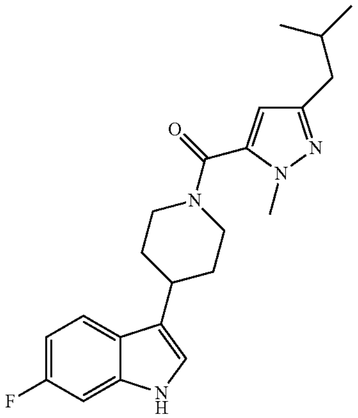
283
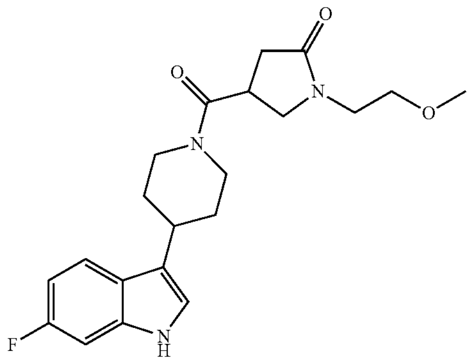
284
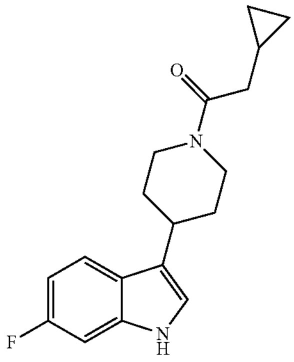
285
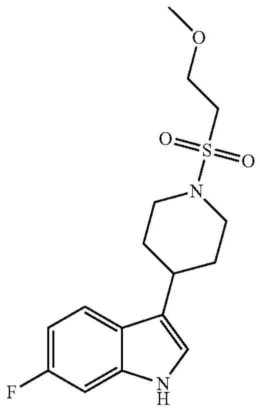
-continued
286
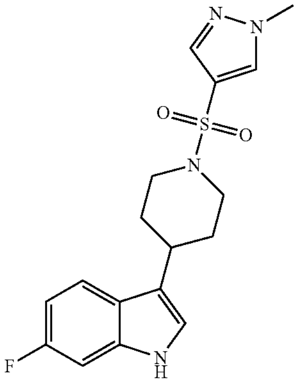
287
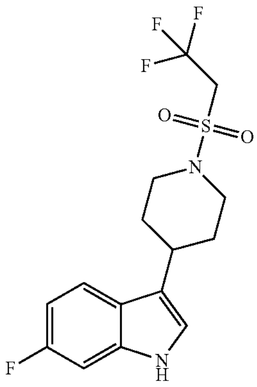
288
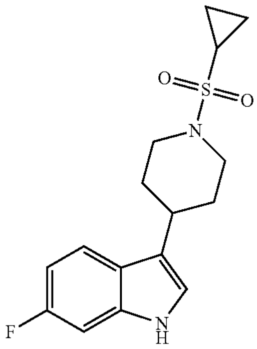
289
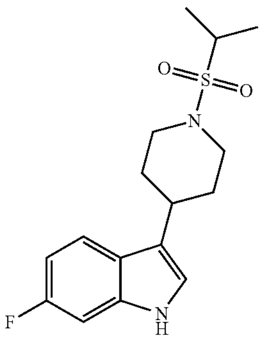

-continued
290
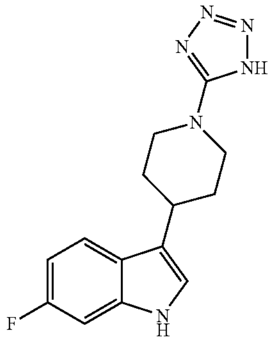
291
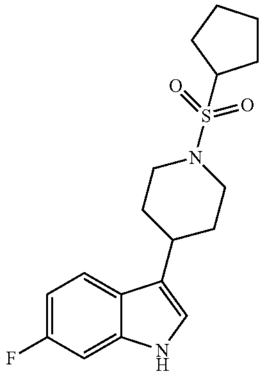
292
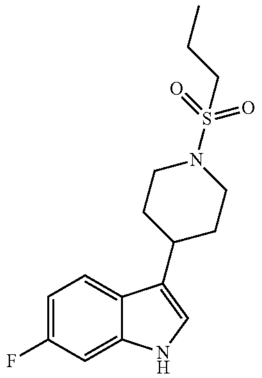
293
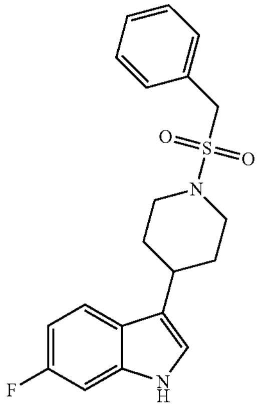
-continued
294
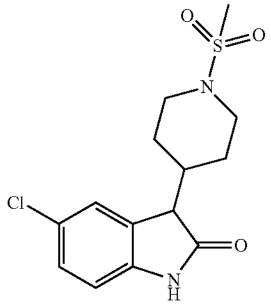
295
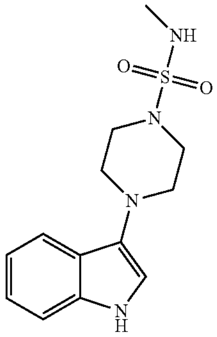
296
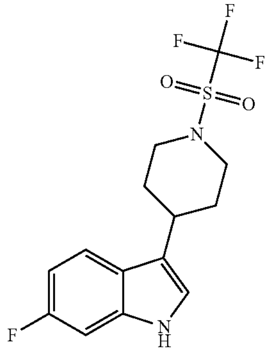
297
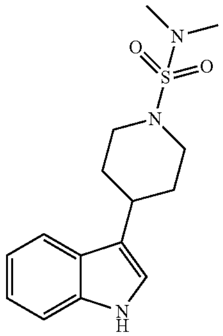
298
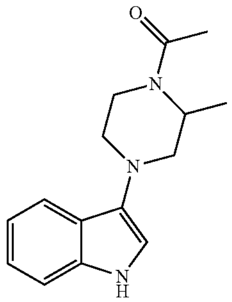

-continued
299
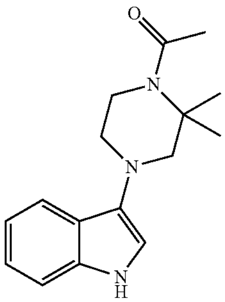
300
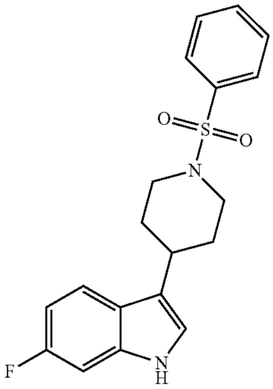
301
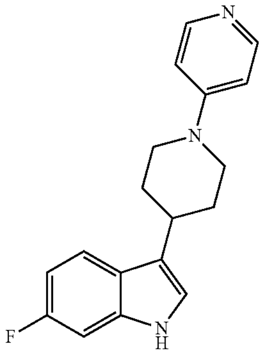
302
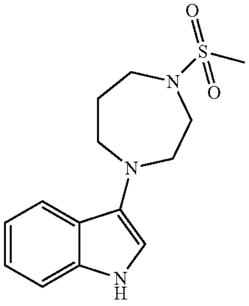
-continued
303
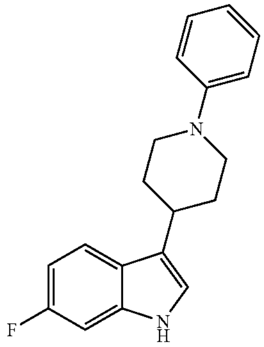
304
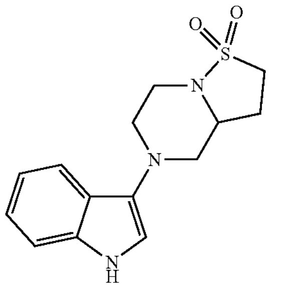
305
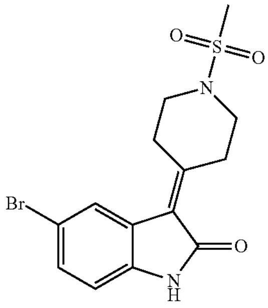
306
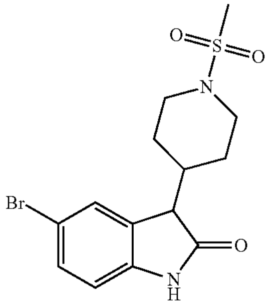
307
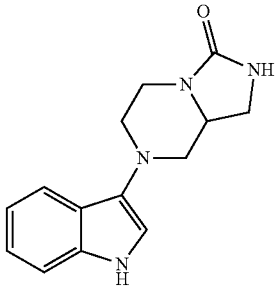

-continued
308
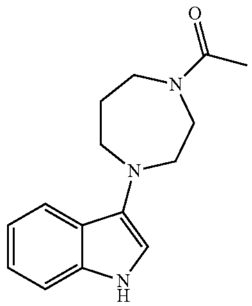
309
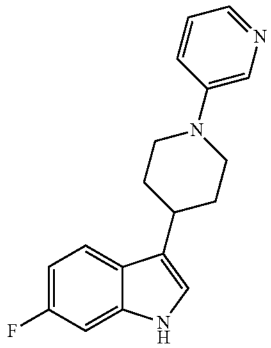
310
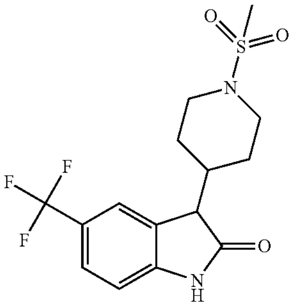
311
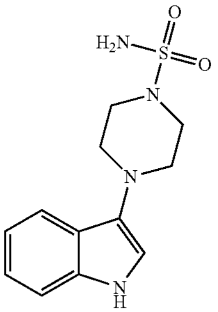
312
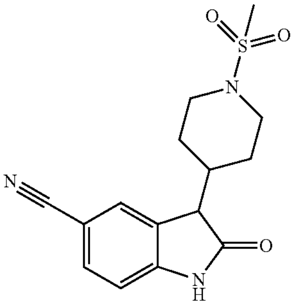
-continued
313
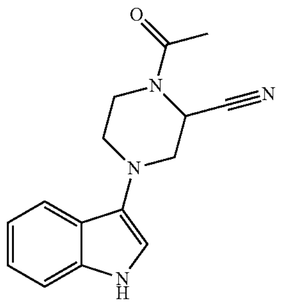
314
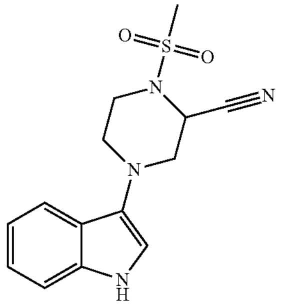
315
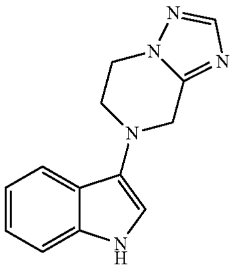
316
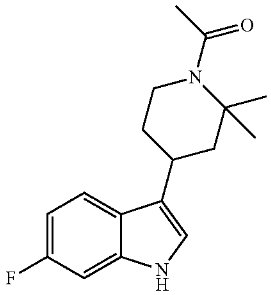
317
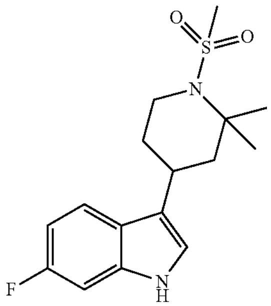

-continued

318

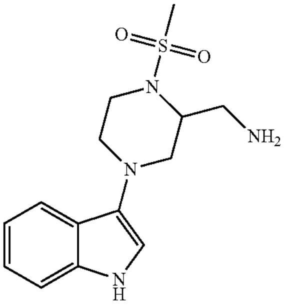

319

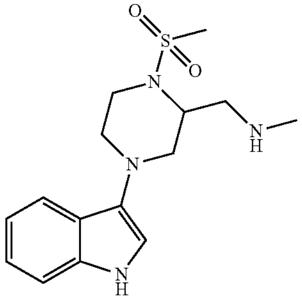

Typically, the above formulae (and all formulae herein) are shown in non-stereoisomeric form. For the avoidance of doubt, throughout the present disclosure a single formula is intended to represent all possible stereoisomers of a particular structure, including all possible isolated enantiomers corresponding to the formula, all possible mixtures of enantiomers corresponding to the formula, all possible mixtures of diastereomers corresponding to the formula, all possible mixtures of epimers corresponding to the formula and all possible racemic mixtures corresponding to the formula. In addition to this, the above formulae (and all formulae herein) are intended to represent all tautomeric forms equivalent to the corresponding formula.

The invention will now be described in more detail, by way of example only, with reference to the following specific embodiments.

EXAMPLES

Example 1—Methods of Synthesis

In order to demonstrate an exemplary method for synthesising the compounds of the present invention, the following synthesis was carried out.

2'

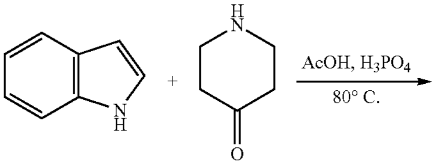

-continued

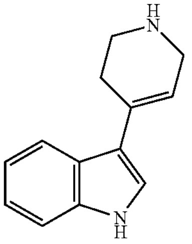

Indole (10 g) and piperidine hydrochloride (19.7 g) were dissolved in glacial acetic acid (100 ml) and $H_3PO_4$ (40 ml of 1 M solution in water). The solution was heated to 80° C. and stirred for 90 mins. The reaction mixture was then poured into ice-cooled $NH_4OH$ (500 ml) and extracted three times with EtOAc (200 ml) and twice with $CH_2Cl_2$ (200 ml). The organic extracts were combined and concentrated on a rotary evaporator to provide the crude product. Flash chromatography on silica gel, using 10-2-% NH3 saturated $CH_3OH$ in $CH_2Cl_2$ as the eluent, provided pure product 2'.

A further hydrogenation step produced further product 2 of the invention.

2

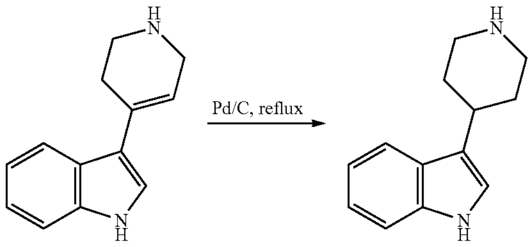

The product (1.1 g) was dissolved in $CH_3OH$ (100 ml) and treated with 10% Pd/C (250 mg) and ammonium formate (2.8 g). The mixture was refluxed overnight. The reaction mixture was then filtered through celite and concentrated to produce crude product 2, which was then purified.

The two reaction processes were repeated for different indole starting materials to produce each the following compounds:

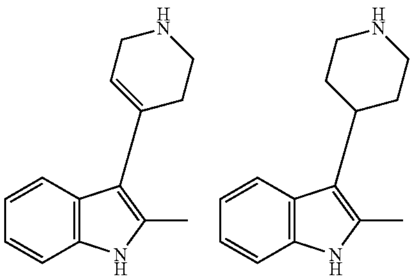

Example 2—Assays

Exemplary compounds of the invention were prepared, and tested to determine their effect as TDO and/or IDO inhibitors. Two different assays were employed: 1. a cell-based assay for detecting the effect of test compounds on kynurenine production in two different cancer cell types. This assay utilised cancer cells which expressed either TDO or IDO and as such was used as a means of testing compound activity at these two enzymes in a cell-based context. 2. a TDO and IDO biochemical coupled assay which utilised recombinantly produced and purified TDO and IDO enzymes in combination with the enzyme formamidase. This coupled enzyme system allowed conversion of N-formylkynurenine produced by TDO or IDO activity to kynurenine which was then quantified by fluorescence following addition of Erhlich's Reagent The protocols for these are set out below.

Cell Based Assay for Detection of Kynurenine Produced by TDO and/or IDO

A172 (human glioblastoma) and SKOV3 (human ovarian adenocarcinoma) cells were seeded in a 96 well plate at 30,000 or 40,000 cells per well respectively in phenol red-free RPMI supplemented with 10% FCS, 2 mM L-glutamine and 500 μM L-tryptophan. IDO expression was induced in the SKOV3 cells by the addition of 500 ng/ml IFN-γ. Cells were incubated at 37° C. with or without the addition of test compound. After 48 hours, the cells were removed by centrifugation and Erhlich's reagent was added to the supernatant. The Erhlich's reagent was incubated for 5 minutes before the absorbance was read at 490 nM.

TDO and IDO Biochemical Coupled Assay

Recombinant human IDO or TDO was incubated in 50 mM KPO4 (pH 7.0), 0.5 mM EGTA, 0.5 mM EDTA, 0.05% Triton™ X100, 20 mM ascorbate, 10 μM methylene blue, 500 U/ml catalase, 50 μg/ml KynB (kynurenine formamidase). TDO assays were carried out in the presence of 330 μM L-tryptophan, while IDO assays had the addition of 45 μM L-tryptophan. After incubation for 17 minutes at room temperature the reactions were stopped by the addition of Erhlich's reagent and incubated at room temperature for 5 minutes before the fluorescence was read (Ex475, Em530).

The pIC50 values for a variety of test compounds are shown in Table 1.

TABLE 1 pIC50 values for Kynurenine cell-based assays and IDO and TDO inhibition determined for test compounds

| Compound | A172 Kynurenine cell based assay pIC50 | SKOV3 Kynurenine cell based assay pIC50 | hIDO biocehm-ical assay pIC50 | hTDO biochem-ical assay pIC50 |
|---|---|---|---|---|
| 1 | ++ | + | +− | +− |
| 3 | ++ | +− | +− | ++ |
| 4 | + | +− | +− | + |
| 7 | +++ | + | +− | ++ |
| 8 | +− | + | +− | +− |
| 9 | + | + | +− | +− |
| 10 | + | +− | +− | +− |
| 11 | + | + | +− | +− |
| 13 | +− | ++ | +− | +− |
| 14 | + | +− | +− | +− |
| 15 | +− | + | +− | +− |
| 16 | + | +− | +− | +− |
| 17 | +− | + | +− | +− |
| 18 | ++ | + | +− | + |
| 19 | +− | + | +− | +− |
| 21 | + | + | +− | +− |
| 22 | +++ | +− | +− | + |
| 25 | +− | + | +− | +− |
| 26 | +− | + | +− | +− |
| 27 | + | + | +− | +− |
| 28 | +− | + | +− | +− |
| 29 | +− | + | +− | +− |
| 30 | +− | + | +− | +− |

TABLE 1-continued pIC50 values for Kynurenine cell-based assays and IDO and TDO inhibition determined for test compounds

| Compound | A172 Kynurenine cell based assay pIC50 | SKOV3 Kynurenine cell based assay pIC50 | hIDO biocehm-ical assay pIC50 | hTDO biochem-ical assay pIC50 |
|---|---|---|---|---|
| 31 | +− | + | +− | +− |
| 32 | +− | + | +− | +− |
| 34 | + | + | +− | +− |
| 35 | +− | + | +− | +− |
| 36 | + | ++ | +− | +− |
| 37 | +− | + | +− | +− |
| 38 | + | +− | +− | NT |
| 39 | + | + | +− | NT |
| 40 | + | +− | +− | NT |
| 41 | + | + | +− | NT |
| 43 | + | + | +− | NT |
| 45 | + | + | +− | NT |
| 46 | + | +− | +− | NT |
| 48 | + | + | +− | NT |
| 49 | ++ | + | +− | NT |
| 50 | + | + | +− | NT |
| 51 | + | + | +− | NT |
| 52 | +− | + | +− | NT |
| 53 | + | + | +− | NT |
| 54 | + | + | +− | +− |
| 55 | +− | ++ | +− | +− |
| 56 | +− | ++ | +− | +− |
| 57 | + | + | +− | +− |
| 58 | + | + | +− | +− |
| 59 | + | + | +− | +− |
| 66 | + | + | +− | +− |
| 67 | + | +− | +− | +− |
| 68 | + | +− | +− | ++ |
| 69 | ++ | +− | +− | + |
| 70 | +− | +− | +− | + |
| 71 | + | +− | +− | +− |
| 73 | + | +− | +− | +− |
| 74 | ++ | +− | +− | + |
| 75 | ++ | +− | +− | + |
| 76 | ++ | + | +− | ++ |
| 77 | + | + | +− | + |
| 78 | + | +− | +− | + |
| 79 | ++ | + | +− | ++ |
| 81 | +− | +− | +− | + |
| 82 | + | +− | +− | +− |
| 83 | + | +− | +− | +− |
| 84 | + | +− | +− | +− |
| 85 | ++ | ++ | +− | +− |
| 86 | ++ | + | +− | +++ |
| 88 | + | +− | +− | ++ |
| 89 | + | + | +− | ++ |
| 90 | ++ | + | +− | ++ |
| 91 | + | +− | +− | +− |
| 92 | ++ | + | +− | + |
| 93 | +− | +− | +− | + |
| 94 | + | +− | +− | + |
| 95 | + | +− | +− | +− |
| 98 | + | +− | +− | +− |
| 99 | +− | + | +− | +− |
| 100 | + | +− | +− | +− |
| 102 | +− | +− | +− | + |
| 103 | +++ | + | +− | ++ |
| 104 | +− | + | +− | + |
| 105 | +− | + | +− | + |
| 106 | + | +− | +− | +− |
| 107 | + | +− | +− | NT |
| 108 | + | +− | +− | NT |
| 155 | + | + | +− | NT |
| 156 | + | + | +− | NT |
| 157 | + | + | +− | NT |
| 158 | + | +− | +− | NT |
| 159 | ++ | +− | +− | NT |
| 160 | +− | + | +− | NT |
| 161 | +− | + | +− | NT |
| 162 | +++ | +− | +− | +++ |
| 163 | +++ | + | +− | ++ |
| 164 | +++ | +− | +− | +++ |

TABLE 1-continued pIC50 values for Kynurenine cell-based assays and IDO and TDO inhibition determined for test compounds

| Com-pound | A172 Kynurenine cell based assay pIC50 | SKOV3 Kynurenine cell based assay pIC50 | hIDO biocehm-ical assay pIC50 | hTDO biochem-ical assay pIC50 |
|---|---|---|---|---|
| 165 | ++ | + | +− | + |
| 166 | ++ | + | +− | + |
| 167 | ++ | + | +− | ++ |
| 168 | +++ | + | +− | ++ |
| 169 | + | + | +− | NT |
| 170 | ++ | + | +− | NT |
| 171 | ++ | +− | +− | NT |
| 172 | + | + | +− | NT |
| 173 | + | + | +− | +− |
| 174 | + | + | +− | +− |
| 175 | + | + | +− | +− |
| 176 | + | + | +− | +− |
| 177 | + | + | NT | NT |
| 178 | +− | ++ | +− | +− |
| 179 | + | +− | +− | +− |
| 180 | + | ++ | +− | NT |
| 181 | ++ | +− | +− | NT |
| 182 | ++ | + | +− | NT |
| 183 | ++ | + | +− | NT |
| 184 | ++ | + | +− | NT |
| 185 | +− | ++ | +− | NT |
| 186 | ++ | +− | +− | NT |
| 187 | + | +− | NT | NT |
| 188 | ++ | +− | NT | NT |
| 189 | + | +− | +− | NT |
| 190 | ++ | +− | NT | NT |
| 191 | ++ | +− | NT | NT |
| 192 | + | +− | NT | NT |
| 193 | ++ | ++ | NT | NT |
| 194 | + | +/− | +/− | +/− |
| 195 | +/− | + | +/− | +/− |
| 196 | + | + | +/− | +/− |
| 197 | +/− | +/− | +/− | + |
| 198 | +/− | +/− | +/− | + |
| 199 | +/− | +/− | +/− | + |
| 200 | ++ | +/− | NT | NT |
| 201 | ++ | +/− | NT | NT |
| 202 | + | +/− | NT | NT |
| 203 | + | + | +/− | +/− |
| 204 | +/− | +/− | +/− | + |
| 205 | + | +/− | +/− | + |
| 206 | ++ | +/− | +/− | +/− |
| 207 | + | + | NT | NT |
| 208 | + | + | NT | +/− |
| 209 | ++ | +/− | +/− | ++ |
| 210 | ++ | +/− | NT | ++ |
| 211 | +/− | + | +/− | +/− |
| 212 | + | +/− | +/− | +/− |
| 213 | + | + | NT | NT |
| 214 | +/− | + | NT | NT |
| 215 | ++ | + | NT | NT |
| 216 | + | +/− | NT | NT |
| 217 | + | + | NT | NT |
| 218 | ++ | +/− | NT | + |
| 219 | + | +/− | NT | NT |
| 220 | + | +/− | NT | NT |
| 221 | + | + | NT | NT |
| 222 | +/− | + | NT | NT |
| 223 | + | + | NT | NT |
| 224 | + | +/− | NT | NT |
| 225 | + | + | NT | NT |
| 226 | + | +/− | NT | NT |
| 227 | ++ | +/− | NT | + |
| 228 | ++ | + | NT | NT |
| 229 | + | + | NT | NT |
| 230 | ++ | +/− | NT | NT |
| 231 | + | + | NT | NT |
| 232 | + | + | NT | NT |
| 233 | + | + | NT | NT |
| 234 | + | + | NT | NT |
| 235 | +/− | + | NT | NT |
| 236 | ++ | + | NT | + |

TABLE 1-continued pIC50 values for Kynurenine cell-based assays and IDO and TDO inhibition determined for test compounds

| Com-pound | A172 Kynurenine cell based assay pIC50 | SKOV3 Kynurenine cell based assay pIC50 | hIDO biocehm-ical assay pIC50 | hTDO biochem-ical assay pIC50 |
|---|---|---|---|---|
| 237 | + | +/− | NT | NT |
| 238 | + | + | NT | NT |
| 239 | ++ | ++ | +/− | NT |
| 240 | + | ++ | +/− | +/− |
| 241 | + | + | +/− | +/− |
| 242 | +/− | + | +/− | +/− |
| 243 | + | + | +/− | +/− |
| 244 | + | + | +/− | +/− |
| 245 | ++ | + | +/− | +/− |
| 246 | + | +/− | +/− | +/− |
| 247 | + | +/− | NT | NT |
| 248 | ++ | + | NT | NT |
| 249 | ++ | +/− | +/− | + |
| 250 | ++ | + | +/− | +/− |
| 251 | +++ | + | +/− | + |
| 252 | + | + | +/− | +/− |
| 253 | + | + | +/− | +/− |
| 254 | + | + | NT | NT |
| 255 | ++ | + | NT | NT |
| 256 | ++ | + | +/− | + |
| 257 | ++ | + | +/− | + |
| 258 | + | +/− | NT | NT |
| 259 | + | + | +/− | +/− |
| 260 | ++ | +/− | +/− | + |
| 261 | + | +/− | +/− | +/− |
| 262 | + | +/− | +/− | +/− |
| 263 | ++ | ++ | +/− | + |
| 264 | ++ | +/− | +/− | +/− |
| 265 | ++ | + | +/− | + |
| 266 | + | +/− | +/− | +/− |
| 267 | + | +/− | +/− | +/− |
| 268 | + | +/− | +/− | +/− |
| 269 | ++ | + | +/− | + |
| 270 | ++ | + | +/− | +/− |
| 271 | + | +/− | +/− | +/− |
| 272 | + | +/− | +/− | +/− |
| 273 | + | + | +/− | +/− |
| 274 | + | +/− | +/− | +/− |
| 275 | + | +/− | +/− | +/− |
| 276 | + | + | +/− | +/− |
| 277 | + | + | +/− | +/− |
| 278 | + | ++ | + | +/− |
| 279 | + | + | +/− | +/− |
| 280 | ++ | + | +/− | +/− |
| 281 | + | + | +/− | +/− |
| 282 | + | + | +/− | +/− |
| 283 | + | + | +/− | +/− |
| 284 | + | + | +/− | +/− |
| 285 | ++ | + | +/− | + |
| 286 | ++ | +/− | +/− | + |
| 287 | ++ | +/− | +/− | +/− |
| 288 | ++ | + | +/− | + |
| 289 | ++ | + | +/− | +/− |
| 290 | + | +/− | +/− | NT |
| 291 | ++ | + | +/− | +/− |
| 292 | ++ | + | +/− | + |
| 293 | ++ | + | +/− | +/− |
| 294 | +/− | ++ | +/− | NT |
| 295 | ++ | +/− | NT | + |
| 296 | ++ | + | NT | +/− |
| 297 | ++ | +/− | +/− | +/− |
| 298 | ++ | +/− | +/− | +/− |
| 299 | ++ | + | +/− | +/− |
| 300 | ++ | +/− | +/− | NT |
| 301 | + | + | +/− | NT |
| 302 | +/− | + | +/− | NT |
| 303 | ++ | +/− | +/− | +/− |
| 304 | ++ | +/− | +/− | + |
| 305 | +/− | + | +/− | NT |
| 306 | +/− | ++ | +/− | NT |
| 307 | ++ | +/− | +/− | +/− |
| 308 | +/− | + | +/− | + |

TABLE 1-continued pIC50 values for Kynurenine cell-based assays and IDO and TDO inhibition determined for test compounds

| Compound | A172 Kynurenine cell based assay pIC50 | SKOV3 Kynurenine cell based assay pIC50 | hIDO biocehm-ical assay pIC50 | hTDO biochem-ical assay pIC50 |
|---|---|---|---|---|
| 309 | ++ | +/− | NT | +/− |
| 310 | +/− | + | +/− | NT |
| 311 | ++ | +/− | NT | + |
| 312 | +/− | + | NT | NT |
| 313 | + | +/− | NT | NT |
| 314 | ++ | +/− | NT | NT |
| 315 | + | +/− | +/− | +/− |
| 316 | ++ | + | +/− | +/− |
| 317 | ++ | + | +/− | +/− |
| 318 | ++ | +/− | +/− | +/− |
| 319 | ++ | +/− | NT | + |

Key:
+++ = $pIC_{50}$ ≥6.00
++ = $pIC_{50}$ 5.00-5.99
+ = $pIC_{50}$ 4.00-4.99
+− = $pIC_{50}$ <4.00
NT = not tested The Table shows that a large number of the test compounds show strong TDO and IDO inhibitory function.

The invention claimed is:

1. A compound having the following formula, or a pharmaceutically acceptable salt thereof:

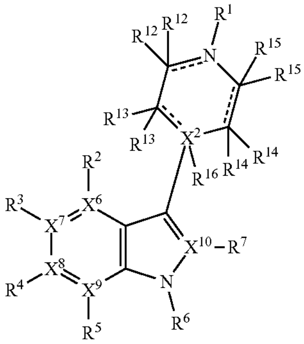

wherein each of $X^2$ $X^6$, $X^7$, $X^8$ and $X^9$ is independently selected from C and N;

$X^{10}$ is C;

each bond having a dotted line is independently a double bond or a single bond, provided that the valencies at each atom are maintained;

$R^1$ is

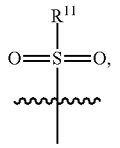

wherein $R^{11}$ is selected from the group consisting of:

a substituted or unsubstituted linear or branched $C_1$-$C_6$ alkyl group selected from Me, Et, Pr, i-Pr, n-Bu, i-Bu, t-Bu, pentyl and hexyl;

a substituted or unsubstituted linear or branched $C_1$-$C_6$ alkyl-aryl group selected from —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph;

a substituted or unsubstituted linear or branched $C_1$-$C_6$ halogenated alkyl group selected from —$CH_2F$, —$CH_2Cl$, —$CH_2Br$, —$CH_2I$, —$CF_3$, —$CCl_3$—$CBr_3$, —$CI_3$, —$CH_2CF_3$, —$CH_2CCl_3$, —$CH_2CBr_3$, and —$CH_2CI_3$;

an —$NH_2$ group or a substituted or unsubstituted linear or branched primary, secondary or tertiary $C_1$-$C_6$ amine group selected from —NMeH, —NMe, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt;

a substituted or unsubstituted amino-aryl group selected from —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$I_2$-Ph, —NH-2,(3,4,5 or 6)$Me_2$-Ph, —NH-2,(3,4,5 or 6)$Et_2$-Ph, —NH-2,(3,4,5, or 6)$Pr_2$-Ph, and —NH-2,(3,4,5 or 6)$Bu_2$-Ph;

a substituted or unsubstituted cyclic amine or amido group selected from pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl;

a substituted or unsubstituted cyclic $C_3$-$C_8$ alkyl group selected from cyclopropyl, cyclobutyl, cyclopentyl, cyclohexyl, cycloheptyl and cyclooctyl;

an —OH group or a substituted or unsubstituted linear or branched $C_1$-$C_6$ alcohol group selected from —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, and —$CH_2CH_2CH_2CH_2CH_2CH_2OH$;

a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-I-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-($NH_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-$(NO_2)$-Ph-, 3-$(NO_2)$-Ph-, 4-$(NO_2)$-Ph-, 2-$(NH_2)$-Ph-, 3-$(NH_2)$-Ph-, 4-$(NH_2)$-Ph-, 2-MeO-Ph-, 3-MeO-Ph-, 4-MeO-Ph-, 2-$(NH_2$—CO-Ph-, —CO)-Ph-, 3-$(NH_2$—CO)-Ph-, 4-$(NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-;

a substituted or unsubstituted saturated or unsaturated heterocyclic group selected from pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl; and a substituted or unsubstituted saturated heterocyclic group selected from piperidin-2-yl, piperidin-3-yl, piperidin-4-yl, tetrahydrofuran-2-yl, tetrahydrofuran-3-yl, tetrahydropyran-2-yl, tetrahydropyran-3-yl, and tetrahydropyran-4-yl;

each $R^{12}$, $R^{13}$, $R^{14}$, and $R^{15}$ is independently selected from H and a substituted or unsubstituted organic group, provided that the number of such R groups present is such that the valency of the ring carbon atoms is maintained;

$R^{16}$ is selected from H and a substituted or unsubstituted organic group, provided that the number of $R^{16}$ groups present is such that the valency of $X^2$ is maintained;

each $R^2$, $R^3$, $R^4$, and $R^5$ is independently selected from H and a substituted or unsubstituted organic group, provided that the number of such R groups present is such that the valencies of $X^6$, $X^7$, $X^8$, and $X^9$ are maintained;

$R^6$ is selected from H and $C_1$-$C_6$ alkyl; and $R^7$ is selected from H and $C_1$-$C_6$ alkyl.

2. The compound of claim 1 having any one of the following formulae:

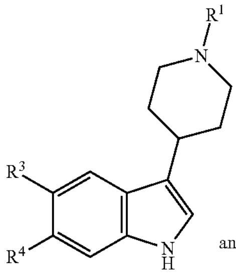

and

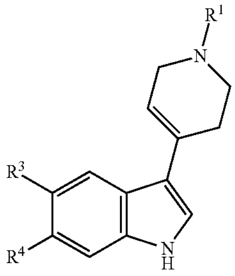

, wherein $R^1$ is selected from the group consisting of:

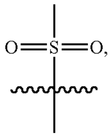

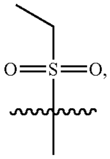

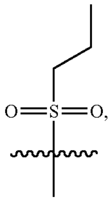

-continued

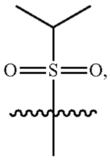

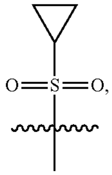

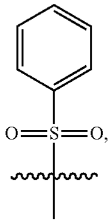

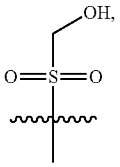

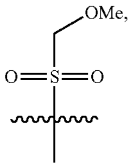

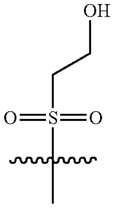

,

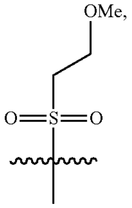

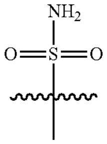

,

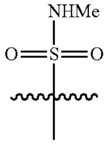

,

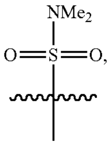

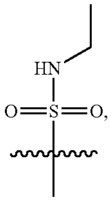

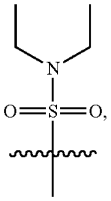

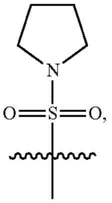

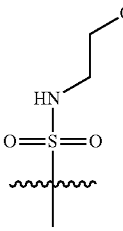

,

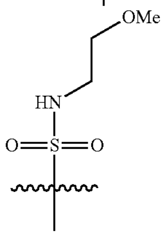

, and

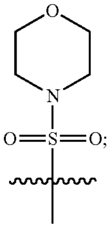

and wherein $R^3$ and $R^4$ are independently selected from the group consisting of:

—H, —F, —Cl, -Me, —$CF_3$, —CN, —OMe, —OPh, —$OCH_2Ph$, —$OCH_2NH_2$, —$OCH_2NHMe$, —$OCH_2NMe_2$, —$OCH_2CH_2NH_2$, —$OCH_2CH_2NHMe$, and —$OCH_2CH_2NMe_2$.

3. The compound of claim 2, wherein R is

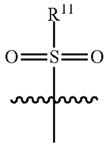

wherein each occurrence of $R^{11}$ is independently selected from the group consisting of:

a substituted or unsubstituted linear or branched $C_1$-$C_6$ alkyl group selected from Me, Et, Pr, i-Pr, n-Bu, i-Bu, t-Bu, pentyl and hexyl;

a substituted or unsubstituted linear or branched $C_1$-$C_6$ alkyl-aryl group selected from —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph;

a substituted or unsubstituted linear or branched $C_1$-$C_6$ halogenated alkyl group selected from —$CH_2$F, —$CH_2$Cl, —$CH_2$Br, —$CH_2$I, —$CF_3$, —$CCl_3$—$CBr_3$, —$CI_3$, —$CH_2CF_3$, —$CH_2CCl_3$, —$CH_2CBr_3$, and —$CH_2CI_3$;

an —$NH_2$ group or a substituted or unsubstituted linear or branched primary secondary or tertiary $C_1$-$C_6$ amine group selected from —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt;

a substituted or unsubstituted cyclic $C_3$-$C_8$ alkyl group selected from cyclopropyl, cyclobutyl, cyclopentyl, cyclohexyl, cycloheptyl and cyclooctyl;

a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-$(NO_2)$-Ph-, 3-$(NO_2)$-Ph-, 4-$(NO_2)$-Ph-, 2-$(NH_2)$-Ph-, 3-$(NH_2)$-Ph-, 4-$(NH_2)$-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-; and a substituted or unsubstituted saturated or unsaturated heterocyclic group selected from pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl), and a substituted or unsubstituted saturated heterocyclic group selected from piperidin-2-yl, piperidin-3-yl, piperidin-4-yl, tetrahydrofuran-2-yl, and tetrahydrofuran-3-yl, tetrahydropyran-2-yl, tetrahydropyran-3-yl, and tetrahydropyran-4-yl;

one of $R^3$ and $R^4$ is H while the other is selected from —H, —F, —Cl, -Me, —$CF_3$, -MeO and —CN;

$R^6$ is selected from H and Me;

$R^7$ is selected from H and Me; and $R^{12}$, $R^{13}$, $R^{14}$, $R^{15}$, $R^{16}$, $R^2$, and $R^5$ are each H; or alternatively, $R^{13}$, $R^{14}$ and $R^{16}$ are each H, and one or both of $R^{12}$ and $R^{15}$ are a $C_1$-$C_3$ alkyl group optionally substituted with an —OH group or an —$NH_2$ group.

4. The compound of claim 2, wherein $R^1$ is:

a sulphonyl group selected from $SO_2$Me, —$SO_2$Et, —$SO_2$Pr, —$SO_2$iPr, —$SO_2$Ph, —$SO_2$-(2,3 or 4)-F-Ph, —$SO_2$-cyclopropyl, and —$SO_2CH_2CH_2OCH_3$.

5. The compound of claim 4, wherein, where present, $R^3$ and $R^4$ are independently selected from:

H,

F, —Cl,

-Me,

—$CF_3$,

—OMe,

—CN,

—$OCH_2$Ph,

—$OCH_2CH_2NMe_2$, and

=O.

6. The compound of claim 5, wherein, where present, one of $R^3$ and $R^4$ is H while the other is selected from —H, —F, —Cl, -Me, —$CF_3$, -MeO and —CN.

7. The compound of claim 1, wherein:

$R^6$ is H;

$R^{12}$, $R^{13}$, $R^{14}$, $R^{15}$, $R^{16}$, $R^2$, and $R^5$ are each H; or alternatively, $R^{13}$, $R^{14}$, and $R^{16}$ are each H, and one or both of $R^{12}$ and $R^{15}$ are a $C_1$-$C_3$ alkyl group optionally substituted with an —OH group or an —$NH_2$ group, and where present, one of $R^3$ and $R^4$ is H while the other is selected from —H, —F, —Cl, -Me, —$CF_3$, -MeO and —CN.

8. The compound of claim 1, which compound comprises a formula selected from one of the following:

3

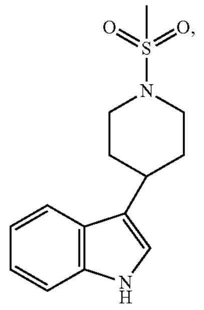

4

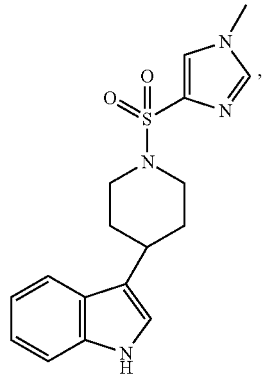

-continued
7
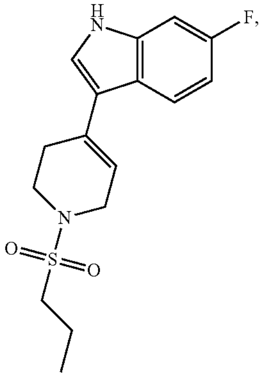
,
9
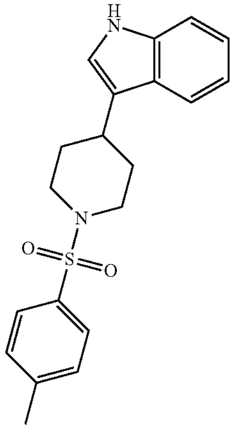
12
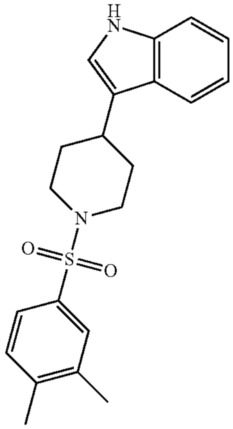
,
13
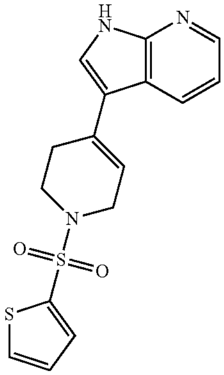
,
-continued
14
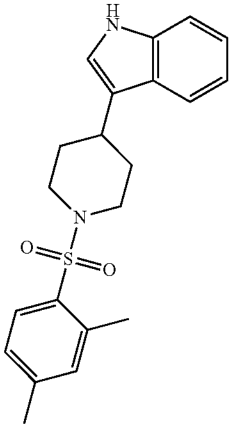
,
18
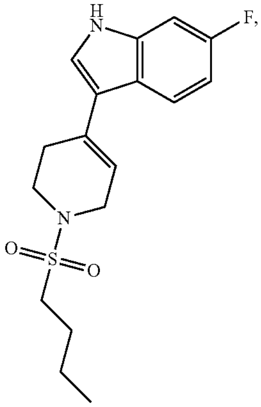
,
20
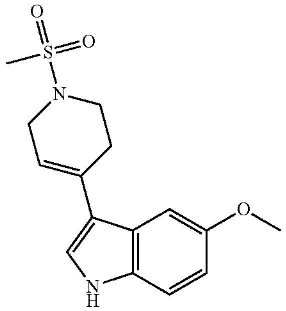
,
21
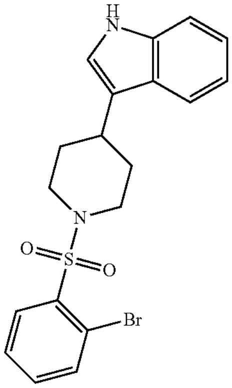
, 22
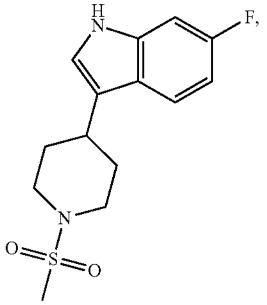
23
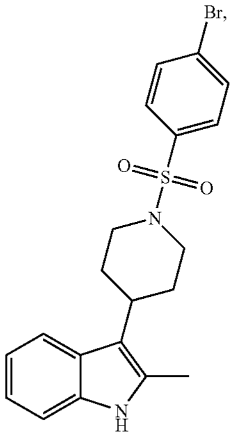
24
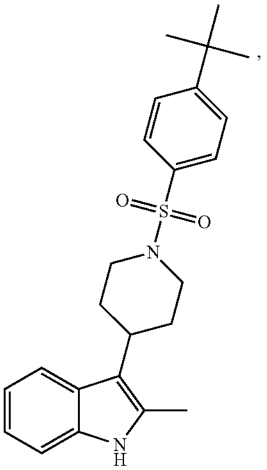
25
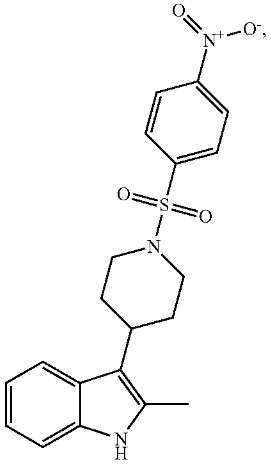
26
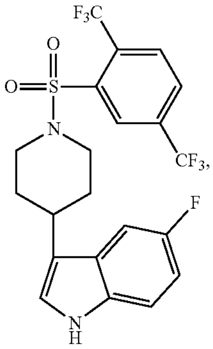
27
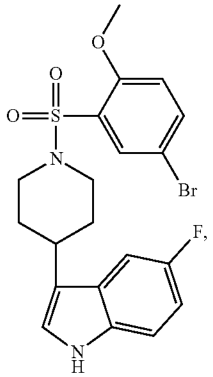
29
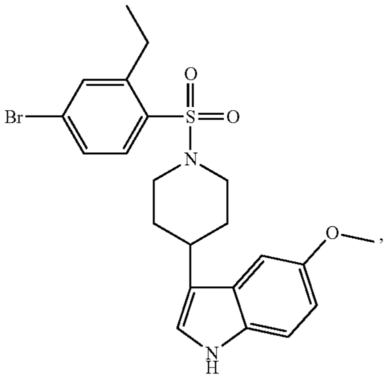

-continued
30
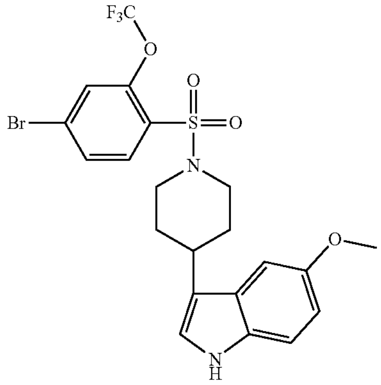
,
31
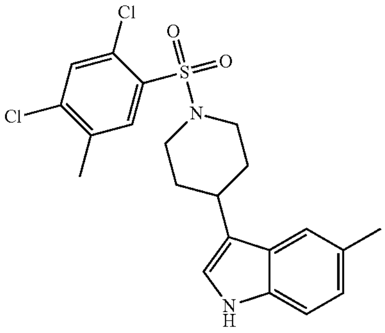
,
32
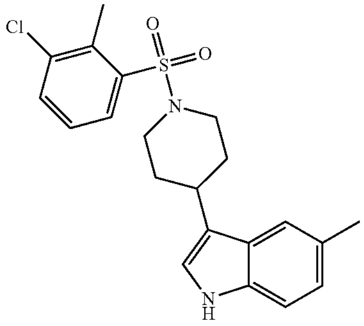
,
33
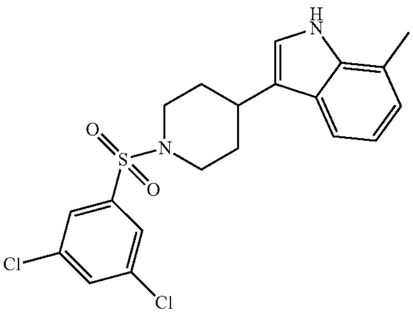
,
-continued
34
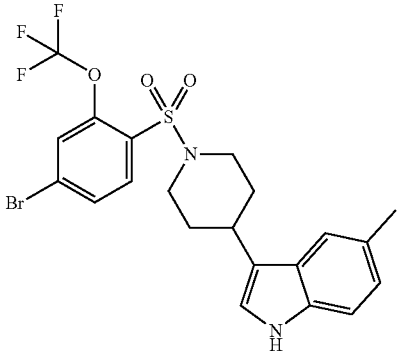
,
35
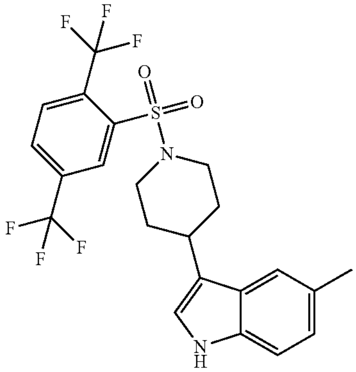
,
36
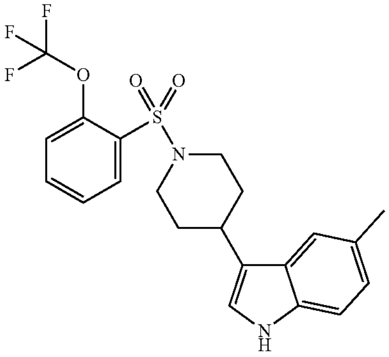
,
37
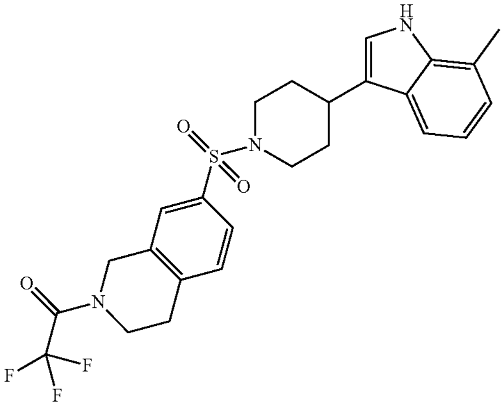
, -continued
38
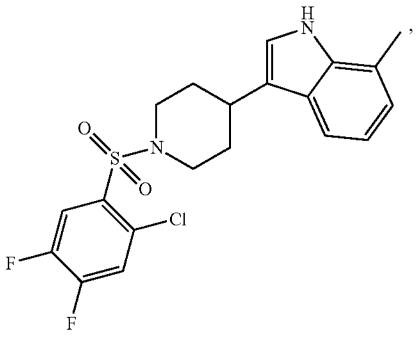
39
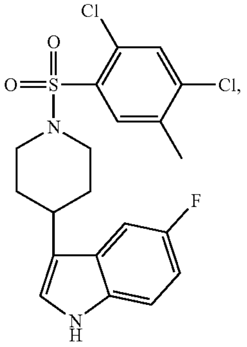
40
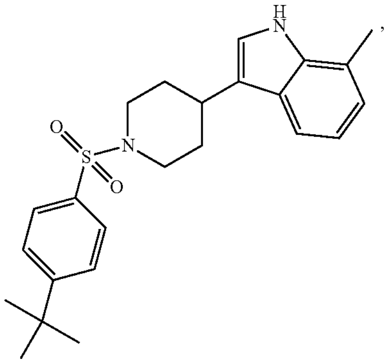
42
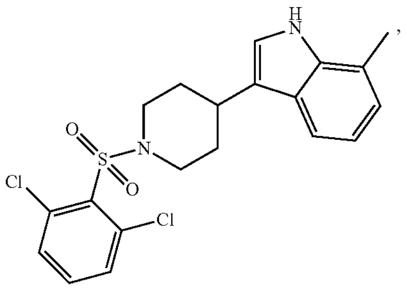
-continued
43
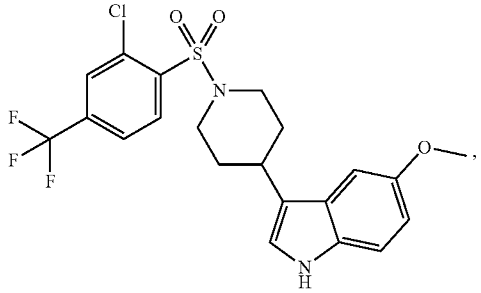
44
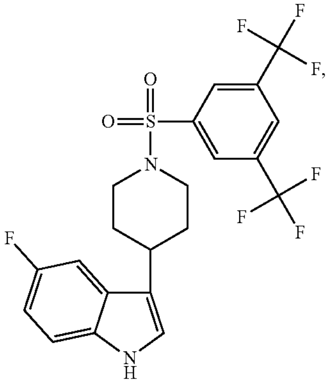
45
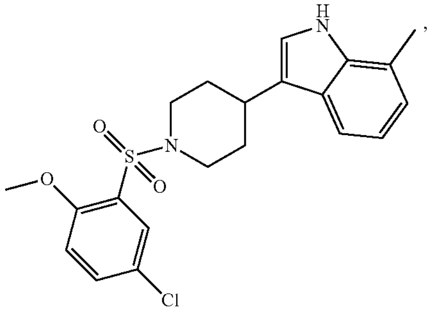
46
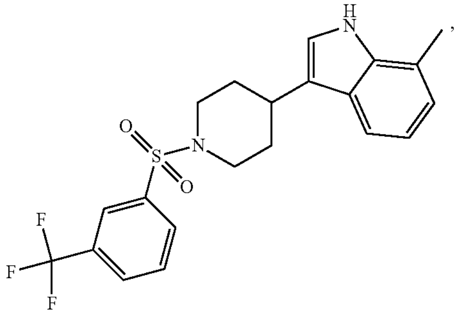
47
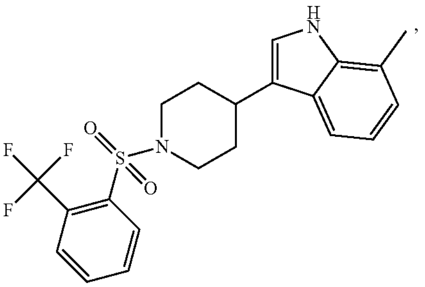

-continued
48
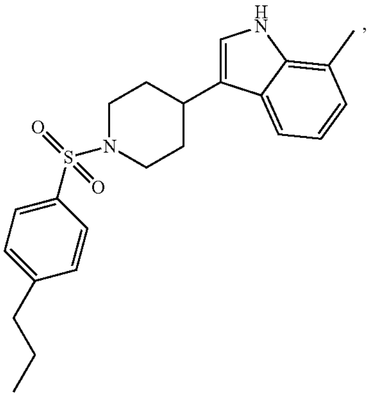
49
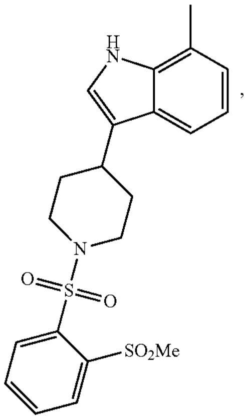
50
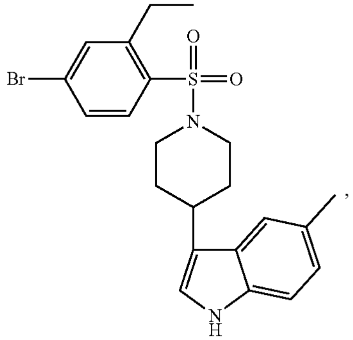
51
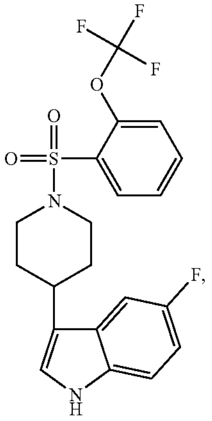
-continued
52
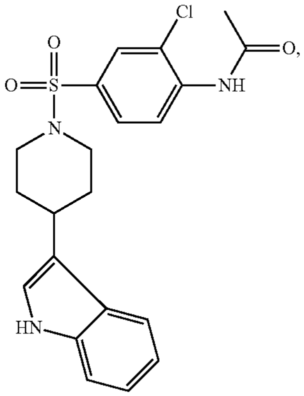
53
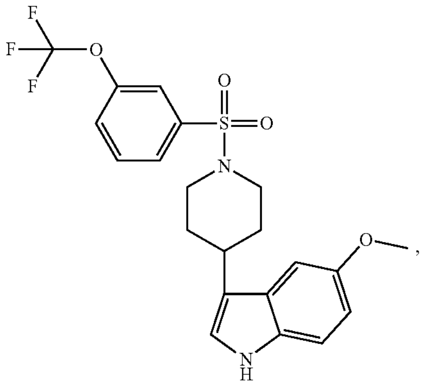
55
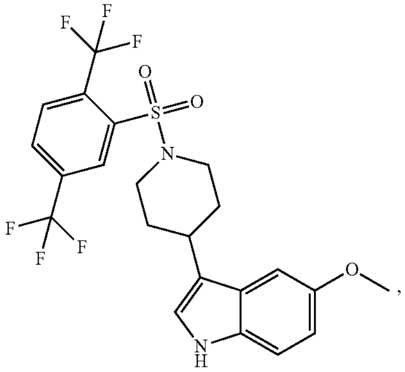
56
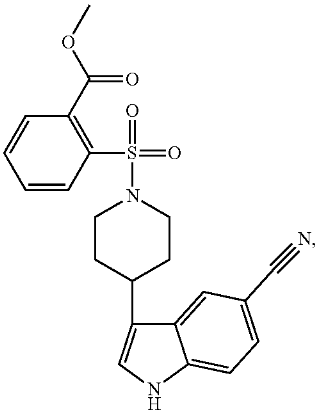

-continued
57
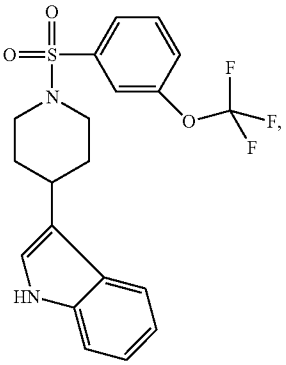
58
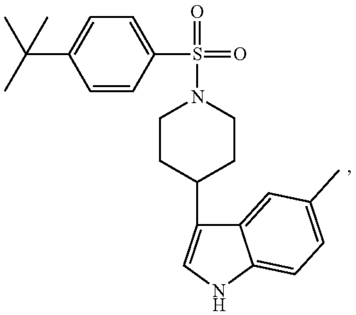
60
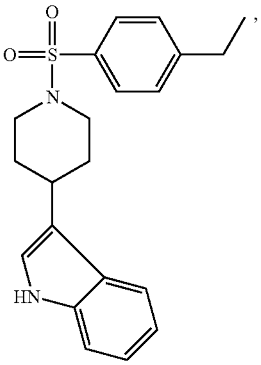
61
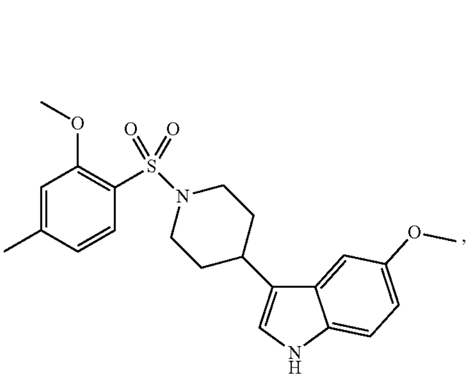
-continued
62
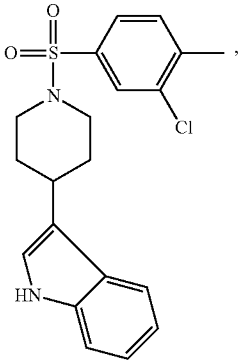
63
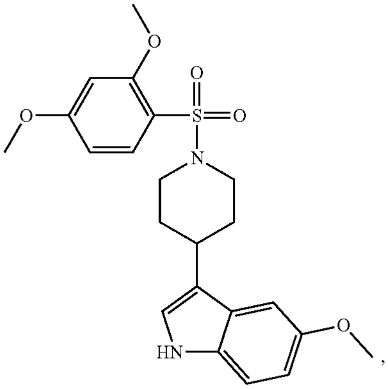
64
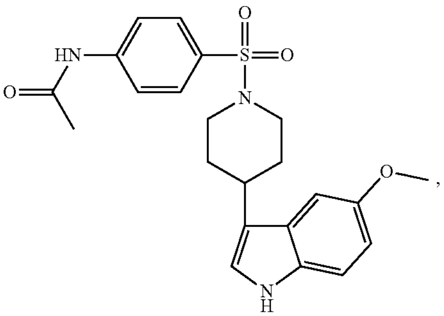
69
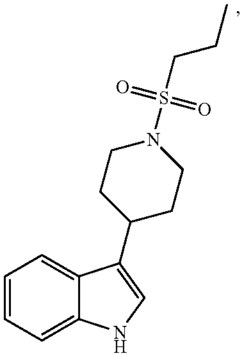

-continued
72
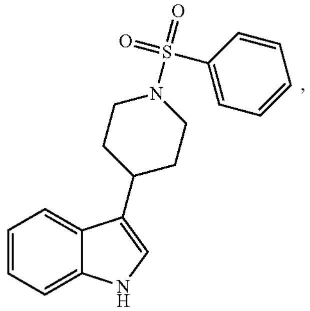
73
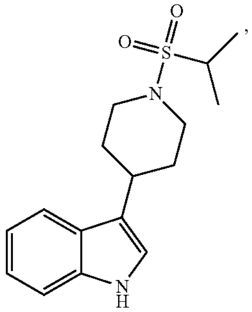
74
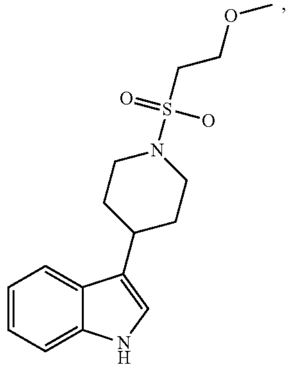
75
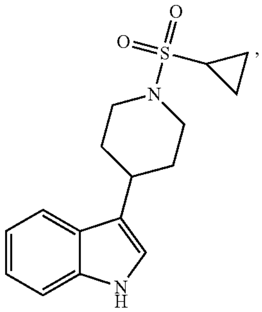
76
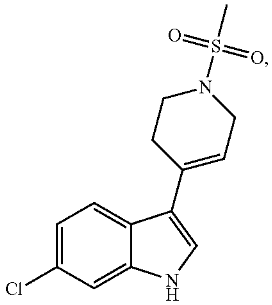
-continued
78
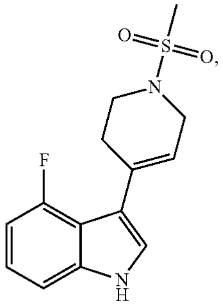
85
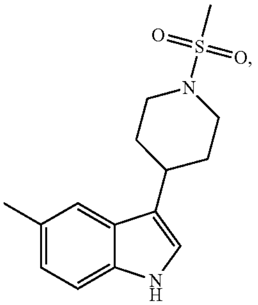
90
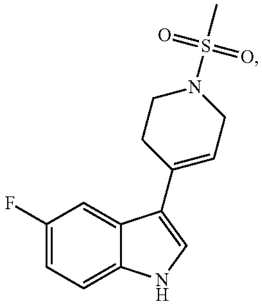
92
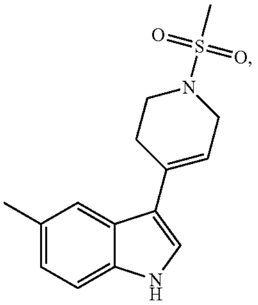
93
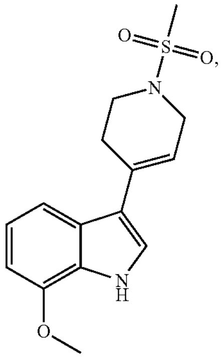

-continued
95
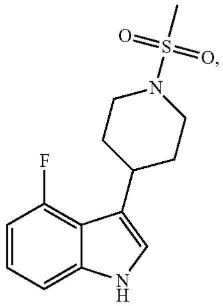
96
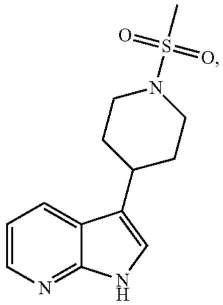
97
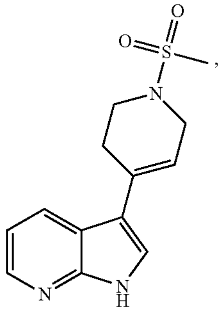
100
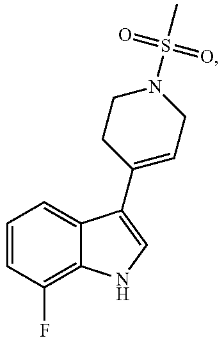
101
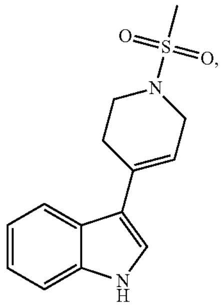
-continued
103
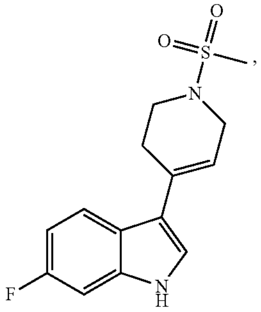
108
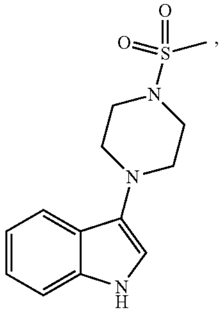
110
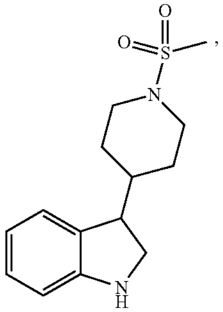
112
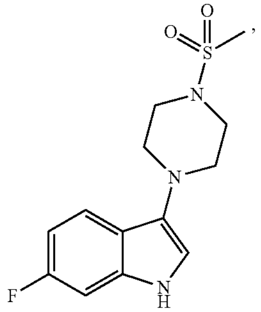
128
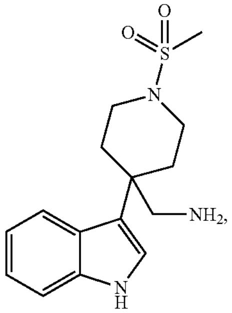

-continued
130
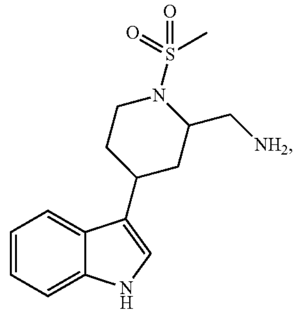
132
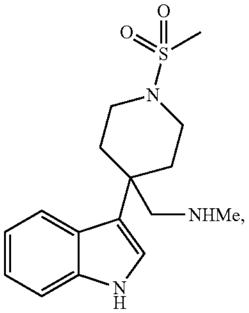
134
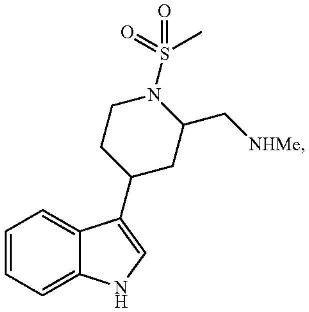
136
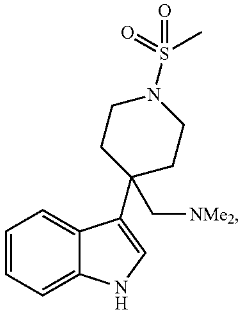
138
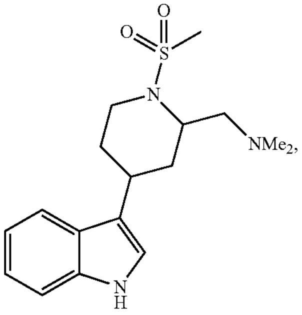
-continued
140
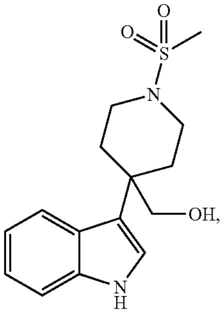
142
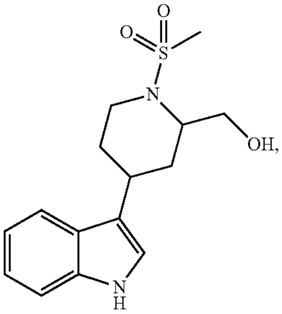
159
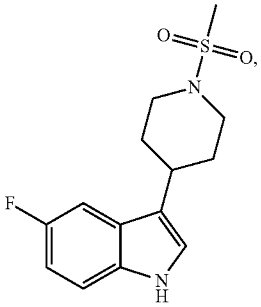
160
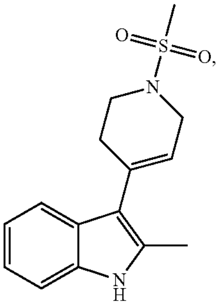
161
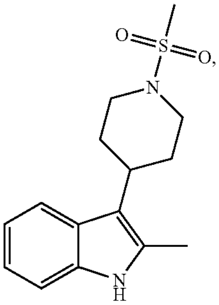

-continued
162
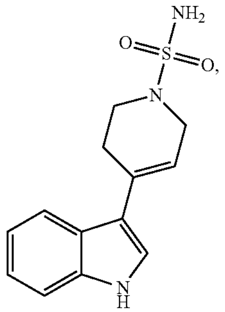
164
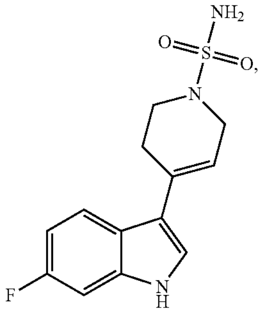
166
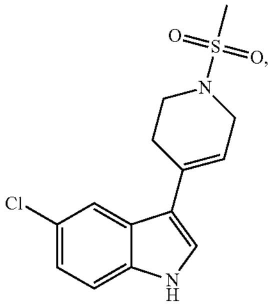
168
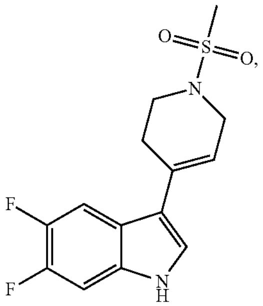
170
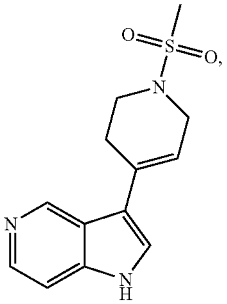
-continued
171
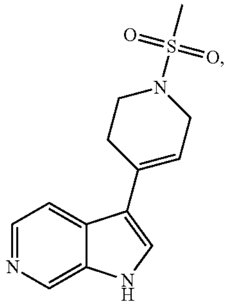
175
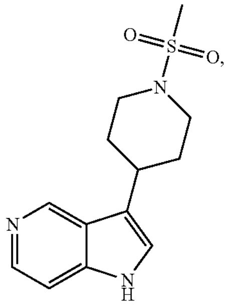
176
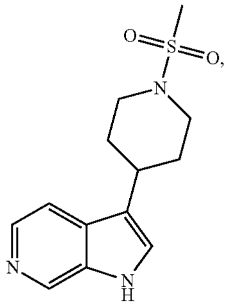
177
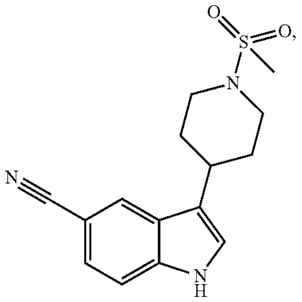
178
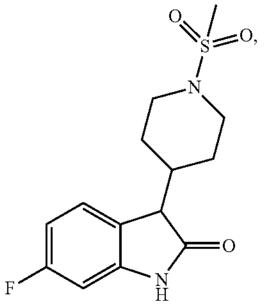

-continued
186
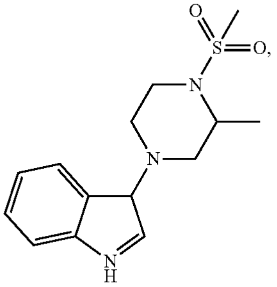
187
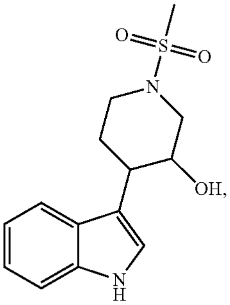
191
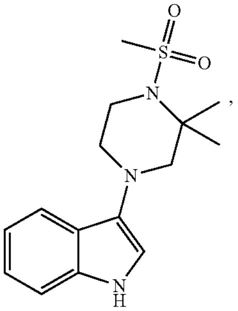
194
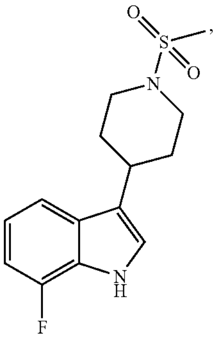
197
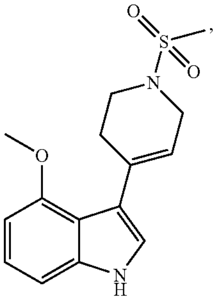
-continued
204
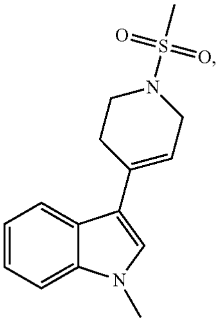
206
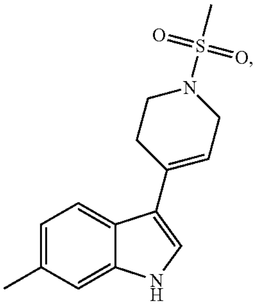
207
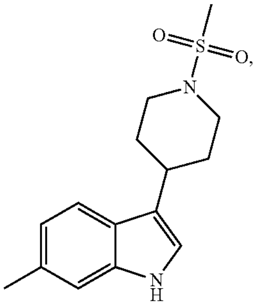
209
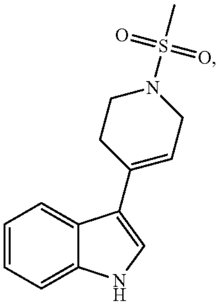
213
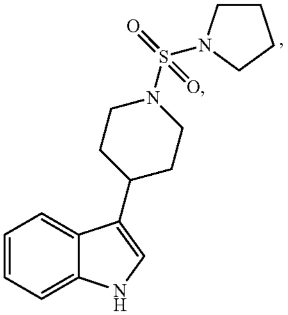

-continued
215
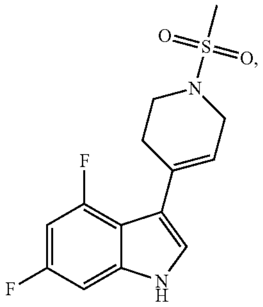
216
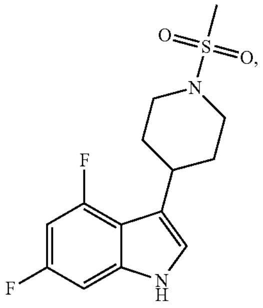
217
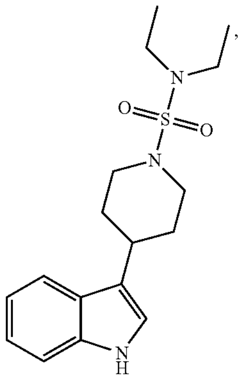
218
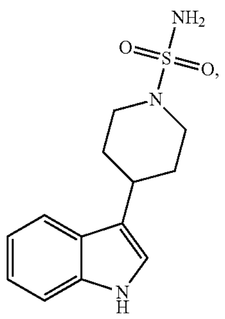
-continued
219
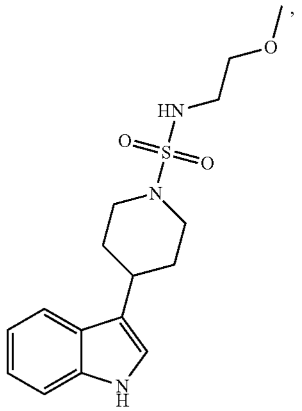
220
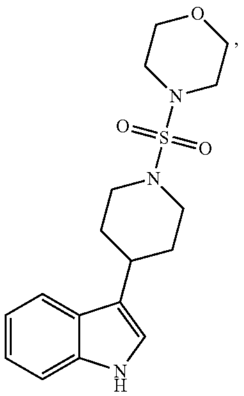
222
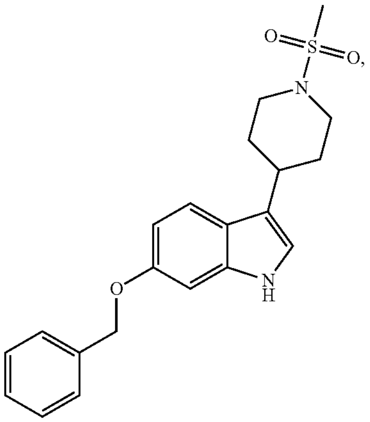
224
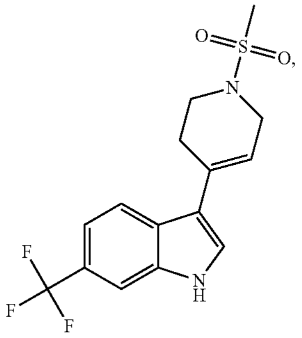

-continued
227
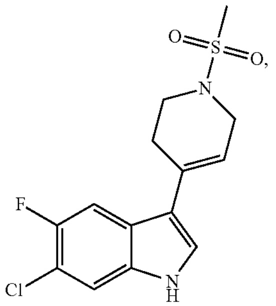
230
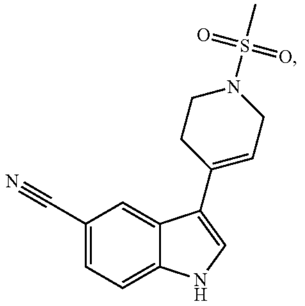
234
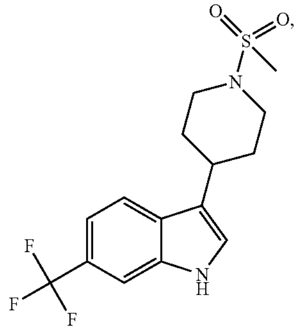
235
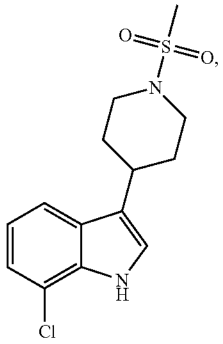
236
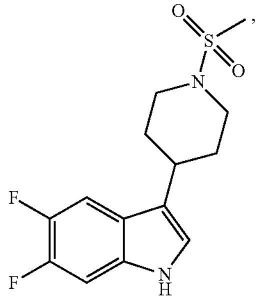
-continued
239
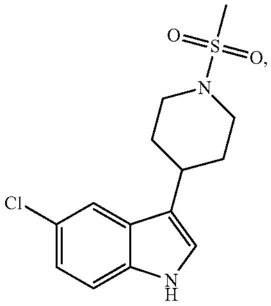
240
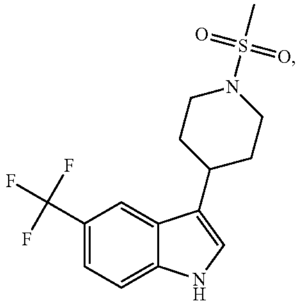
243
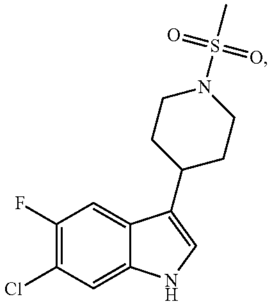
244
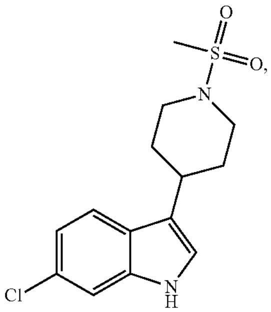
248
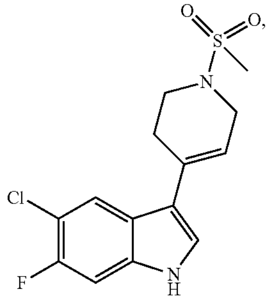

-continued
249
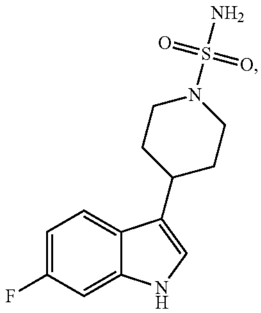
250
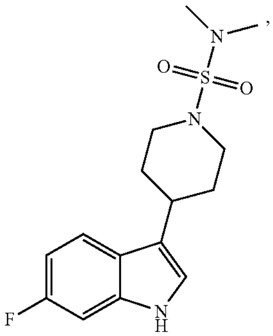
251
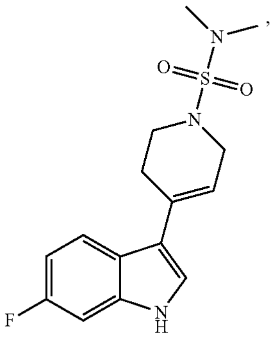
253
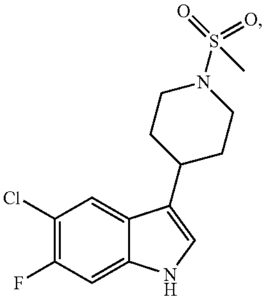
253
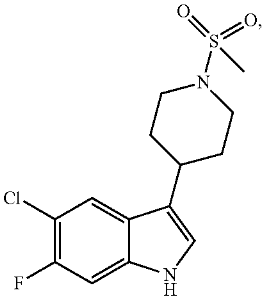
-continued
254
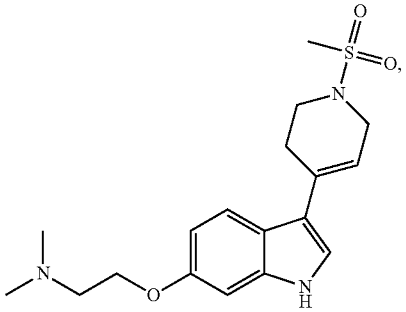
256
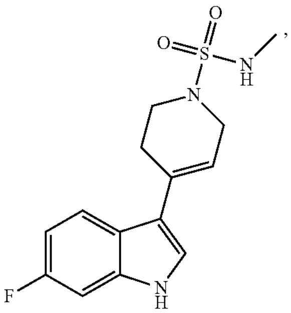
257
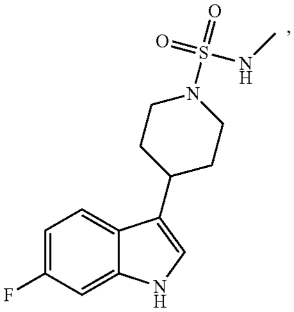
258
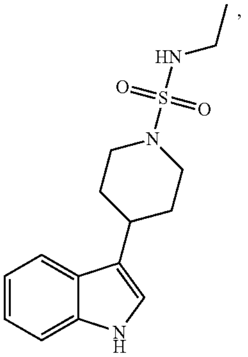
259
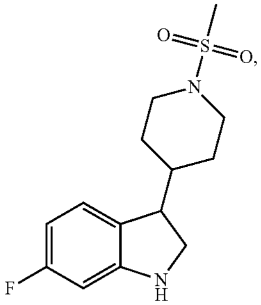

-continued
285
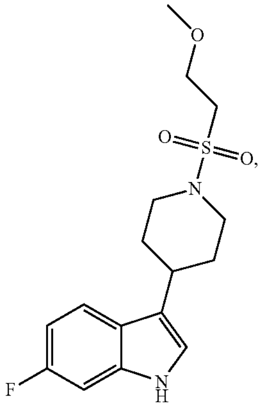
286
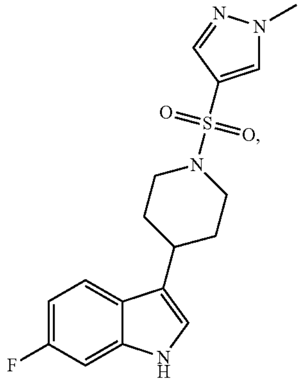
287
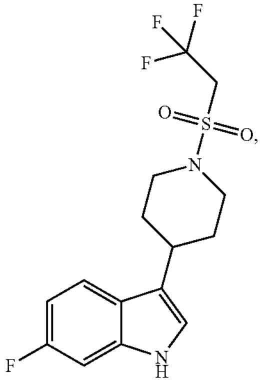
288
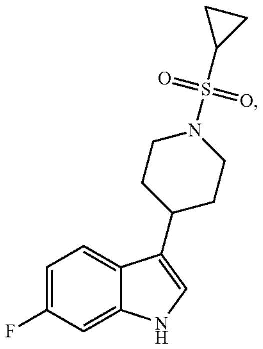
-continued
289
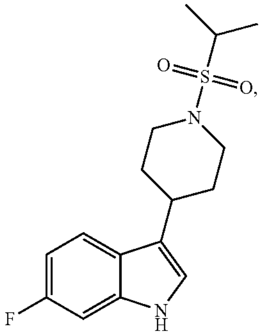
291
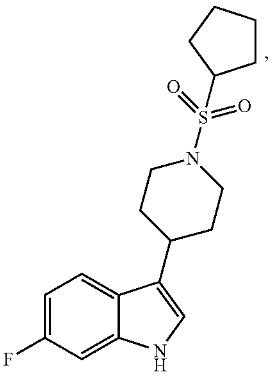
292
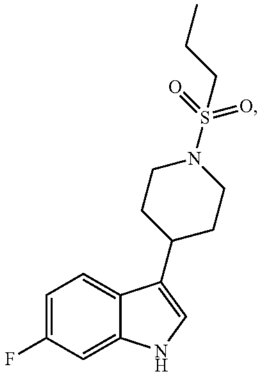
293
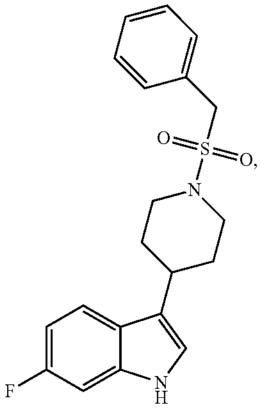

-continued
295
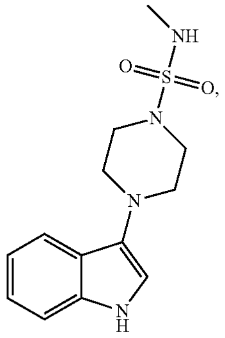
296
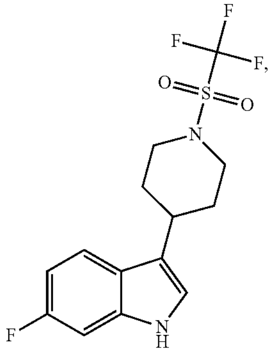
297
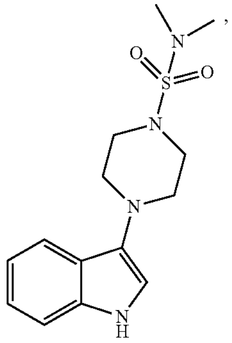
300
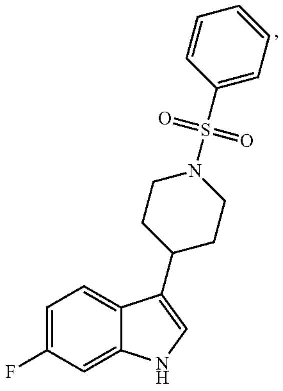
-continued
311
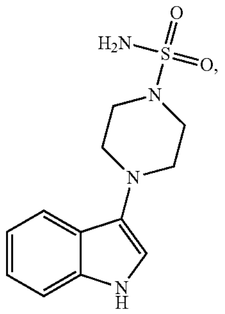
314
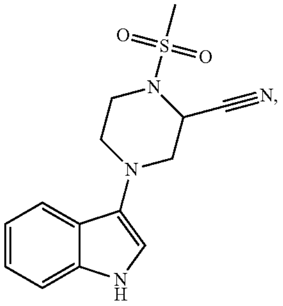
317
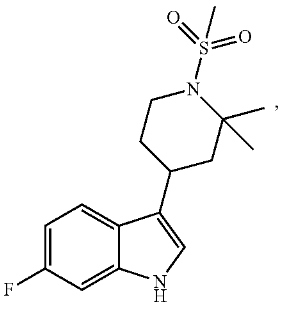
318
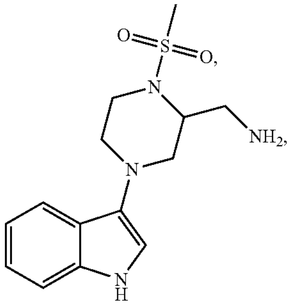
and
319
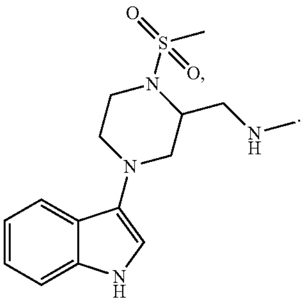

9. A pharmaceutical composition comprising a compound of claim 1.

10. The pharmaceutical composition of claim 9 for treating a cancer, further comprising a further agent for treating cancer; wherein the further agent is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents (such as an anti-tumour vaccine, an oncolytic virus, an immune stimulatory antibody such as anti-CTLA4, anti-PD1, anti-PDL-1, anti-OX40, anti-41BB, anti-CD27, anti-CD40, anti-LAG3, anti-TIM3, and anti-GITR, a novel adjuvant, a peptide, a cytokine, a chimeric antigen receptor T cell therapy (CAR-T), a small molecule immune modulator, tumour microenvironment modulators, and anti-angiogenic agents), proapoptotic agents and cell cycle signalling inhibitors.

11. A pharmaceutical kit for treating a cancer, which pharmaceutical kit comprises:

(a) a compound of claim 1; and (b) a further agent for treating cancer; wherein the further agent is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents (such as an anti-tumour vaccine, an oncolytic virus, an immune stimulatory antibody such as anti-CTLA4, anti-PD1, anti-PDL-1, anti-OX40, anti-41BB, anti-CD27, anti-CD40, anti-LAG3, anti-TIM3, and anti-GITR, a novel adjuvant, a peptide, a cytokine, a chimeric antigen receptor T cell therapy (CAR-T), a small molecule immune modulator, tumour microenvironment modulators, and anti-angiogenic agents), proapoptotic agents and cell cycle signalling inhibitors;

wherein the compound and the further agent are suitable for administration simultaneously, sequentially or separately.

12. A compound of claim 1, which is a compound of any of the following formulae:

69

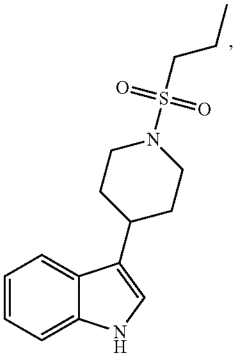
,

-continued

72

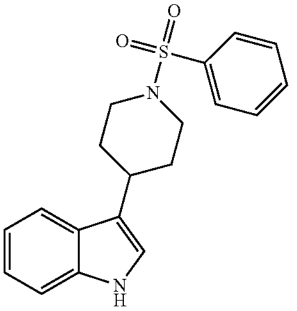
,

73

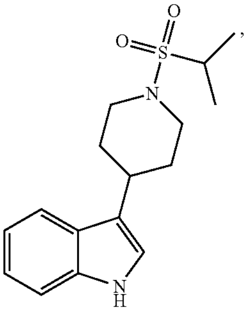
,

74

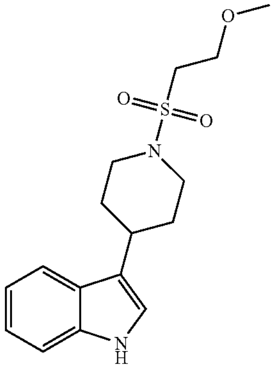
,

75

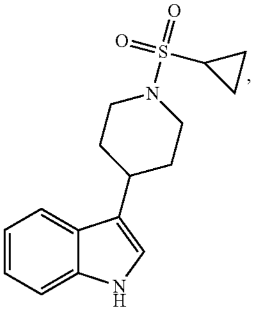
,

76

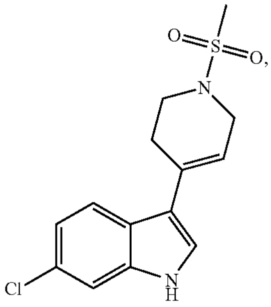
,

-continued
78
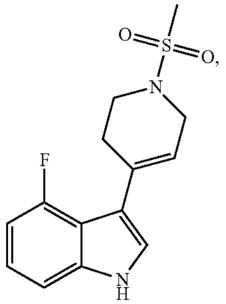
85
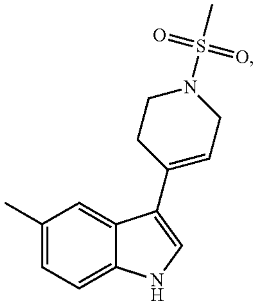
90
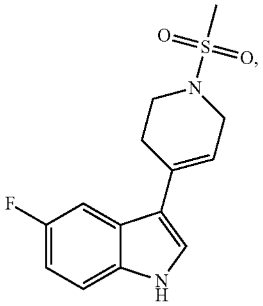
92
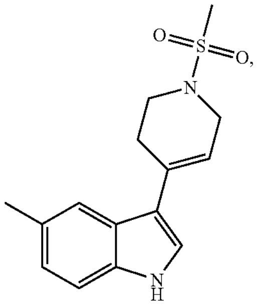
93
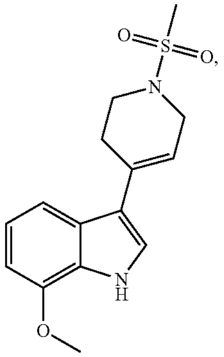
-continued
95
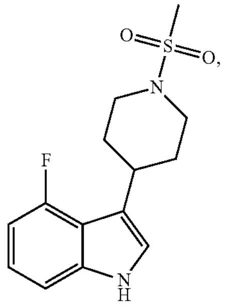
96
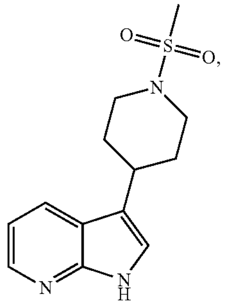
97
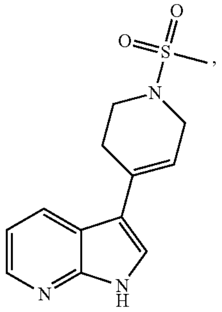
100
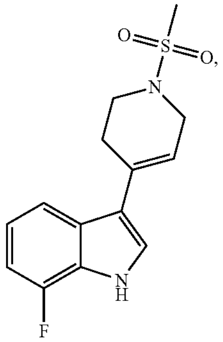
108
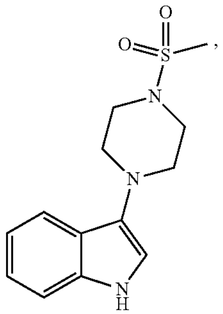

-continued
112
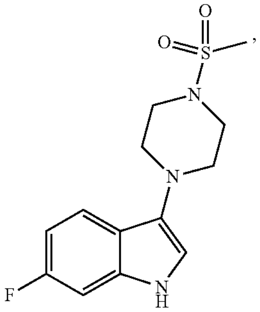
128
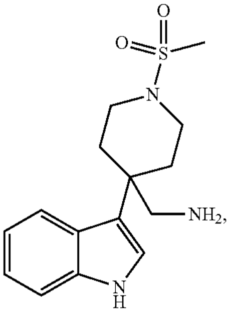
130
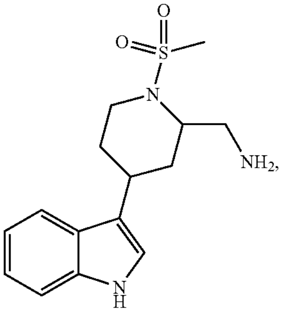
132
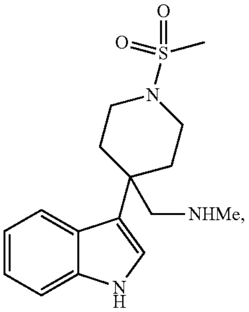
134
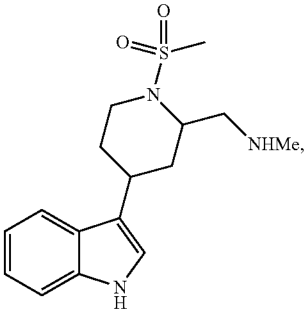
-continued
136
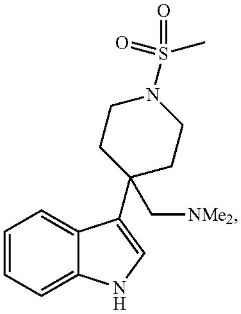
138
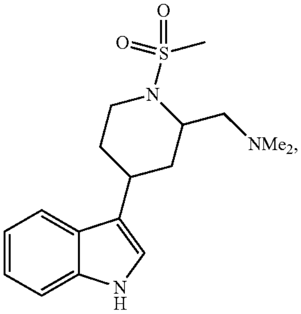
140
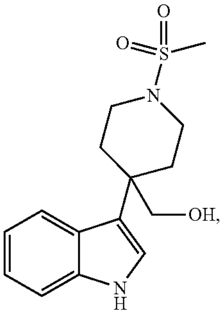
142
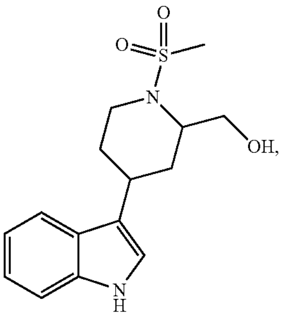
144
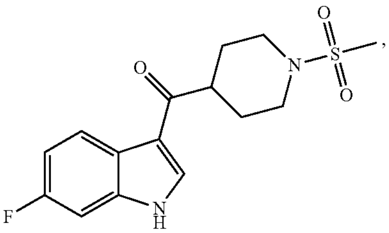

-continued
146
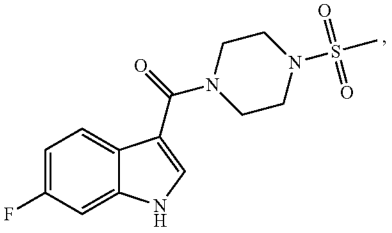
159
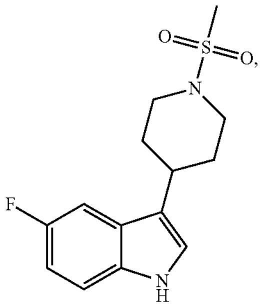
160
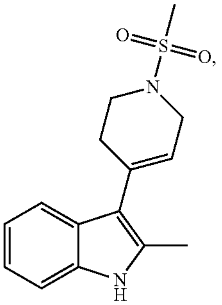
161
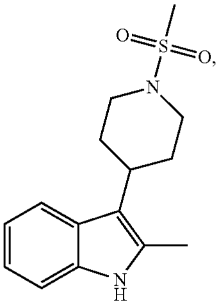
166
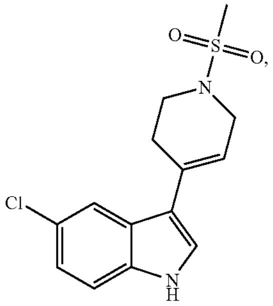
-continued
168
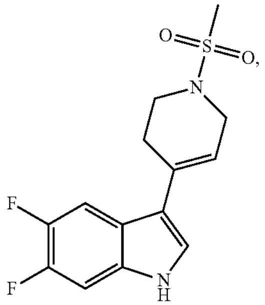
170
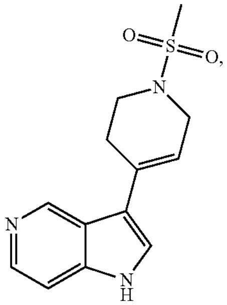
171
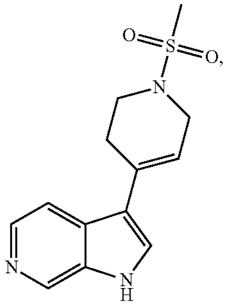
175
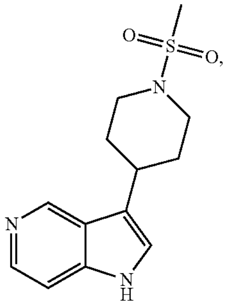
176
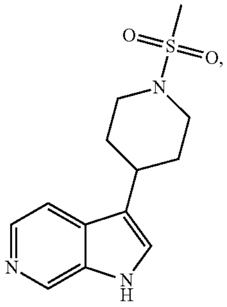

-continued
177
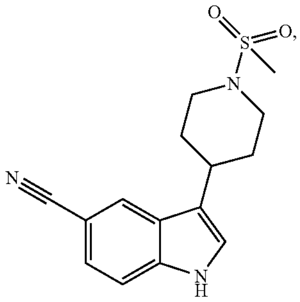
186
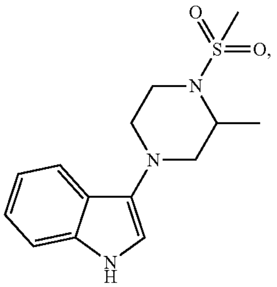
187
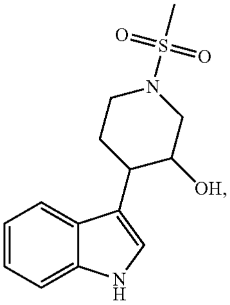
191
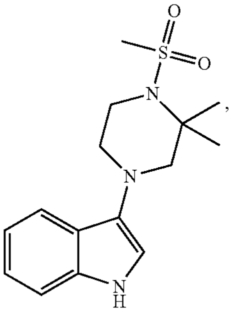
194
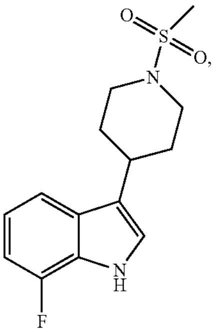
-continued
197
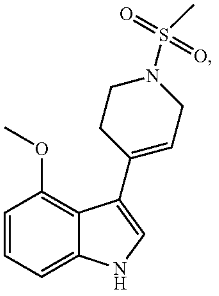
204
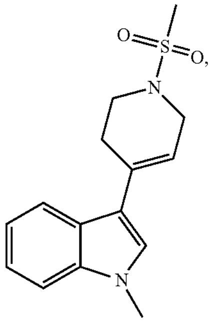
206
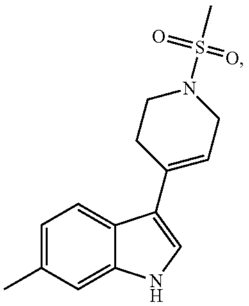
207
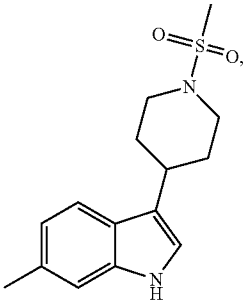
209
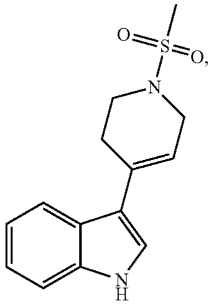

-continued
213
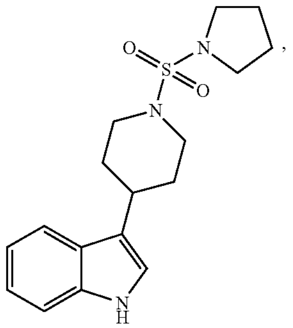
215
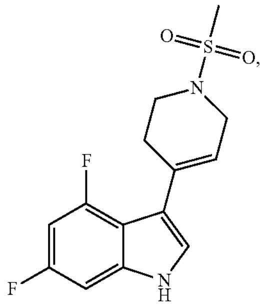
216
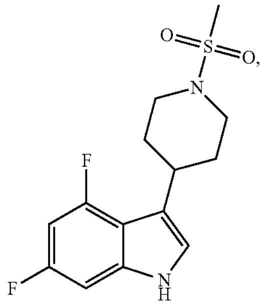
217
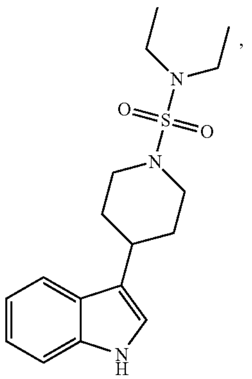
218
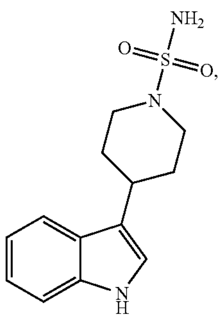
-continued
219
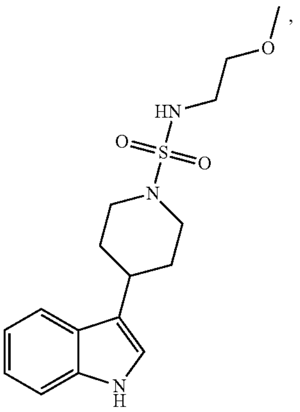
222
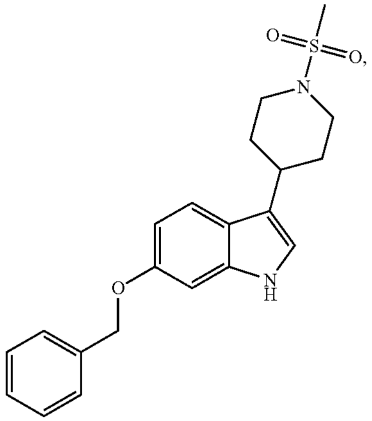
224
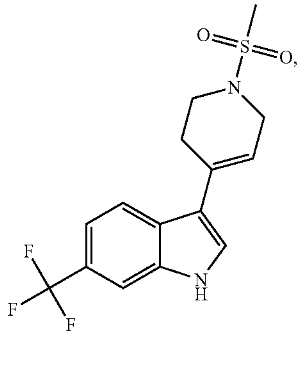
227
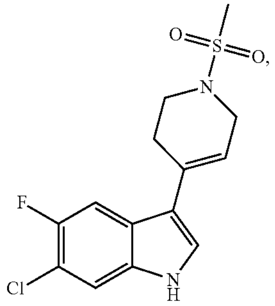

-continued
230
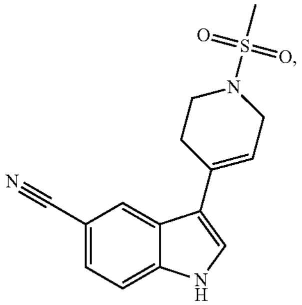
234
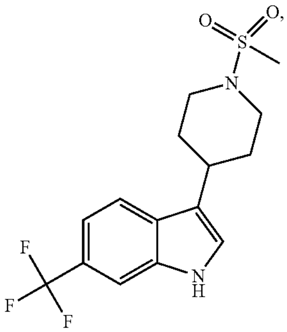
235
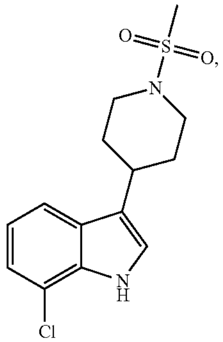
236
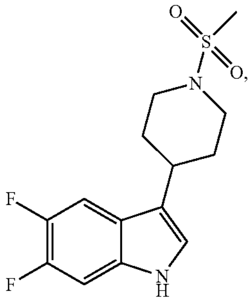
239
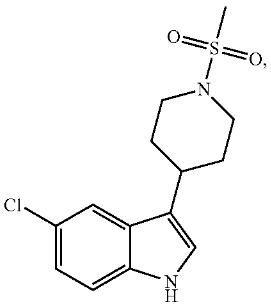
-continued
240
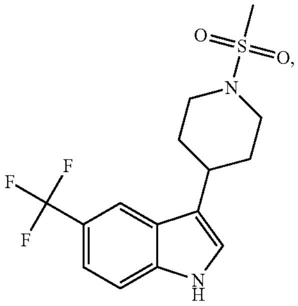
243
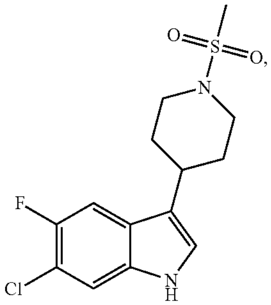
244
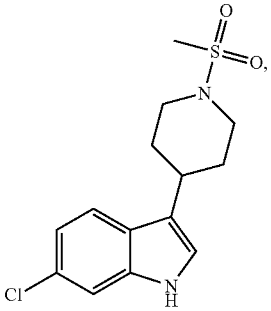
248
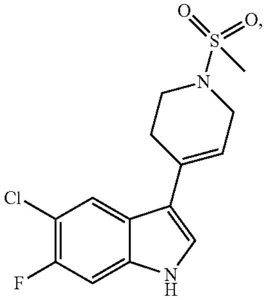
249
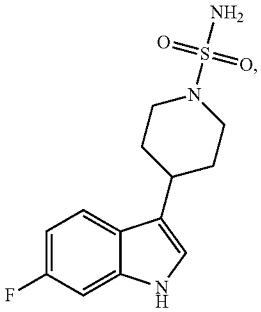

-continued
250
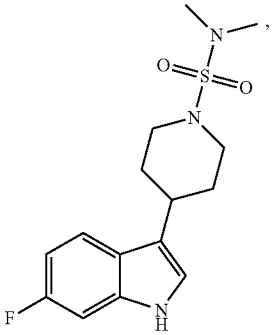
251
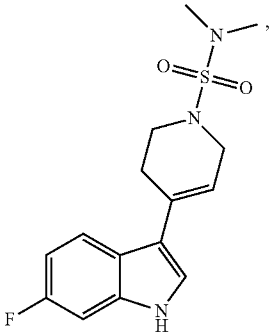
253
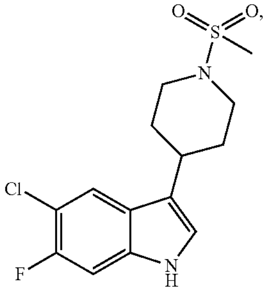
254
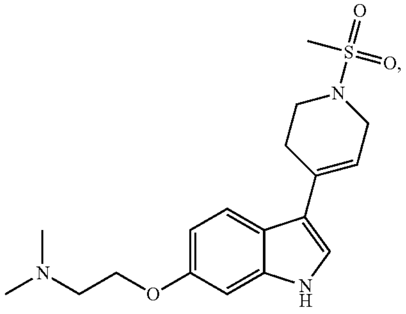
256
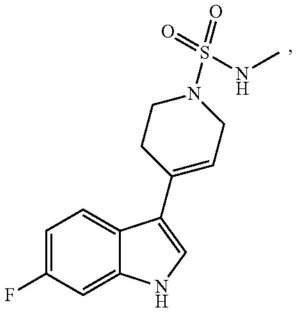
-continued
257
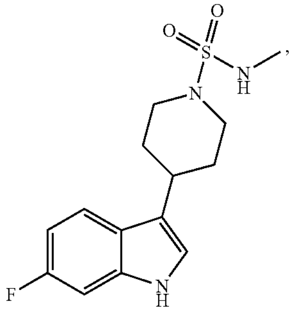
258
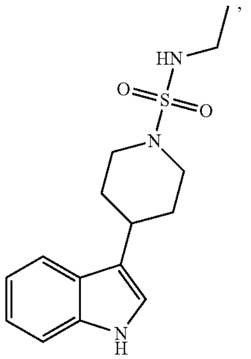
259
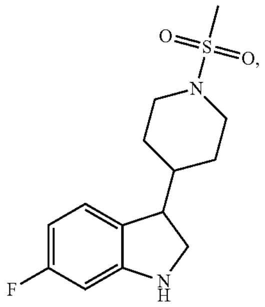
285
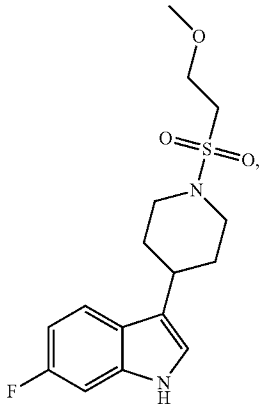

-continued
286
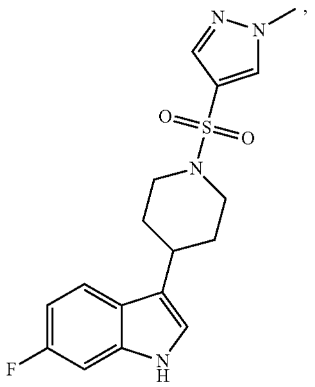
,
287
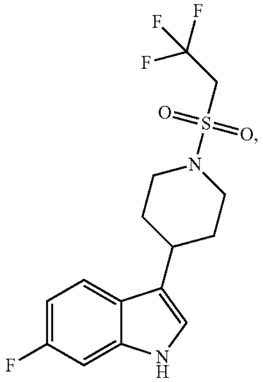
,
288
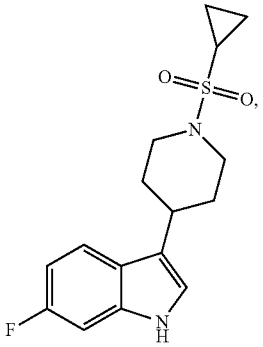
,
289
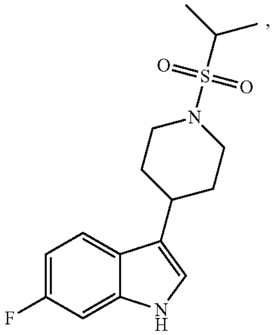
,
-continued
291
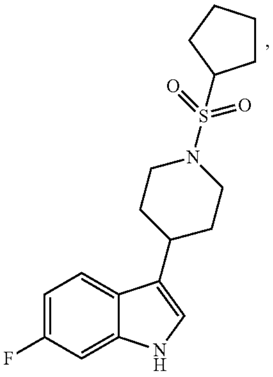
,
292
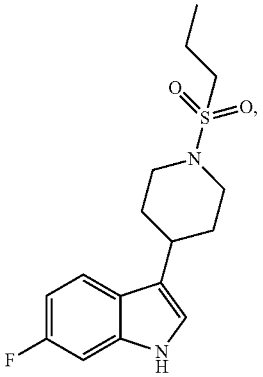
,
293
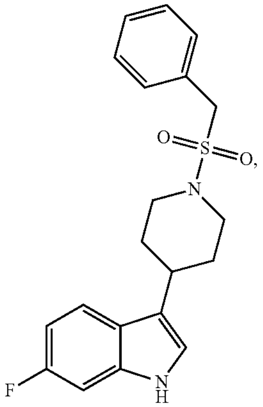
,
294
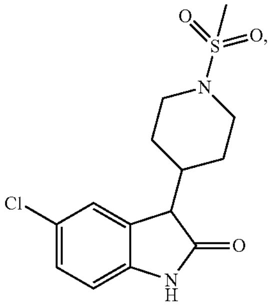
, -continued
295
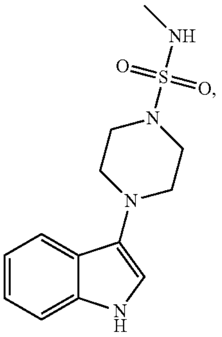
296
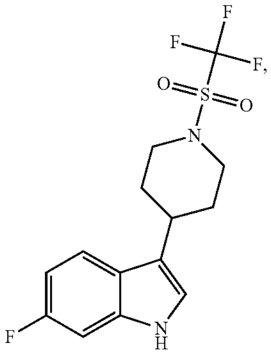
297
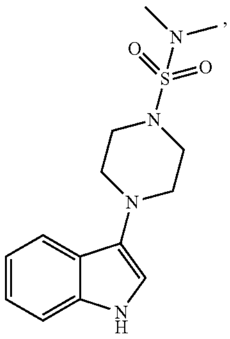
300
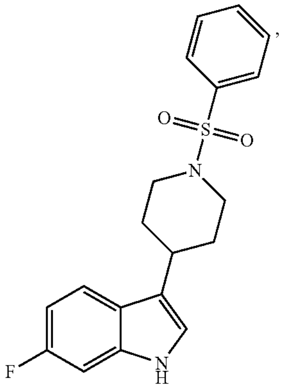
-continued
311
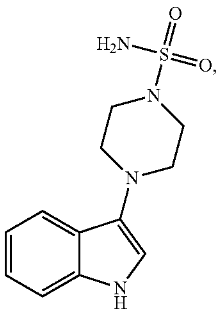
314
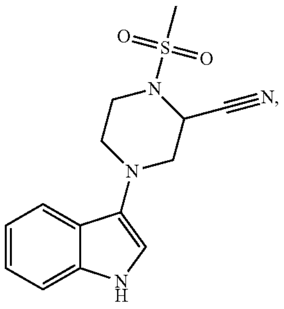
317
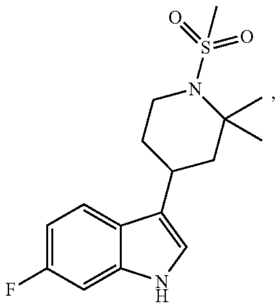
318
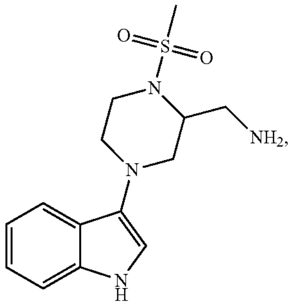
and
319
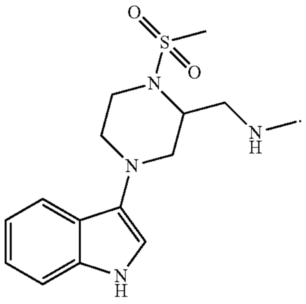
* * * * *